(12) United States Patent
Parhami et al.

(10) Patent No.: US 9,670,244 B2
(45) Date of Patent: *Jun. 6, 2017

(54) OXYSTEROL COMPOUNDS AND THE HEDGEHOG PATHWAY

(75) Inventors: Farhad Parhami, Los Angeles, CA (US); Michael E. Jung, Los Angeles, CA (US); Jennifer R. Dwyer, Los Angeles, CA (US); Khanhlinh Nguyen, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 850 days.

This patent is subject to a terminal disclaimer.

(21) Appl. No.: 12/224,430

(22) PCT Filed: Feb. 27, 2007

(86) PCT No.: PCT/US2007/005073
§ 371 (c)(1),
(2), (4) Date: Sep. 15, 2009

(87) PCT Pub. No.: WO2007/098281
PCT Pub. Date: Aug. 30, 2007

(65) Prior Publication Data
US 2010/0034781 A1    Feb. 11, 2010

Related U.S. Application Data

(60) Provisional application No. 60/776,990, filed on Feb. 27, 2006, provisional application No. 60/802,737, filed on May 22, 2006, provisional application No. 60/809,736, filed on May 31, 2006.

(51) Int. Cl.
*A61K 31/575* (2006.01)
*C07J 9/00* (2006.01)

(52) U.S. Cl.
CPC ...................................... *C07J 9/00* (2013.01)

(58) Field of Classification Search
CPC .......................................................... C07J 9/00
USPC .................................................... 514/182
See application file for complete search history.

(56) References Cited

U.S. PATENT DOCUMENTS

| | | |
|---|---|---|
| 3,309,387 A | 3/1967 | Furst et al. |
| 3,887,545 A | 6/1975 | Iacobelli et al. |
| 4,183,852 A | 1/1980 | Kaiser |
| 4,264,512 A | 4/1981 | Okamura et al. |
| 4,559,157 A | 12/1985 | Smith et al. |
| 4,608,392 A | 8/1986 | Jacquet et al. |
| 4,743,597 A | 5/1988 | Javitt et al. |
| 4,820,508 A | 4/1989 | Wortzman |
| 4,938,949 A | 7/1990 | Borch et al. |
| 4,992,478 A | 2/1991 | Geria |
| 5,166,320 A | 11/1992 | Wu et al. |
| 5,183,815 A | 2/1993 | Saari et al. |
| 5,219,740 A | 6/1993 | Miller et al. |
| 5,288,641 A | 2/1994 | Roizman |
| 5,723,455 A | 3/1998 | Tanabe et al. |
| 5,840,752 A | 11/1998 | Henry et al. |
| 5,929,062 A | 7/1999 | Haines |
| 6,017,904 A | 1/2000 | Reed et al. |
| 6,080,779 A | 6/2000 | Gasper et al. |
| 6,177,420 B1 | 1/2001 | Leemhuis et al. |
| 6,184,215 B1 | 2/2001 | Elias et al. |
| 6,316,503 B1 | 11/2001 | Li et al. |
| 6,436,917 B1 | 8/2002 | Droescher et al. |
| 6,518,262 B1 | 2/2003 | Leysen et al. |
| 6,586,189 B2 | 7/2003 | Forman |
| 6,893,830 B1 | 5/2005 | Janowski et al. |
| 6,906,069 B1 | 6/2005 | Li et al. |
| 7,060,450 B1 | 6/2006 | Tabin et al. |
| 7,196,220 B2 | 3/2007 | Pierce, Jr. et al. |
| 7,427,610 B2 | 9/2008 | Hillisch et al. |
| 8,071,575 B2 | 12/2011 | Pierce, Jr. et al. |
| 2003/0153541 A1 | 8/2003 | Dudley et al. |
| 2004/0072806 A1 | 4/2004 | Yao et al. |
| 2004/0077613 A1 | 4/2004 | Bamberg et al. |
| 2004/0176423 A1 | 9/2004 | Paralkar |
| 2004/0235739 A1 | 11/2004 | Mahanthappa |
| 2005/0095677 A1 | 5/2005 | Liu et al. |
| 2006/0251735 A1 | 11/2006 | Parhami |
| 2006/0270645 A1 | 11/2006 | Parhami |
| 2008/0070883 A1 | 3/2008 | Nagpal |
| 2009/0202660 A1 | 8/2009 | Parhami et al. |

(Continued)

FOREIGN PATENT DOCUMENTS

DE    102004042822 A1    3/2006
EP    0 415 731 A2    3/1991
(Continued)

OTHER PUBLICATIONS

Ciobanu et al., "Synthesis and steroid sulfatase inhibitory activity of C19- and C21-steroidal derivatives bearing a benzyl-inhibiting group." European Journal of Medicinal Chemistry, vol. 36(7-8), 659-671, 2001.*

Zimmerman et al., "Stereochemical effects in cyclopropane ring openings: biomimetic ring openings of all isomers of 22, 23-methylenecholesterol acetate". Journal of the American Chemical Society, vol. 106(19), pp. 5602-5612, 1984.*

Nagano et al., "Chemistry and Biochemistry of Chinese Drugs. Part II. Hydroxylated Sterols, Cytotoxic towards Cancerous Cells: Synthesis and Testing." Journal Chem. Research (S), 1977, 218.*

Kadiyala et al., "Culture expanded canine mesenchymal stem cells possess osteochondrogenic potential in vivo and in vitro", Cell Transplantation, vol. 6, No. 2 (1997) pp. 125-134.

Nakamura et al., "Stimulation of bone formation by intraosseous application of recombinant basic fibroblast growth factor in normal and ovariectomized rabbits", J. Orthopaedic Research, vol. 15, No. 2 (1997) pp. 307-313.

(Continued)

*Primary Examiner* — Barbara P Badio
(74) *Attorney, Agent, or Firm* — Mintz Levin Cohn Ferris Glovsky and Popeo, P.C.

(57) ABSTRACT

This invention relates, for example, to synthetic oxysterols. Also described are methods for using the compounds, including treating subjects in need thereof, and pharmaceutical compositions and kits for implementing methods of the invention.

17 Claims, 21 Drawing Sheets

(56) References Cited

U.S. PATENT DOCUMENTS

| | | |
|---|---|---|
| 2009/0202661 A1 | 8/2009 | Kirkpatrick |
| 2009/0220562 A1 | 9/2009 | Parhami |
| 2010/0012030 A1 | 1/2010 | Todd et al. |
| 2010/0034781 A1 | 2/2010 | Parhami et al. |
| 2010/0048944 A1 | 2/2010 | Parhami |
| 2010/0105645 A1 | 4/2010 | Parhami et al. |
| 2011/0008297 A1 | 1/2011 | Parhami et al. |
| 2012/0309730 A1 | 12/2012 | Parhami et al. |
| 2015/0118277 A1 | 4/2015 | Parhami et al. |
| 2015/0140059 A1 | 5/2015 | Parhami et al. |
| 2016/0159850 A1 | 6/2016 | Parhami et al. |
| 2016/0206631 A1 | 7/2016 | Parhami et al. |

FOREIGN PATENT DOCUMENTS

| | | |
|---|---|---|
| GB | 869007 A | 5/1961 |
| GB | 2 320 190 | 6/1998 |
| JP | S51-11114 B1 | 4/1976 |
| JP | 2000508911 A | 7/2000 |
| JP | 2000-511404 A | 9/2000 |
| JP | 2002-506030 A | 2/2002 |
| JP | 2002-506817 A | 3/2002 |
| WO | WO-90/07936 A1 | 7/1990 |
| WO | WO-91/02805 A2 | 3/1991 |
| WO | WO-93/9191 A1 | 5/1993 |
| WO | WO-93/10218 A1 | 5/1993 |
| WO | WO-93/11230 A1 | 6/1993 |
| WO | WO-93/25234 A1 | 12/1993 |
| WO | WO-93/25698 A1 | 12/1993 |
| WO | WO-94/03622 A1 | 2/1994 |
| WO | WO-94/26914 A1 | 11/1994 |
| WO | WO-95/13365 A1 | 5/1995 |
| WO | WO 97/40137 | 10/1997 |
| WO | WO 00/54759 | 9/2000 |
| WO | WO 01/15676 | 3/2001 |
| WO | WO 02/080952 | 10/2002 |
| WO | WO-2004/019884 | 3/2004 |
| WO | WO 2004/019884 A2 | 3/2004 |
| WO | WO-2005/020928 | 3/2005 |
| WO | WO 2005/028616 | 3/2005 |
| WO | WO/2005/020928 | 10/2005 |
| WO | WO-2005/123757 A1 | 12/2005 |
| WO | WO 2005/123757 A1 | 12/2005 |
| WO | WO-2006/024283 A2 | 3/2006 |
| WO | WO-2006/024283 A3 | 3/2006 |
| WO | WO-2006/034356 A2 | 3/2006 |
| WO | WO-2006/048264 A2 | 5/2006 |
| WO | WO/2006/012902 | 9/2006 |
| WO | WO-2006/110490 | 10/2006 |
| WO | WO 2006/110490 A | 10/2006 |
| WO | WO-2006/124836 A1 | 11/2006 |
| WO | WO-2007/028101 A2 | 3/2007 |
| WO | WO 2007/098281 A | 8/2007 |
| WO | WO-2007/106507 A2 | 9/2007 |
| WO | WO-2007/130423 A2 | 11/2007 |
| WO | WO-2008/011071 A2 | 1/2008 |
| WO | WO 2008/041003 A2 | 4/2008 |
| WO | WO-2008/082520 A2 | 7/2008 |
| WO | WO-2008/103951 A1 | 8/2008 |
| WO | WO-2008/109780 A1 | 9/2008 |
| WO | WO-2008/115469 A2 | 9/2008 |
| WO | WO-2009/073186 | 6/2009 |
| WO | WO-2011/006087 A1 | 1/2011 |
| WO | WO-2011/103175 A2 | 8/2011 |
| WO | WO-2012/024581 A2 | 2/2012 |
| WO | WO-2012/024583 A2 | 2/2012 |
| WO | WO-2012/024584 A2 | 2/2012 |
| WO | WO-2013/169397 A1 | 11/2013 |
| WO | WO-2013/169399 A1 | 11/2013 |
| WO | WO-2014/179756 A1 | 11/2014 |
| WO | WO-2015/168636 A1 | 11/2015 |
| ZA | 6808005 | 6/1969 |

OTHER PUBLICATIONS

Zhang et al., "Cyclooxygenase-2 regulates mesenchymal cell differentiation into the osteoblast lineage and is critically involved in bone repair", J. Clinical Investigation, vol. 109, No. 11 (2002) pp. 1405-1415.

Supplementary European Search Report (EP 03749213.9), Jun. 15, 2009.

Szendi et al., "1,5-Hydride shift in Wolff-Kishner reduction of (20R)-3β,20, 26-trihydroxy-27- norcholest-5-en-22-one; synthetic, quantum chemical, and NMR studies,"Steroids 67 (2002), pp. 31-38.

Shimizu et al., "20α, 22-Dihydroxycholesterol, an Intermediate in the Biosynthesis of Pregnenolone (3β-Hydroxypregn-5-en-20-one) from Cholesterol," J. Biol. Chem., 237(3) (1962), pp. 699-702.

Wada et al. Calcification of Vascular Smooth Muscle Cell Cultures : Inhibition by Osteopontin. 1999. Circ. Res. 84:166-178.

Aghaloo et al. Oxysterols enhance osteoblast differentiation in vitro and bone healing in vivo. J. Bone & Mineral Research. American Society for Bone and Mineral Research (27th Annual Meeting). vol. 20:9, sup. 1. (2005) p. S361 (Abstract M203).

Supplemental European Search Report (EP 06824888.9), Jul. 1, 2009.

Kim W et al. Osteogenic oxysterol, 20(S)-Hydroxycholesterol, inhibits PPAR gamma expression and adipogenic differentioation of bone marrow stromal cells through s hedgehog-, wnt-, and MAPK-Dependent Mechanism. J Bone Miner Res. 2006. 21(1): S394.

Aghaloo TL, Amantea CM, Cowan CM, Richardson JA, Wu BM, Parhami F, Tetradis S. Oxysterols enhance osteoblast differentiation in vitro and bone healing in vivo. J Orthop Res. Nov. 2007;25(11):1488-97 (also known as Aghaloo 2006 in press).

Akazawa C, Isuzuki H, Nakamura Y, Sasaki Y, Ohsaki K, Nakamura S, arakawa Y, Kohsaka S. The upregulated expression of sonic hedgehog in motor neurons after rat facial nerve axotomy. J Neuroscience 2004; 24:7923-7930.

Almeida M, Han L, Bellido T, Manolagas SC, Kousteni S. Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT. J Biol Chem. Dec. 16, 2005;280(50):41342-51.

Amantea CM et al. 2006, Oxysterols are novel activators of hedgehog and Wnt signaling, J Bone Miner Res 21:SI;S156.

Banerjee C, McCabe LR, Choi JY, Hiebert SW, Stein JL, Stein GS Lian JB. Runt homology domain proteins in osteoblast differentiation: AML3/CBFA1 is a major component of a bone-specific complex. J Cell Biochem. Jul. 1, 1997;66(1):1-8.

Bannai K, Morisaki M, Ikekawa N. Studies on steroids. Part 37. Synthesis of the four stereoisomers of 20,22-epoxycholesterol. J Chem Soc Perkins Trans 1 1979; 2116-2120.

Basu S, Michaëlsson K, Olofsson H, Johansson S, Melhus H. Association between oxidative stress and bone mineral density. Biochem Biophys Res Commun. Oct. 19, 2001;288(1):275-9.

Bennett CN, Longo KA, Wright WS, Suva LJ, Lane TF, Hankenson KD, MacDougald OA. Regulation of osteoblastogenesis and bone mass by Wnt10b. Proc Natl Acad Sci U S A. Mar. 1, 2005;102(9):3324-9.

Bennett CN, Ross SE, Longo KA, Bajnok L, Hemati N, Johnson KW, Harrison SD, MacDougald OA. Regulation of Wnt signaling during adipogenesis. J Biol Chem. Aug. 23, 2002;277(34):30998-1004.

Bergman RJ, Gazit D, Kahn AJ, Gruber H, McDougall S, Hahn TJ. Age-related changes in osteogenic stem cells in mice. J Bone Miner Res 1996; 11:568-577.

Bestmann HJ, Soliman FM. Synthesis and reaction of diazoacetyl chloride. Angew Chem 1979; 91:1012-1013.

Bijlsma MF, Peppelenbosch MP, Spek A. Hedgehog morphogen in cardiovascular disease. Circulation 114:1985-1991; 2006.

Bijlsma MF, Spek CA, Peppelenbosch MP. Hedgehog: an unusual signal transducer. BioEssays 26:387-394; 2004.

Bilezikian JP, Kurland ES. Therapy of male osteoporosis with parathyroid hormone. Calcif Tissue Int 2001; 69:248-251.

Bjorkhem I, Diczfalusy U. Oxysterols: friends, foes, or just fellow passengers? Arterioscler Thromb Vasc Biol 22:734-742; 2002.

(56) References Cited

OTHER PUBLICATIONS

Bjorkhem I, Meaney S, Diczfalusy U. Oxysterols in human circulation: which role do they play? Curr Opion Lipidol 13:247-253; 2002.
Bjorkhem I, Reihner E, Angelin B, Ewerth S, Akerlund J, Einarsson K. On the possible use of the serum level of 7α-hydroxycholesterol as a marker for incrased activity of the cholesterol 7α-hydroxylase in humans. J Lipid Res 1987; 28:889-894.
Boguslawski G, Hale LV, Yu XP, Miles RR, Onyia JE, Santerre RF, Chandrasekhar S. Activation of osteocalcin transcription involves interaction of protein kinase A- and protein kinase C-dependent pathways. J Biol Chem. Jan. 14, 2000;275(2):999-1006.
Boland GM, Perkins G, Hall DJ, Tuan RS. Wnt 3a promotes proliferation and suppresses osteogenic differentiation of adult human mesenchymal stem cells. J Cell Biochem. Dec. 15, 2004;93(6):1210-30.
Braunersreuther V, Mach F. Leukocyte recruitment in atherosclerosis: potential targets for therapeutic approaches? Cell Mol Life Sci 63:2079-2088; 2006.
Bunta W, Yoshiaki N, Takehiko O, Hisashi M. Steroids 2004, 69: 483-493.
Burger A, Colobert F, Hetru C, Luu B. Tetrahedron 1988, 44: 1141-1152.
Byon C, Gut M. Stereospecific synthesis of the four 20,22-epoxycholesterols and of (Z)20(22)-Dehydrocholesterol. J Org Chem 1976; 41:3716-3722.
Byrd N, Grabel L. Hedgehog signaling in murine vasculogenesis and angiogenesis. Trends Cardiovasc Med 14:308-313; 2004.
Cadot C, Poirier D, Philip A. Tetrahedron 2006, 62: 4384-4392.
Caplan AI, Bruder SP. Mesenchymal stem cells: building blocks for molecular medicine in the 21st century. Trends Mol Med. Jun. 2001;7(6): 259-64. Review.
Caplan AI. The mesengenic process. Bone Repair and Regeneration 1994; 21:429-435.
Chan GK, Duque G. Age-related bone loss: old bone, new facts. Gerontology 2002; 48:62-71.
Chaudhuri NK, Williams IG, Nickolson R, Gut M. Stereochemistry of the addition reactions of Grignard reagents to 20-keto steroids. Syntheses of 17α,20α-dihydroxycholesterol. J Org Chem 1969; 34:3759-3766.
Chen D, Zhao M, Mundy GR. Bone morphogenetic proteins. Growth Factors. Dec. 2004;22(4):233-41. Review.
Chen JK, Iaipale J, Cooper MK, Beachy PA. Inhibition of hedgehog signaling by direct binding of cyclopamine to Smoothened. Genes & Develop 2002; 16:2743-2748.
Chen XD, Shi S, Xu T, Robey PG, Young MF. Age-related osteoporosis in biglycan-deficient mice is related to defects in bone marrow stromal cells. J Bone Miner Res. Feb. 2002;17(2):331-40.
Chuu CP, Hiipakka RA, Kokontis JM, Fukuchi J, Chen RY, Liao S. Inhibition of tumor growth and progression of LNCaP prostate cancer cells in athymic mice by androgen and liver X receptor agonist. Cancer Res. Jul. 1, 2006;66(13):6482-6.
Clément-Lacroix P, Ai M, Morvan F, Roman-Roman S, Vayssière B, Belleville C, Estrera K, Warman ML, Baron R, Rawadi G. Lrp5-independent activation of Wnt signaling by lithium chloride increases bone formation and bone mass in mice. Proc Natl Acad Sci U S A. Nov. 29, 2005;102(48):17406-11.
Clevers H. Wnt/beta-catenin signaling in development and disease. Cell. Nov. 3, 2006;127(3):469-80. Review.
Cohen MM. The hedgehog signaling network. Am J Med Gen 2003; 123A:5-28.
Cummings SR, Melton LJ. Epidemiology and outcomes of osteoporotic fractures. Lancet. May 18, 2002;359(9319):1761-7. Review.
Day TF, Guo X, Garrett-Beal L, Yang Y. Wnt/beta-catenin signaling in mesenchymal progenitors controls osteoblast and chondrocyte differentiation during vertebrate skeletogenesis. Dev Cell. May 2005;8(5):739-50.
De la Rosa MA, Velarde E, Guzman A. Synthetic Commun. 1990, 20: 2059-2064.

Debiais F, Lefèvre G, Lemonnier J, Le Mée S, Lasmoles F, Mascarelli F, Marie PJ. Fibroblast growth factor-2 induces osteoblast survival through a phosphatidylinositol 3-kinase-dependent, -beta-catenin-independent signaling pathway. Exp Cell Res. Jul. 1, 2004;297(1):235-46.
Devos A, Remion J, Frisque-Hesbain AM, Colens A, Ghosez L. Syntheseis of acylhalides under very mild conditions. J Chem soc Chem Commun 1979; 1180-1181.
Drew J, Letellier M, Morand P, Szabo AG. J of Org. Chem 1987, 52: 4047-4052 (no detailed info found in PubMed).
Ducy P, Zhang R, Geoffroy V, Ridall AL, Karsenty G. Osf2/Cbfa1 : A transcriptional activator of osteoblast differentiation. Cell 1997; 89:747-754.
Ducy P. Cbfa1: a molecular switch in osteoblast biology. Dev Dyn. Dec. 2000;219(4):461-71.
Eastell R. Treatment of postmenopausal osteoporosis. New Eng J Med 1998; 338(11):736-746.
Edwards PA, Ericsson J. Sterols and isoprenoids: signaling molecules derived from the cholesterol biosynthetic pathway. Annu Rev Biochem 68:157-185; 1999.
Edwards PA, Kast HR, Anisfeld AM. BAREing it all: the adoption of LXR and FXR and their roles in lipid metabolism. J Lipid Res 2002; 43:2-12.
Ettinger MP. Aging bone and osteoporosis: strategies for preventing fractures in the elderly. Arch Intern Med. Oct. 13, 2003;163(18):2237-46. Review.
Fajas L, Schoonjans K, Gelman L, Kim JB, Najib J, Martin G, Fruchart JC, Briggs M, Spiegelman BM, Auwerx J. Regulation of peroxisome proliferator-activated receptor gamma expression by adipocyte differentiation and determination factor 1/sterol regulatory element binding protein 1: implications for adipocyte differentiation and metabolism. Mol Cell Biol. Aug. 1999; 19(8):5495-503.
Franceschi RT, Wang D, Krebsbach PH, Rutherford RB. Gene therapy for bone formation: in vitro and in vivo osteogenic activity of an adenovirus expressing BMP7. J Cell Biochem. Jun. 6, 2000;78(3):476-86.
Franceschi RT, Xiao G. Regulation of the osteoblast-specific transcription factor, Runx2: responsiveness to multiple signal transduction pathways. J Cell Biochem. Feb. 15, 2003;88(3):446-54. Review.
Fujita T, Azuma Y, Fukuyama R, Hattori Y, Yoshida C, Koida M, Ogita K, Komori T. Runx2 induces osteoblast and chondrocyte differentiation and enhances their migration by coupling with PI3K-Akt signaling. J Cell Biol. Jul. 5, 2004;166(1):85-95. Epub Jun. 28, 2004.
Fukuchi J, Kokontis JM, Hiipakka RA, Chuu CP, Liao S. Antiproliferative effect of liver X receptor agonists on LNCaP human prostate cancer cells. Cancer Res. Nov. 1, 2004;64(21):7686-9.
Garrett IR, Chen D, Gutierrez G, Zhao M, Escobedo A, Rossini G, Harris SE, Gallwitz W, Kim KB, Hu S, Crews CM, Mundy GR. Selective inhibitors of the osteoblast proteasome stimulate bone formation in vivo and in vitro. J Clin Invest. Jun. 2003;111(11):1771-82.
Gaur T, Lengner CJ, Hovhannisyan H, Bhat RA, Bodine PV, Komm BS, Javed A, van Wijnen AJ, Stein JL, Stein GS, Lian JB. Canonical Wnt signaling promotes osteogenesis by directly stimulating Runx2 gene expression. J Biol Chem. Sep. 30, 2005;280(39):33132-40. Epub Jul. 25, 2005.
Gen AVD, Wiedhaup K, Swoboda JJ, Dunathan HC, Johnson WS. J Am Chem Soc 1973, 95: 2656-2663.
Ghosh-Choudhury N, Abboud SL, Nishimura R, Celeste A, Mahimainathan L, Choudhury GG. Requirement of BMP-2-induced phosphatidylinositol 3-kinase and Akt serine/threonine kinase in osteoblast differentiation and Smad-dependent BMP-2 gene transcription. J Biol Chem. Sep. 6, 2002;277(36):33361-8. Epub Jun. 25, 2002 Erratum in: J Biol Chem. May 2, 2003;278(18):16452.
Ghosh-Choudhury N, Mandal CC, Choudhury GG. Statin-induced Ras activation integrates the phosphatidylinositol 3-kinase signal to Akt and MAPK for bone morphogenetic protein-2 expression in osteoblast differentiation. J Biol Chem. Feb. 16, 2007;282(7):4983-93.

(56) References Cited

OTHER PUBLICATIONS

Gimble JM, Robinson Covered Entity, Wu X, Kelly KA, Rodriguez BR, Kliewer SA, Lehmann JM, Morris DC. Peroxisome proliferator-activated receptor-γ activation by thiazolidinediones induces adipogenesis in bone marrow stromal cells. Mol Pharmacol 1996; 50:1087-1094.
Goltzman D. Discoveries, drugs and skeletal disorders. Nat Rev Drug Discov. Oct. 2002;1(10):784-96.
Gordon MD, Nusse R. Wnt signaling: multiple pathways, multiple receptors, and multiple transcription factors. J Biol Chem. Aug. 11, 2006;281(32):22429-33. Epub Jun. 22, 2006. Review.
Gori F, Thomas T, Hicok KC, Spelsberg TC, Riggs BL. Differentiation of human marrow stromal precursor cells: bone morphogenetic protein-2 increases OSF2/CBFA1, enhances osteoblast commitment, and inhibits late adipocyte maturation. J Bone Miner Res. Sep. 1999;14(9):1522-35.
Hanada K, Dennis JE, Caplan AI. Stimulatory effects of basic fibroblast growth factor and bone morphogenetic protein-2 osteogenic differentiation of rat bone marrow-derived mesenchymal stem cells. J. Bone and Mineral Research 1997, 12(10): 1606-1614.
Hanley K, Ng DC, He SS, Lau P, Min K, Elias PM, Bikle DD, Mangelsdorf DJ, Williams ML, Feingold KR. Oxysterols induce differentiation in human keratinocytes and increase AP-1-dependent involucrin transcription. J Invest Dermatol 2000; 114:545-553.
Hayden JM, Brachova L, Higgins K, Obermiller L, Sevanian A, Khandrika S, Reaven PD. Induction of moncyte differentiation and foam cell formation in vitro by 7-ketocholesterol. J Lipid Res 2002; 43:26-35.
Hicok KC, Thomas T, Gori F, Rickard DJ, Spelsberg TC, Riggs BL. Development and characterization of conditionally immortalized osteoblast precursor cell lines from human bone marrow stroma. J Bone Miner Res 1998; 13(2):205-2217.
Hill TP, Später D, Taketo MM, Birchmeier W, Hartmann C. Canonical Wnt/beta-catenin signaling prevents osteoblasts from differentiating into chondrocytes. Dev Cell. May 2005;8(5):727-38.
Honda M, Komori T. Biologically active glycosides from Asteroidia. XI. Structures of thornasterols A and B. Tetrahedron Lett 1986; 27:3396-3372.
Honda T, Katoh M, Yamane S. J Chem Soc., Perkin Trans. 1996, 1: 2291-2296 (no detailed info found in PubMed).
Hosack DA, Dennis G Jr, Sherman BT, Lane HC, Lempicki RA. Identifying biological themes within lists of genes with EASE. Genome Biol. 2003;4(10):R70. Epub Sep. 11, 2003.
Hu H, Hilton MJ, Tu X, Yu K, Ornitz DM, Long F. Sequential roles of hedgehog and Wnt signaling in osteoblast development. Development 132:49-60; 2004.
Ichioka N, Inaba M, Kushida T, Esumi T, Takahara K, Inaba K, Ogawa R, Iida H, Ikehara S. Prevention of senile osteoporosis in SAMP6 mice by intrabone marrow injection of allogeneic bone marrow cells. Stem Cells. 2002;20(6):542-51.
Iwata H, Sakano S, Itoh T, Bauer TW. Demineralized bone matrix and native bone morphogenetic protein in orthopaedic surgery. Clin Orthop Relat Res. Feb. 2002;(395):99-109. Review.
Johnson ML, Harnish K, Nusse R, Van Hul W. LRP5 and Wnt signaling: a union made for bone. J Bone Miner Res. Nov. 2004;19(11):1749-57.
Jung ME, Johnson TW. First total synthesis of Zestobergesterol A and active structural analogues of the Zestobergesterol. Organic Lett 1999; 1:1671-1674.
Juvet LK, Andresen SM, Schuster GU, Dalen KT, Tobin KA, Hollung K, Haugen F, Jacinto S, Ulven SM, Bamberg K, Gustafsson JA, Nebb HI. On the role of liver X receptors in lipid accumulation in adipocytes. Mol Endocrinol. Feb. 2003;17(2):172-82.
Kametani T, Tsubuki M, Higurashi K, Honda T. J Org Chem 1986, 51: 2932-2939.
Kennell JA, MacDougald OA. Wnt signaling inhibits adipogenesis through beta-catenin-dependent and -independent mechanisms. J Biol Chem. Jun. 24, 2005;280(25):24004-10.
Kha HT, Basseri B, Shouhed D, Richardson J, Tetradis S, Hahn TJ, Parhami F. Oxysterols regulate differentiation of mesenchymal stem cells: pro-bone and anti-fat. J Bone Miner Res 19:830-840; 2004.
Kim JB, Wright HM, Wright M, Spiegelman BM. ADD1/SREBP1 activates PPARgamma through the production of endogenous ligand. Proc Natl Acad Sci U S A. Apr. 14, 1998;95(8):4333-7.
Komori T. Regulation of skeletal development by the Runx family of transcription factors. J Cell Biochem. Jun. 1, 2005;95(3):445-53.
Kurland Es, Cosman F, McMahon DJ, Rosen CJ, Lindsay R, Bilezikian J. Parathyroid hormone as a therapy for idiopathic osteoporosis in men: effects on bone mineral density and bone markers. J Clin Endocrinol Metab 2000; 85:3069-3076.
Lehmann IM, Kliewer SA, Moore LB, Smith-Oliver TA, Oliver BB, Su J, Sundseth SS, Winegar DA, Blanchard DE, Spencer TA, Willson TM. Activation of the nuclear receptor LXR by oxysterols defines a new hormone response pathway. J Biol Chem 1997; 272:3137-3140.
Li RH, Wozney JM. Delivering on the promise of bone morphogenetic proteins. Trends Biotechnol. Jul. 2001;19(7):255-65. Review.
Libby P. Inflammation in atherosclerosis. Nature 420:868-874; 2002.
Lieberman JR, Daluiski A, Einhorn TA. The role of growth factors in the repair of bone. J Bone & Joint Surg 2002; 84A:1032-1044.
Long F, Zhang XM, Karp S, Yang Y, McMahon AP. Genetic manipulation of hedgehog signaling in the endochondral skeleton reveals a direct role in the regulation of chondrocyte proliferation. Development 2001; 128:5099-5108.
Lum L, Beachy PA. The hedgehog response network: sensors, switches, and routers. Science 304:1755-1759; 2004.
Maeda T, Matsunuma A, Kawane T, Horiuchi N. Simvastatin promotes osteoblast differentiation and mineralization in MC3T3-E1 cells. Biochem Biophys Res Commun. Jan. 26, 2001;280(3):874-7.
Maggio D, Barabani M, Pierandrei M, Polidori MC, Catani M, Mecocci P, Senin U, Pacifici R, Cherubini A. Marked decrease in plasma antioxidants in aged osteoporotic women: results of a cross-sectional study. J Clin Endocrinol Metab. Apr. 2003;88(4):1523-7.
Majors AK, Boehm CA, Nitto H, Midura RJ, Muschler GF. Characterization of human bone marrow stromal cells with respect to osteoblastic differentiation. J Bone & Joint Surgery 1997; 15:546-557.
Makino T, Shibata K, Rohrer DC, Osawa Y. Steroid conformations in solid and solution: stereoselectivity of Grignard addition to 20-keto steroids. J. Org. Chem. 1978, 43(2): 276-280.
Manolagas SC. Cellular and molecular mechanisms of osteoporosis. Aging 1998; 10(3):182-190.
Manolagas SC. Birth and death of bone cells: basic regulatory mechanisms and implications for the pathogenesis and treatment of osteoporosis. Endocr Rev. Apr. 2000;21(2):115-37.
Mazzocchi PH, Wilson FK, Klinger L, Miniamikawa S. J Org Chem 1983, 48: 2981-2989 (no detailed info found in PubMed).
Mbalaviele G, Sheikh S, Stains JP, Salazar VS, Cheng SL, Chen D, Civitelli R. Beta-catenin and BMP-2 synergize to promote osteoblast differentiation and new bone formation. J Cell Biochem. Feb. 1, 2005;94(2):403-18.
Meaney S, Hassan M, Sakinis A, Lutjohann D, von Bergmann K, Wennmalm A, Diczfalusy U, Bjorkhem I. Evidence that the major oxysterols in human circulation originate from distinct pools of cholesterol: a stable isotope study. J Lipid Res 2001; 42:70-78.
Melton LI. How many women have osteoporosis now? J Bone Miner Res 1995; 10:175-177.
Meunier P, Aaron J, Edouard C, Vignon G. Osteoporosis and the replacement of cell populations of the marrow by adipose tissue: a quantitative study of 84 iliac bone biopsies. Clinical Orthopedics and Related Res 1971; 80:147-154.
Mitsunobu O. The use of diethyl azodicarboxylate and triphenylphosphine in syntheses and transformation of natural products. Synthesis 1981; 1-28.
Miyamoto K, Suzuki H, Yamamoto S, Saitoh Y, Ochiai E, Moritani S, Yokogawa K, Waki Y, Kasugai S, Sawanishi H, Yamagami H. Prostaglandin E2-mediated anabolic effect of a novel inhibitor of

(56) References Cited

OTHER PUBLICATIONS phosphodiesterase 4, XT-611, in the in vitro bone marrow culture. J Bone Miner Res. Aug. 2003;18(8):1471-7.

Mody N, Parhami F, Sarafian TA, Demer LL. Oxidative stress modulates osteoblastic differentiation of vascular and bone cells. Free Radic Biol Med. Aug. 15, 2001;31(4):509-19.

Moerman EJ, Teng K, Lipschitz DA, Lecka-Czernik B. Aging activates adipogenic and suppresses osteogenic programs in mesenchymal marrow stroma/stem cells: the role of PPAR-gamma2 transcription factor and TGF-beta/BMP signaling pathways. Aging Cell. Dec. 2004;3(6):379-89.

Morisaki M, Sato S, Ikekawa N. Studies on steroids. XLV. Synthesis of the four stereoisomers of 20,22-dihydroxycholesterol. Chem Pharm Bull 1977; 25:2576-2583.

Mullor JL, Dahmane N, Sun T, Ruiz i Altaba A. Wnt signals are targets and mediators of Gli function. Curr Biol. May 15, 2001;11(10):769-73.

Mullor JL, Sanchez P, Altaba AR. Pathways and consequences: hedgehog signaling in human disease. Trends Cell Bio 2002; 12:562-569.

Mundy GR. Directions of drug discovery in osteoporosis. Annu Rev Med 2002; 53;337-354.

Olkkonen VM, Lehto M. Oxysterols and oxysterol binding proteins: role in lipid metabolism and atherosclerosis. Ann Med 36:562-572; 2004.

Otto F, Thronell AP, Crompton T, Denzel A, Gilmour KC, Rosewell IR, Stamp GWH, Beddington RSP, Mundlos S, Olsen BR, Selby PB, Owen MJ. Cbfa1, a candidate gene for cleidocranial dysplasia syndrome, is essential for osteoblast differentiation and bone development. Cell 1997; 89:765-771.

Panakova D, Sprong H, Marois E, Thiele C, Eaton S. Lipoprotein particles are required for hedgehog and wingless signaling. Nature 435:58-65; 2005.

Parhami F, Mody N, Gharavi N, Ballard AJ, Tintut Y, Demer LL. Role of the cholesterol biosynthetic pathway in osteoblastic differentiation of marrow stromal cells. J Bone Miner Res. Nov. 2002;17(11):1997-2003.

Peet DJ, Janowski BA, Mangelsdorf DJ. The LXRs: a new class of oxysterol receptors. Curr Opin Genetics & Develop 1998; 8:571-575.

Pittenger MF, Mackay AM, Beck SC, Jaiswal RK, Douglas R, Mosca JD, Moorman MA, Simonetti DW, Craig S, Marshak DR. Multilineage potential of adult human mesenchymal stem cells. Science 1999; 284:143-147.

Poza J, Rega M, Paz V, Alonso B, Rodriguez J, Salvador N, Fernández A, Jiménez C. Synthesis and evaluation of new 6-hydroximinosteroid analogs as cytotoxic agents. Bioorg Med Chem. Jul. 15, 2007;15(14):4722-40.

Prockop DJ. Marrow stromal cells as stem cells for nonhematopoietic tissues. Science 1997; 276:71-74.

Quarto R, Thomas D, Liang CT. Bone progenitor cell deficits and the age-associated decline in bone repair capacity. Calcif Tissue Int. Feb. 1995;56(2):123-9.

Raisz LG. The osteoporosis revolution. Ann Int Med 1997; 126:458-462.

Rao AS. Addition reactions with formation of carbon-oxygen bones: (1) General methods of epoxidation. Comprehensive Organic Synthesis, Pergamon Press, Eds. Trost BM, Fleming I. 1991; 7 (chapter 3.1); 376-380.

Rawadi G, Vayssière B, Dunn F, Baron R, Roman-Roman S. BMP-2 controls alkaline phosphatase expression and osteoblast mineralization by a Wnt autocrine loop. J Bone Miner Res. Oct. 2003;18(10):1842-53.

Reeve J, Mitchell A, Tellez M, Hulme P, Green JR, Wardley-Smith B, Mitchell R. Treatment with parathyroid peptides and estrogen replacement for severe postmenopausal vertebral osteoporosis: prediction of long-term responses in spine and femur. J Bone Miner Res 2001; 19:102-114.

Reinholz GG, Getz B, Pederson L, Sanders ES, Subramaniam M, Ingle JN, Spelsberg TC. Bisphosphonates directly regulate cell proliferation, differentiation, and gene expression in human osteoblasts. Cancer Res. Nov. 1, 2000;60(21):6001-7.

Richardson JA et al. 2005, Characterization of osteogenic oxysterols and their molecular mechanism(s) of action, J Bone Miner Res 20:S1;S414.

Rickard DJ, Sullivan TA, Shenker BJ, Leboy PS, Kazhdan I. Induction of rapid osteoblast differentiation in rat bone marrow stromal cell cultures by dexamethasone and BMP-2. Dev Biol. Jan. 1994;161(1):218-28.

Riggs BL, Melton LJ 3rd. The prevention and treatment of osteoporosis. N Engl J Med. Aug. 27, 1992;327(9):620-7. Review.

Riobó NA, Lu K, Ai X, Haines GM, Emerson CP Jr. Phosphoinositide 3-kinase and Akt are essential for Sonic Hedgehog signaling. Proc Natl Acad Sci U S A. Mar. 21, 2006;103(12):4505-10.

Rodan GA, Martin TJ. Therapeutic approaches to bone diseases. Science 2000; 289:1508-1514.

Rodda SJ, McMahon AP. Distinct roles for Hedgehog and canonical Wnt signaling in specification, differentiation and maintenance of osteoblast progenitors. Development. Aug. 2006;133(16):3231-44.

Ruan B, Wilson WK, Shroepfer GJ. An improved synthesis of (20R,22R)-cholest-5-ene-3β,20,22-triol, and intermediate in steroid hormone formation and an activator of nuclear orphan receptor LXRα. Steroids 1999; 64:385-395.

Rubin CD. Treatment considerations in the management of age-related osteoporosis. The American J Medical Sciences 1999; 318 (3):158-170.

Russell DW. Oxysterol biosynthetic enzymes. Biochimica et Biophysica Acta 2000; 1529:126-135.

Sammons J, Ahmed N, Ei-Sheemy M, Hassan HT. The role of BMP-6, IL-6, and BMP-4 in mesenchymal stem cell-dependent bone development: effects on osteoblastic differentiation induced by parathyroid hormone and vitamin D3. Stem Cells and Development 2004, 13: 273-280.

Sanchez P, Hernandez AM, Stecca B, Kahler AJ, DeGueme AM, Barrett A, Beyna M, Datta MW, Datta S, Ruiz i Altaba A. Inhibition of prostate cancer proliferation by interference with Sonic Hedgehog-GLI1 signaling. Proc Natl Acad Sci U S A. Aug. 24, 2004;101(34):12561-6.

Schaafsma et al. 2001. Delay of natural bone loss by higher intake of specific minerals and vitamins. Crit Rev Food Sci Nutr 41:225-249.

Schroepfer GJ Jr. Oxysterols: modulators of cholesterol metabolism and other processes. Physiol Rev. Jan. 2000;80(1):361-554. Review.

Seo JB, Moon HM, Kim WS, Lee YS, Jeong HW, Yoo EJ, Ham J, Kang H, Park MG, Steffensen KR, Stulnig TM, Gustafsson JA, Park SD, Kim JB. Activated liver X receptors stimulate adipocyte differentiation through induction of peroxisome proliferator-activated receptor gamma expression. Mol Cell Biol. Apr. 2004;24(8):3430-44.

Shea CM, Edgar CM, Einhorn TA, Gerstenfeld LC. BMP treatment of C3H10T1/2 mesenchymal stem cells induces both chondrogenesis and osteogenesis. J Cell Biochem. Dec. 15, 2003;90(6):1112-27.

Shimaoka H, Dohi Y, Ohgushi H, Ikeuchi M, Okamoto M, Kudo A, Kirita T, Yonemasu K. Recombinant growth/differentiation factor-5 (GDF-5) stimulates osteogenic differentiation of marrow mesenchymal stem cells in porous hydroxyapatite ceramic. J Biomed Mater Res A. Jan. 1, 2004;68(1):168-76.

Shouhed D, Kha HT, Richardson JA, Amantea CM, Hahn TJ, Parhami F. Osteogenic oxysterols inhibit the adverse effects of oxidative stress on osteogenic differentiation of marrow stromal cells. J Cell Biochem 95:1276-1283; 2005.

Silva-Vargas V, Lo Celso C, Giangreco A, Ofstad T, Prowse DM, Braun KM, Watt FM. Beta-catenin and Hedgehog signal strength can specify number and location of hair follicles in adult epidermis without recruitment of bulge stem cells. Dev Cell. Jul. 2005;9(1):121-31.

Sohal RS, Mockett RJ, Orr WC. Mechanisms of aging: an appraisal of the oxidative stress hypothesis. Free Radic Biol Med. Sep. 1, 2002;33(5):575-86. Review.

Spinella-Jaegle S, Rawadi G, Kawai S, Gallea S, Faucheu C, Mollat P, Courtois B, Bergaud B, Ramez V, Blanchet AM, Adelmant G,

(56) References Cited

OTHER PUBLICATIONS

Baron R, Roman-Roman S. Sonic hedgehog increases the commitment of pluripotent mesenchymal cells into the osteoblastic lineage and abolishes adipocytic differentiation. J Cell Sci 114:2085-2094; 2001.
Spiro RC, Thompson AY, Poser JW. Spinal fusion with recombinant human growth and differentiation factor-5 combined with a mineralized collagen matrix. Anat Rec. Aug. 1, 2001;263(4):388-95.
Stein GS, Lian JB. Molecular mechanisms mediating proliferation/differentiation interrelationships during progressive development of the osteoblast phenotype. Endocrine Rev 14:424-442; 1993.
Stewart GA, Hoyne GF, Ahmad SA, Jarman E, Wallace WA, Harrison DJ, Haslett C, Lamb JR, Howie SE. Expression of the developmental Sonic hedgehog (Shh) signalling pathway is up-regulated in chronic lung fibrosis and the Shh receptor patchedl is present in circulating T lymphocytes. J Pathol 199:488-495; 2003.
St-Jacques B, Hammerschmidt M, McMahon P. Indian hedgehog signaling regulates proliferation and differentiation of chondrocytes and is essential for bone formation. Genes Dev 1999; 13:2072-2086.
Suh JM, Gao X, McKay J, McKay R, Salo Z, Graff JM. Hedgehog signaling plays a conserved role in inhibiting fat formation. Cell Metab. Jan. 2006;3(1):25-34.
Swarthout JT, D'Alonzo RC, Selvamurugan N, Partridge NC. Parathyroid hormone-dependent signaling pathways regulating genes in bone cells. Gene. Jan. 9, 2002;282(1-2):1-17. Review.
Taipale J, Beachy PA. The Hedgehog and Wnt signalling pathways in cancer. Nature. May 17, 2001;411(6835):349-54. Review.
Taylor FR, Kandutsch AA, Gayen AK, Nelson JA, Nelson SS, Phirwa S, Spencer TA. 24,25-Epoxysterol metabolism in cultured mammalian cells and repression of 3-hydroxy-3-methylglutaryl-CoA reductase. J Biol Chem. Nov. 15, 1986;261(32):15039-44.
Thies RS, Bauduy M, Ashton BA, Kurtzberg L, Wozney JM, Rosen V. Recombinant human bone morphogenetic protein-2 induces osteoblastic differentiation in W-20-17 stromal cells. Endocrinology 1992, 130(3): 1318-1324.
Väänänen HK. Mesenchymal stem cells. Ann Med. 2005;37(7):469-79. Review.
Valentin-Opran A, Wozney J, Csimma C, Lilly L, Riedel GE. Clinical evaluation of recombinant human bone morphogenetic protein-2. Clin Orthop & Related Res 2002; 305:110-120.
Velgova H, Cerny V, Sorm F, Slama K. Collect. Czech. Chem. Commun. 1969, 34: 3354-3375.
Vine DF, Mamo JCL, Beilin LJ, Mori TA, Croft KD. Dietary oxysterols are incorporated in plasma triglyceride-rich lipoproteins, incrase their susceptibility to oxidation and increase aortic cholesterol concentrations in rabbits. J Lipid Res 1998; 1995-2004.
Wang GJ, Cui Q, Balian G. The Nicolas Andry award. The pathogenesis and prevention of steroid-induced osteonecrosis. Clin Orthop Relat Res. Jan. 2000;(370):295-310.
Watson KE, Bostrom K, Ravindranath R, Lam T, Norton B, Demer LL. TGF-beta and 25-hydroxycholesterol stimulate osteoblast-like vascular cells to calcify. J Clin Invest 93:2106-2113; 1994.
Westendorf JJ, Kahler RA, Schroeder TM. nt signaling in osteoblasts and bone diseases. ene. Oct. 27, 2004;341:19-39. Review.
Wiersig JR, Waespe-Sarcevic N, Djerassi C. Stereospecific synthesis of the side chain of the steroidal plant sex hormone oogoniol. J. Org. Chem. 1979, 44(19): 3374-3382.
Woo BH, Fink BF, Page R, Schrier JA, Jo YW, Jiang G, DeLuca M, Vasconez HC, DeLuca PP Enhancement of bone growth by sustained delivery of recombinant human bone morphogenetic protein-2 in a polymeric matrix. Pharm Res 2001; 18:1747-1753.
Yamaguchi A, Komori T, Suda T. Regulation of osteoblast differentiation mediated by bone morphogenetic proteins, hedgehogs, and Cbfal. Endocrine Rev 2000; 21:393-411.
Yang D, Guo J, Divieti P, Bringhurst FR. Parathyroid hormone activates PKC-delta and regulates osteoblastic differentiation via a PLC-independent pathway. Bone. Apr. 2006;38(4):485-96. Epub Dec. 1, 2005.
Yang X, Karsenty G. Transcription factors in bone: developmental and pathological aspects. Trends Mol Med. Jul. 2002;8(7):340-5. Review.
Yoshida CA, Furuichi T, Fujita T, Fukuyama R, Kanatani N, Kobayashi S, Satake M, Takada K, Komori T. Core-binding factor beta interacts with Runx2 and is required for skeletal development. Nat Genet. Dec. 2002;32(4):633-8.
Yoshida K, Oida H, Kobayashi T, Maruyama T, Tanaka M, Katayama T, Yamaguchi K, Segi E, Tsuboyama T, Matsushita M, Ito K, Ito Y, Sugimoto Y, Ushikubi F, Ohuchida S, Kondo K, Nakamura T, Narumiya S. Stimulation of bone formation and prevention of bone loss by prostaglandin E EP4 receptor activation. Proc Natl Acad Sci U S A. Apr. 2, 2002;99(7):4580-5. Epub Mar. 26, 2002 (author typo: Yoshia).
Zanchetta P, Lagar de N, Guezennec J. Systematic effects on bone healing of a new hyaluronic acid-like bacterial exopolysaccharide. Calcif Tissue Int 2003; 73:232-236.
Zelcer N, Tontonz P. Liver X receptors as integrators of metabolic and inflammatory signaling. J Clin Invest 116:607-614; 2006.
Zhao M, Qiao M, Harris SE, Chen D, Oyajobi BO, Mundy GR. The zinc finger transcription factor Gli2 mediates bone morphogenetic protein 2 expression in osteoblasts in response to hedgehog signaling. Mol Cell Biol 26:6197-6208; 2006.
Zhao M, Qiao M, Oyajobi BO, Mundy GR, Chen D. E3 ubiquitin ligase Smurf1 mediates core-binding factor alpha1/Runx2 degradation and plays a specific role in osteoblast differentiation. J Biol Chem. Jul. 25, 2003;278(30):27939-44.
Ziros PG, Gil AP, Georgakopoulos T, Habeos I, Kletsas D, Basdra EK, Papavassiliou AG. The bone-specific transcriptional regulator Cbfal is a target of mechanical signals in osteoblastic cells. J Biol Chem. Jun. 28, 2002;277(26):23934-41.
ISR for PCT/US06/34374 mailed Jun. 16, 2008.
ISR for PCT/US07/05073 mailed Oct. 29, 2007.
ISR for PCT/US07/25833 mailed Sep. 11, 2008.
Corcoran RB and Scott MP. Oxysterols stimulate sonic hedgehog and proliferation of medulloblastoma cells. Proceedings of the National Academy of Sciences 2006, 103(22): 8408-8413.
Galus R et al.; Fluvastatin does not elevate periosteal osteogenesis induced by Moloney sarcoma virus (MSV) in mice. Pharmacol. Rep. 2006, 58(1): 60-66.
Izumo N et al.; Lipophilic statins can be osteogenic by promoting osteoblastic calcification in a Cbfa1- and BMP-2-independent manner. Methods and Findings in Experimental and Clinical Pharmacology 2001, 23(7): 389-394.
Lefevre A, Morera A-M, Saez Jm. Adrenal cholesterol-binding protein: properties and partial purification. FEBS Letters 1978, 89(2): 287-292.
Mundy et al.; Science 1999, 286: 1946-1949.
Parish et al.; Side-chain oxysterol regulation of 3-hydroxy-3-methylglutaryl coenzyme A reductase activity. Lipids 1995, 247-251.
Sang et al.; Ectopic overexpression of adipogenic transcription factors induces transdifferentiation of MC3T3-E1 osteoblasts. Biochemical and Biophysical Research Communications 2005, 327(3): 811-819.
Viccica et al.; Role of the cholesterol biosynthetic pathway in osteoblastic differentiation. J. Endocrinol. Invest. 2007, 30(6S): 8-12.
Office Action for U.S. Appl. No. 10/524,945 dated Mar. 23, 2009.
Office Action for U.S. Appl. No. 10/524,945 dated Jun. 11, 2008.
Office Action for U.S. Appl. No. 10/569,994 dated Jan. 2, 2009.
Office Action for U.S. Appl. No. 10/569,994 dated May 30, 2008.
Arnsdorf EJ et al.; Tissue Engineering: Part A (15) pp. 1-6 (2009).
Ayukawa, Y. et al., "Local application of statin promotes bone repair through the suppression of osteoclasts and the enhancement of osteoblasts at bone-healing sites in rats," Oral Surgery, Oral Medicine, Oral Pathology, Oral Radiology, and Endodontics, 107(3), pp. 336-342 (2009).
Beckers L. et al., "Disruption of hedgehog signaling in ApoE -/- mice reduces plasma lipid levels, but increases atherosclerosis due to enhanced lipid uptake by macrophages". J Pathol. Aug. 2007;212(4):420-8.
Bunta W. et al., Steroids 2004, 69: 483-493.

(56) References Cited

OTHER PUBLICATIONS

Chuu C. et al., "The liver X receptor agonist 10901317 acts as androgen receptor antagonist in human prostate cancer cells". Biochem Biophys Res Commun. Jun. 1, 2007;357(2):341-6. Epub Mar. 28, 2007.
Dwyer J et al., "Oxysterols are novel activators of the hedgehog signaling pathway in pluripotent mesenchymal cells". J Biol Chem 2007, 282: 8956-8968.
Kim, WK et al., "20(S)-hydroxycholesterol inhibits PPARgamma expression and adipogenic differentiation of bone marrow stromal cells through a hedgehog-dependent mechanism," J. Bone Miner Res., 22(11), pp. 1711-1719, (Nov. 2007).
Liu M. et al "The effect of simvastatin on the differentiation of marrow stromal cells from aging rats," Die Pharmazie 64(1), pp. 43-48 (2009).
Schambony A. et al., "Wnt-5A/Ror2 regulate expression of XPAPC through an alternative noncanonical signaling pathway". Dev Cell. May 2007;12(5):779-92.
Antonio, V. et al. "Oxysterol and 9-cis-retinoic acid stimulate the group IIA secretory phospholipase $A_2$ gene in rat smooth-muscle cells," Biochem J., vol. 376, pp. 351-360 (2003).
Burstein et al.,(1969) A Preliminary Report on the Intermediates in the Conversion in Vitro of Cholesterol to Pregnenolone in Adrenal Preparations. Steroids 14;(2):207-217.
Burstein, et al., (1969) Reactions of 20-Hydroxylated Steroids with Bovine Adrenal Tissue Preparations. Steroids 13;(3):399-412.
Cheng et al., (1977) Chemistry and Biochemistry of Chinese Drugs. Part 1. Sterol Derivatives Cytotoxic to Hepatoma Cells, Isolated from the Drug Bombyx cum Botryte. J. Chem. Res. (M) v. 9 pp. 2519-2521.
Cheng et al., (1977) Chemistry and Biochemistry of Chinese Drugs. Part 1. Sterol Derivatives Cytotoxic to Hepatoma Cells, Isolated from the Drug Bombyx cum Botryte. J. Chem. Res. (S), v. 9 p. 217.
Garrett et al., (2002) The role of statins as potential targets for bone formation. Arthritis Res., 4(4): 237-240.
Hummasti, S. et al., "Liver X receptors are regulators of adipocyte gene expression but not differentiation: identification of apoD as a direct target," Journal of Lipid Research, vol. 45, pp. 616-625 (2004).
ISR for PCT/US05/19870 mailed Oct. 14, 2005.
ISR from PCT/US2011/025064 mailed Nov. 9, 2011.
Kim, S. et al., "Identification of Two Brassinosteroids from the Cambial Region of Scots Pine (*Pinus silverstris*) by Gas Chromatography-Mass Spectometry, after Detection Using a Dwarf Rice Lamina Inclination Bioassay," vol. 94, pp. 1709-1713 (1990).
Pikuleva et al., (2001) Putative Helix F Contributes to Regioselectivity of Hydroxylation in Mitochondrial Cytochrome P450 27A1. Biochemistry, v. 40 pp. 7621-7629.
Shimizu et al., (1962) 20α, 22-Dihydroxycholesterol, an Intermediate in the Biosynthesis of Pregnenolone (3β-Hydroxypregn-5-en-20-one) from Cholesterol. J. Biol. Chem., 237;(3): 699-702.
Szendi et al., (2002) 1,5-Hydride shift in Wolff-Kishner reduction of (20R)-3β,20, 26-trihydroxy-27-norcholest-5-en-22-one; synthetic, quantum chemical, and NMR studies, Steroids 67;31-38.
Watanabe et al.,(2004) Stereoselective synthesis of (22R)- and (22S)-castasterone/ponasterone A hybrid compounds and evaluation of their molting hormone activity. Steroids 69: 483-493.
Yao, Z. et al., "22R-Hydroxycholesterol protects neuronal cells from β-amyloid-induced cytotoxicity by binding β-amyloid peptide," Journal of Neurochemistry vol. 83, pp. 1110-1119 (2002).
Zander et al., (1977) Chemistry and Biochemistry of Chinese Drugs. Part III. Mechanism of Action of Hydroxylated Sterols on Cultured Hepatoma Cells, J. Chem. Res. (M) v. 9, p. 2572.
Zander et al., (1977) Chemistry and Biochemistry of Chinese Drugs. Part III. Mechanism of Action of Hydroxylated Sterols on Cultured Hepatoma Cells, J. Chem. Res. (S) v. 9, p. 219.
Nagano et al., (1977) Chemistry and biochemistry of Chinese drugs, Part II—Hydroxylated sterols, cytotoxic towards cancerous cells: synthesis and testing. J. Chem. Res. (S) v. 9, p. 218.

Watanabe et al., "Stereoselective synthesis of (22R)- and (22S)-castasterone/ponasterone a hybrid compounds and evaluation of their molting hormone activity," Steroids 69 (2004), pp. 483-493.
Shan et al., "Chromatographic behavior of oxygenated derivatives of cholesterol," Steroids 68 (2003), pp. 221-233.
Szendi et al., "1,5-Hydride shift in Wolff-Kishner reduction of (20R)-3β,20, 26-trihydroxy-27-norcholest-5-en-22-one; synthetic, quantum chemical, and NMR studies,"Steroids 67 (2002), pp. 31-38.
Pikuleva et al., "Putative Helix F Contributes to Regioselectivity of Hydroxylation in Mitochondrial Cytochrome P450 27A1," Biochemistry, 40 (2001), pp. 7621-7629.
Burstein et al., "A Preliminary Report on the Intermediates in the Conversion in Vitro of Cholesterol to Pregnenolone in Adrenal Preparations," Steroids 14(2) (1969), pp. 207-217.
Burstein, et al., "Reactions of 20-Hydroxylated Steroids with Bovine Adrenal Tissue Preparations," Steroids 13(3) (1969), pp. 399-412.
Shimizu et al., "20α, 22-Dihydroxycholesterol, an Intermediate in the Biosynthesis of Pregnenolone (3β-Hydroxypregn-5-en-20-one) from Cholesterol,"J. Biol. Chem., 237(3) (1962), pp. 699-702.
Cheng et al., "Chemistry and Biochemistry of Chinese Drugs. Part 1. Sterol Derivatives Cytotoxic to Hepatoma Cells, Isolated from the Drug Bombyx cum Botryte," J. Chem. Res. (S) (1977), pp. 217.
Zander et al., "Chemistry and Biochemistry of Chinese Drugs. Part III. Mechanism of Action of Hydroxylated Sterols on Cultured Hepatoma Cells," J. Chem. Res. (S) (1977), pp. 219.
Garrett et al., "The role of statins as potential targets for bone formation," Arthritis Res. 4(4) (2002) pp. 237-240.
Albrektsson T., Johansson C. Osteoinduction, osteoconduction and osseointegration. 2001. Eur Spine J. 10:S96-S101.
Dimmeler et al. HMG-CoA reductase inhibitors (statins) increase endothelial progenitor cells via the PI 3-kinase/Akt pathway. 2001. Journal of Clin Invest. 108:(3): 391-397.
Rao et al. Lovastatin-mediated G1 arrest is through inhibition of the proteosome, independent of hydroxymethyl glutarl-CoA reductase. 1999. Proc. Natl. Acad. Sci. 96: 7797-7802.
Steitz et al. Smooth Muscle Cell Phenotypic Transition Associated With Calcification: Upregulation of Cbfa1 and Downregulation of Smooth Muscle Lineage Markers. 2001. Circ. Res. 89:1147-1154.
Tintut et al. Multilineage Potential of Cells From the Artery Wall. 2003. Circulation.108: 2505-2510.
Wada et al. Calcification of Vascular Smooth Muscle Cell Cultures: Inhibition by Osteopontin. 1999. Circ. Res. 84:166-178.
Wada et al. Lack of Positive Correlation Between Statin Ue and Bone Mineral Density in Japanese Subjects With Type 2 Diabetes. 2000. Arch Intern Med. 160:2865.
Wang et al. Lipid Clearing Agents in Steroid-Induces Osteoporosis. 1995. J Formos Med Assoc. 94(10): 589-592.
Office Action mailed Aug. 31, 2009 in related U.S. Appl. No. 10/569,994.
Choo et al., Otolaryngology Head Neck Surgery 1999, 120: 84-91.
Mezey et al., Oral Diseases 2009, Abstract.
Song et al., Chinese Journal of Reparative and Reconstructive Surgery 2002, 16: 384-387.
Yeh et al., Journal of Cell Biochemistry 2002, 87: 292-304.
Gregorio-King et al., Experimental Hematology, 2002, 30: 670-678.
International Search Report and Written Opinion issued in PCT Application No. PCT/US2013/032693 dated Jul. 18, 2013.
International Search Report issued in PCT Application No. PCT/US2014/036680 dated Sep. 10, 2014.
International Search Report and Written Opinion issued in PCT Application No. PCT/US2008/003493 dated Oct. 12, 2009.
International Search Report and Written Opinion issued in PCT Application No. PCT/US2010/041560 dated Aug. 31, 2010.
International Search Report and Written Opinion issued in PCT Application No. PCT/US2013/032650 dated Jul. 18, 2013.
International Search Report and Written Opinion issued in PCT Application No. PCT/US2013/039748 dated Sep. 25, 2013.
Liu et al., "Interferon-inducible cholesterol-25-hydroxylase broadly inhibits viral entry by production of 25-hydroxycholesterol," Immunity, Jan. 2013, vol. 38, pp. 92-105.
Nelson et al., Endocrinology, 2011, 152: 4691-4705.

(56) References Cited

OTHER PUBLICATIONS

Nishio et al., European Journal of Pharmacology, 1996, 301: 203-206.
Notice of Allowance issued in U.S. Appl. No. 10/524,945 dated Oct. 22, 2010.
Notice of Allowance issued in U.S. Appl. No. 12/520,281 dated May 12, 2011.
Office Action issued in U.S. Appl. No. 10/524,945 dated Dec. 9, 2009.
Office Action issued in U.S. Appl. No. 10/524,945 dated Jun. 28, 2010.
Office Action issued in U.S. Appl. No. 10/569,994 dated Feb. 13, 2014.
Office Action issued in U.S. Appl. No. 10/569,994 dated Oct. 8, 2014.
Office Action issued in U.S. Appl. No. 12/520,281 dated Nov. 1, 2010.
Office Action issued in U.S. Appl. No. 12/745,888 dated Jan. 8, 2013.
Office Action issued in U.S. Appl. No. 12/745,888 dated May 24, 2013.
Office Action issued in U.S. Appl. No. 13/579,278 dated Feb. 12, 2014.
Office Action issued in U.S. Appl. No. 13/579,278 dated Jun. 7, 2013.
Parish et al., Critical Reviews in Biochemistry & Molecular Biology, 1999, 34: 265-272.
Pezacki et al., "Transcriptional profiling of the effects of 25-hydroxycholesterol on human hepatocyte metabolism and the antiviral state it conveys against the hepatitis C virus," BMC Chemical Biology, 2009, vol. 9, i.2.
Rehman et al., "Antiviral drugs against hepatitus C virus," Genetic Vaccines and Therapy, 2011, vol. 9, i.11.
Restriction Requirement issued in U.S. Appl. No. 10/524,945 dated Feb. 28, 2008.
Restriction Requirement issued in U.S. Appl. No. 10/569,994 dated Feb. 7, 2008.
Restriction Requirement issued in U.S. Appl. No. 11/918,089 dated Jun. 7, 2011.
Restriction Requirement issued in U.S. Appl. No. 11/991,322 dated Jul. 8, 2011.
Restriction Requirement issued in U.S. Appl. No. 12/374,296 dated Nov. 14, 2011.
Restriction Requirement issued in U.S. Appl. No. 12/531,608 dated Sep. 27, 2010.
Restriction Requirement issued in U.S. Appl. No. 12/745,888 dated Nov. 2, 2012.
Restriction Requirement issued in U.S. Appl. No. 13/579,278 dated Oct. 11, 2012.
Richardson J. et al., "Oxysterol-induced osteoblastic differentiation of pluripotent mesenchymal cells is mediated through a PKCand PKA-dependent pathway," J. Cell. Biochem. 2007;100:1131-45.
Sagan et al., "The influence of cholesterol and lipid metabolism on host cell structure and hepatitis C virus replication," Biochemistry and Cell Biology, 2006, vol. 84, pp. 67-79.
Stappenbeck et al., Novel oxysterols activate the Hedgehod pathway and induce osteogenesis, Bioorganic & Medicinal Chemistry Letters, 22(18): 5893-5897, 2012 (Abstract Only).
Wolf et al., "A broad-spectrum antiviral targeting entry of enveloped viruses," Proceedings of the National Academy of Sciences, 2010, vol. 107, No. 7, pp. 3157-3162.
Yamaguchi et al., Clinical Calcium, 2002, 12: 39-43.
Yao et al., Neuroscience, 2007, 148:441-453.
Office Action issued in U.S. Appl. No. 10/569,994 dated Jan. 23, 2015.
Office Action issued in U.S. Appl. No. 12/745,888 dated Dec. 19, 2014.
Office Action issued in U.S. Appl. No. 13/579,278 dated May 14, 2015.
Jin et al., "The regulatory effect of human bone morphogenetic protein 7 gene transfer on the proliferation and differentiation of rabbit bone marrow mesenchymal stem cells," Zhongguo Yi Xue Ke XueYuan Xue Bao, 2003, 25(1): 22-25; Abstract.
Maxwell et al., "A recombinant bone growth factor and a mineralized collagen matrix (Healos/MP52) in threaded interbody fusion cages," Proceedings of the NASS 16th Annual Meeting/The Spine Journal, 2002, 2: 42S.
Nagahisa et al., "Acetylenic mechanism-based inhibitors of cholesterol side chain cleavage by cytochrome P-450scc," J. Biol. Chem. 1983, 258(11): 6721-6723.
Sampath et al., "Recombinant Human Osteogenic Protein-1 (hOP-1) Induced New Bone Formation in Vivo with a Specific Activity Comparable with Natural Bovine Osteogenic Protein and Stimulates Osteoblast Proliferation and Differentiation in Vitro," J. Biol. Chem., 1992, 267(28): 20352-20362.
Shimaoka et al., "Recombinant growth/differentiation factor-5 (GDF-5) stimulates osteogenic differentiation of marrow mesenchymal stem cells in porous hydroxyapatite ceramic," J. Biomed. Mater. Res., Online Nov. 28, 2003, 68A: 168-176.
Nagano, H. et al. (1977). "Chemistry and Biochemistry of Chinese Drugs. Part II. Hydroxylated Sterols, Cytotoxic towards Cancerous Cells: Synthesis and Testing," J. Chem. Research 9:218; 9:2522-2571. (English translation of the abstract only).
Yoon, S.T. et al. (Feb. 2002). "Osteoinductive molecules in orthopaedics: basic science and preclinical studies," 395:33-43.
International Search Report mailed on May 5, 2004, for PCT Application No. PCT/US03/027105, filed on Aug. 28, 2003, 1 page.
International Search Report mailed on Feb. 22, 2005, for PCT/US04/028162, filed Aug. 30, 2004, 4 pages.
Written Opinion mailed on Feb. 22, 2005, for PCT/US04/028162, filed Aug. 30, 2004, 5 pages.
International Search Report mailed on Jul. 7, 2008, for PCT/US06/012902, filed on Apr. 7, 2006, 1 page.
Written Opinion mailed on Jul. 7, 2008, for PCT/US06/012902, filed on Apr. 7, 2006, 3 pages.
International Search Report mailed on Jun. 16, 2008, for PCT/US06/34374, filed on Sep. 5, 2006, 1 page.
Written Opinion mailed on Jun. 16, 2008, for PCT/US06/34374, filed on Sep. 5, 2006, 3 pages.
International Search Report mailed on Sep. 16, 2008, for PCT/US07/016309, filed on Jul. 19, 2007, 1 page.
Written Opinion mailed on Sep. 16, 2008, for PCT/US07/016309, filed on Jul. 19, 2007, 4 pages.
International Search Report mailed on Oct. 29, 2007, for PCT/US07/05073, filed on Feb. 27, 2007, 2 pages.
Written Opinion mailed on Oct. 29, 2007, for PCT/US07/05073, filed on Feb. 27, 2007, 5 pages.
International Search Report mailed on Sep. 11, 2008, for PCT/US07/25833, filed on Dec. 19, 2007, 1 page.
Written Opinion mailed on Sep. 11, 2008, for PCT/US07/25833, filed on Dec. 19, 2007, 4 pages.
International Search Report mailed on Apr. 8, 2009, for PCT/US08/013319, filed on Dec. 3, 2008, 3 pages.
Written Opinion mailed on Apr. 8, 2009, for PCT/US08/013319, filed on Dec. 3, 2008, 6 pages.
Abe et al., "Effects of bisphosphonates on osteoclastogenesis in RAW264.7 cells," 2012, International Journal of Molecular Medicine 29.6: 1007-1015.
Acsadi et al., "Human dystrophin expression in mdx mice after intramuscular injection of DNA constructs," 1991, Nature 352: 815-818.
Albers M. et al., "A novel principle for partial agonism of liver X receptor ligands," 2006, Journal of Biological Chemistry 281(8):4920-4930.
Amantea et al., "Oxysterol-induced osteogenic differentiation of marrow stromal cells is regulated by Dkk-1 inhibitable and PI3-Kinase mediated signaling," 2008, Journal of Cellular Biochemistry 105(2): 424-436.
Arns et al., "Design and synthesis of novel bone-targeting dual-action pro-drugs for the teament and reversal of osteoporosis," 2012, Bioorganic and Medicinal Chemistry. 20(6):2131-2140.

(56) References Cited

OTHER PUBLICATIONS

Aspray et al., "Treatment of osteoporosis in women intolerant of oral bisphosphonates," 2012, *Maturitas*, 71:76-78.
Bailey et al., "Sonic Hedgehog paracrine signaling regulates metastasis and lymphangiogenesis in pancreatic cancer," 2009, *Oncogene* 28(40): 3513-3525.
Barginear et al., "The hedgehog pathway as a therapeutic target for treatment of breast cancer," 2009, *Breast cancer research and treatment* 116(2):239-246.
Bauss et al., "Effect of 17B-estradiol-biphosphonate conjugates, potentiial bone-seeking estrogen pro-drugs, on 17B-estradiol serum kinetics and bone mass in rats," 1996, *Calcified Tissue International* 59: 168-173.
Black et al., "Continuing bisphosphonate treatment for osteoporosis—for whom and for how long?" 2012, *New England Journal of Medicine* 366(22), 2051-2053.
Brewer et al., "Current and future treatment options in osteoporosis," 2011, *European Journal of Clinical Pharmacology* 67(4): 321-331.
Bruice, T. C. et al. *Bioorganic Mechanisms*, vol. 1, W. A. Benjamin, New York, 1966, 1-258. Table of Contents Provided Only.
Canalis, "Update in new anabolic therapies for osteoporosis," 2010, *The Journal of Clinical Endocrinology and Metabolism* 95(4), 1496-1504.
Chisholm et al., "The LXR ligand T0901317 induces severe lipogenesis in the db/db diabetic mouse," 2003, *Journal of Lipid Research* 44(11):2039-2048; 2003.
Cline et al., "Perspectives for gene therapy: inserting new genetic information into mammalian cells by physical techniques and viral vectors," 1985, *Pharmacology and therapeutics* 29(1):69-92.
Cosman. "Anabolic and Atiresorptive Therapy for Osteoporosis: Combination and Sequential Approaches," 2014, *Current osteoporosis reports* 12(4):385-395.
Dimitriou et al., "Bone regeneration: current concepts and future directions," 2011, *BMC Medicine* 9(1):1-10.
Dlugosz et al., "Following the Hedgehog to new cancer therapies," 2009, *New England Journal of Medicine* 361(12):1202-1205.
Ebetino et al., "The relationship between the chemistry and biological activity of the bisphosphonates," 2011, *Bone* 49(1):20-33.
Feldmann et al., "Blockade of Hedgehog signaling inhibits pancreatic cancer invasion and metastasis: A new paradigm for combination therapy in solid tumors," 2007, *Cancer Research* 67(5):2187-2196.
Fievet et al., "Liver X receptor modulators: Effects on lipid metabolism and potential use in the treatment of atherosclerosis," 2009, *Biochemical Pharmacology* 77(8):1316-1327.
Forman et al., "The orphan nuclear receptor LXRa is positively and negatively regulated by distinct products of mevalonate metabolism," 1997, *Proceedings of the National Academy of Sciences of the United States of America* 94(20), pp. 10588-10593.
Friedmann et al., "Progress toward human gene therapy," 1989, *Science* 244(4910):1275-1281.
Geyeregger et al., "Liver x receptors interfere with cytokine-induced proliferation and cell survival in normal and leukemic lymphocytes," 2009, *Journal of Leukocyte Biology* 86:1039-1048.
Gill et al., "Sterol regulators of cholesterol homeostasis and beyond: The oxysterol hypothesis revisited and revised," 2008, *Progress in Lipid Research* 47(6):391-404.
Hilton M. et al., "Ihh controls cartilage development by antagonizing Gli3, but requires additional effectors to regulate osteoblast and vascular development," 2005, *Development* 132(19):4339-4351.
Hirotsu et al., "Smoothened as a new therapeutic target for human osteosarcoma," 2010, *Molecular Cancer* 9(1):1-14.
Hochman E. et al., "Molecular pathways regulating pro-migratory effects of hedgehog signaling," 2006, *Journal of Biological Chemistry* 281(45):33860-33870.
Hokugo et al., "A novel oxysterol promotes bone regenration in rabbit cranial bone defects," 2013, *Journal of Tissue Engineering and Regenerative Medicine*.

International Search Report and Written Opinion issued in PCT/US2015/028917 dated Jul. 27, 2015.
Jahnke et al., "An in vitro Assay to Measure Targeted Drug Delivery to Bone Mineral," 2010, *ChemMedChem* 5(5):770-776.
Jiang et al., "Hedgehog signaling in development and cancer," 2008, *Developmental Cell* 15(6):801-812.
Johnson et al., "Novel oxysteols have pro-osteogenic and anti-adipogenic effects in vitro and induce spinal fusion in vivo," 2011, *Journal of Cellular Biochemistry* 112(6): 1673-1684.
Johnson et al., "Human bone morphogenetic protein allografting for reconstruction of femoral nonunion," 2000, *Clinical Orthopaedics and Related Research* 371:61-74.
Joseph S., et al., "Synthetic LXR ligand inhibits the development of atherosclerosis in mice," 2002, *Proceedings of the National Academy of Sciences* 99(11):7604-7609.
Kaneko et al., "Induction of Intestinal ATP-binding cassette transporters by a phytosterol-derived liver x receptor agonist," 2003, *The Journal of Biological Chemistry* 278(38)36091-36098.
Kim et al., "Hedgehog signaling and osteogenic differentiation in multioptent bone marrow stromal cells are inhibited by oxidative stress," 2010, *Journal of Biological Chemistry* 111(5):1199-1209.
Kim et al., "20(S)-hydroxycholesterol inhibits PPARgamma expression and adipogenic differentiation of bone marrow stromal cells through a Hedgehog-dependent mechanism," 2007, *Journal of Bone and Mineral Research* 22(11):1711-9.
Koreeda et al., "Chirality transfer in stereoselective synthesis. A highly stereocontrolled synthesis of 22-hydroxylated steroid side chains via the [2,3]-Wittig rearrangmeent," 1986, *Journal of Organic Chemistry* 51(21):4090-4092.
Larsson et al. "Kinetics of GI progression in 3T6 and SV-3T3 cells following treatment by 25-hydroxycholesterol." 1986, *Cancer Research* 46(3):1233-1238.
Liao X. et al., "Aberrant activation of hedgehog signaling pathway in ovarian cancers: effect on prognosis, cell invasion and differentiation," 2009, *Carcinogenesis* 30(1):131-140.
Lin, "Bisphosphonates: A review of their pharmacokinetic properties," 1996, *Bone* 18(2):75-85.
Lin et al., "Pharmacokinetics of alendronate: an overview," 1999, *International journal of clinical practice. Supplement* 101:18-26.
Luhmann et al., "Bone targeting for the treatment of osteoporosis," 2012, *Journal of Controlled Release* 161(2):198-213.
Lyritis et al., "Bone anabolic versus bone anticatabolic treatment of postmenopausl osteoporosis," 2010, Annals of the New York Academy of Sciences 1205:277-283.
Mimaki et al., "Lipid and steroidal constituents of *Lilium auratum* var. *platyphyllum* and *L. tenuifolium*," 1989, *Phytochemistry* 28(12), 3453-3458.
Montgomery et al., "A Novel Osteogenic Oxysterol Compound for Therapeutic Development to Promote Bone Growth: Activation of Hedgehog Signaling and Osteogenesis through Smoothened Binding," 2014, *Journal of Bone and Mineral Research* 29(8):1872-1885).
Morioka et al., "Design, synthesis and biological evaluation of novel estradio-biphosphonate conjugates as bone-specific estrogens," 2010, *Bioorganic and Medicinal Chemistry* 18(3):1143-1148.
Muschitz et al., "Antiesorptives overlapping ongoing teriparatide treatment result in additional increases in bone mineral density," 2013, *Journal of Bone and Mineral Research* 28(1):196-205.
Myers et al., "Hedgehog pathway modulation by multiple lipid binding sites on the smoothened effector of signal response," 2013, *Developmental Cell* 26(4):346-357.
Nachtergaele et al., "Oxysterols are allosteric activators of the oncoprotein Smoothened," 2012, *Nature Chemical Biology* 8(2):211-220.
Nachtergaele et al., "Structure and function of the Smoothened extracellular domain in vertebrate Hedgehog signaling," 2013, *eLife* 2:e01340.
Nasim et al., "3-O-Phosphate ester conjugates of 17-beta-O-1,3,5(10)-estratriene as novel bone-targeting agents," 2010, *Bioorganic and Medicinal Chemistry Letters* 20:7450-7453.

(56) References Cited

OTHER PUBLICATIONS

Nedelcu et al., "Oxysterol binding to the extracellular domain of Smoothened in Hedgehod signaling," 2013, *Nature chemical biology* 9(9):557-564.

Nickolson et al., "Stereospecific synthesis of (20S,22R)-17α,20,22-trihydroxycholesterol and (20S,22S)-17a,20,22-trihydroxycholesterol," 1972, *Journal of Organic Chemistry* 37(13), 2119-2127.

Parhami et al., "Lipid oxidation products have opposite effects on calcifying vascular cell and bone cell differentiation. A possible explanation for the paradox of arterial calcification in osteoporotic patients," 1997, *Arteriosclerosis, thrombosis, and vascular biology* 17(4):680-687.

Peacock C. et al., "Hedgehog signaling maintains a tumor stem cell compartment in multiple myeloma," 2007, *Proceedings of the National Academy of Sciences* 104(10):4048-4053.

Peng et al., "Antiatherosclerotic effects of a novel synthetic tissue-selective steroidal liver X receptor agonist in low-density lipoprotein receptor-deficient mice," 2008, *Journal of Pharmacology and Experimental Therapeutics* 327(2):332-342.

Phelan C. et al., "Selective partial agonism of liver X receptor a is related to differential corepressor recruitement," 2008, *Molecular Endocrinology* 22(10): 2241-2249.

Porter J. et al., "Cholesterol modification of Hedgehog signaling proteins in animal development," 1996, *Science* 274:255-259.

Rachner et al., "New Horizons in Osteoporosis," 2011, *Lancet* 377(9773):1276-1287.

Raghow et al., "SREBPs: the crossroads of physiological and pathological lipid homeostasis," 2008, *Trends in Endocrinology and Metabolism* 19(2):65-73.

Raisz et al., "Pathgenesis of osteoporosis: concepts, conflicts, and prospects," 2005, *Journal of Clinical Investigation* 115(12):3318-3325.

Reszka et al., "Mechanism of action of bisphosphonates," 2003, *Current Osteoporosis Reports* 1(2):45-52.

Roodman et al., "Bone Building with bortezomib," 2008, *Journal of Clinical Investigation* 118(2):462-464.

Rubin et al., "Targeting the Hedgehog pathway in cancer," 2006, *Nature reviews Drug discovery* 5(12):1026-1033.

Rudin et al., Treatment of medulloblatoma with Hedgehog pathway inhibitor GDC-0449, 2009, *New England Journal of Medicine* 361(12):1173-1178.

Sagan et al., "The influence of cholesterol and lipid metabolism on host cell structure and hepatitis C virus replication," 2006, *Biochemistry and Cell Biology* 84(1):67-79.

Schambony A. et al., "Wnt-5A/Ror2 regulate expression of XPAPC through an alternative noncanonical signaling pathway," 2007, *Developmental Cell* 12(5):779-92.

Schmidt et al., "A 15-ketosterol is a liver x receptor ligand that suppresses sterol-responsive element binding proteing-2 activity," 2006, *Journal of Lipid Research* 47:1037-1044.

Scott et al., "Comparison of a novel oxsterol molecule and rhBMP2 fusion rates in a rabbit posterolateral lumbar spine model," 2015, *The Spine Journal* 15:733-742.

Semb, "Isozymes of bone esterases," 1970, *Calcified Tissue Research* 6(1):77-80.

Shaw et al., "The Sonic Hedgehog pathway stimulates prostate tumor growth by paracrine signaling and recapitulates embryonic gene expression in tumor myofibroblasts". 2009, *Oncogene* 28(50):4480-4490.

Sheikh et al., "Mass spectometry in structural and stereochemical problems. CCXXX Preparation of 5a, 20a and 5a, 17a, 20a-cholestane-3b, 6a-diol. Electron impact induced framentation of steroidal D 17(20), D 20(21) and D 20(22) olefins," 1973, *Journal of Organic Chemistry* 38(20):3545-3553.

Shinoda et al., "HMG-CoA Reductase Inhibitor, Acceleration of Bone Formation with Satin," 2000, *Pharmacia* 649-650.

Silva et al., "New approaches to the treatment of osteoporosis," 2011, *Annual Review of Medicine* 62:307-322.

Sottero et al., "Cholesterol oxidation products and disease: an emerging topic of interest in medicinal chemistry," 2009, *Current Medicinal Chemistry* 16(6):685-705.

Sugano et al., "Identification of intermediates in the conversion of cholesterol to pregnenolone with a reconstituted cytochrome P-450sec system: accumulation of the intermediate modulated by the adrenodoxin level," 1996, *Journal of Biochemistry* 120(4), pp. 780-787.

Supplementary European Search Report issued in EP 03749213.9 dated May 14, 2009.

Supplementary European Search Report issued in EP 06824888.9 dated Jun. 24, 2009.

Sydykov et al., "Synthesis of (20S)-propargyl-5-pregnene-3b,20-diol and its use in the preparation of C27-steroids with an oxidized side chain," 1976, *Bioorganicheskaya Khimiya* 2(11):1531-1537. English Abstract Provided Only.

Sydykov et al, "Partial synthesis of 20(R),22(R)-D 5-cholestene-3b,20,22-triol," 1977, *Izvestiya Akademiii Nauk SSSR, Seriya Khimicheskaya* 1:191-194.

Ta et al., "Osteosarcoma treatment: state of the art," 2009, *Cancer Metastasis Reviews* 28(1-2):247-263.

Teplyuk et al., "The osteogenic transcription factor runx2 controls genes involved in sterol/steroid metabolism, including CYP11A1 in osteoblasts,"2009, *Molecular Endocrinology* 23(6):849-861.

Thayer et al., "Hedgehog is an early and late mediator of pancreatic cancer tumorigenesis," 2003, *Nature* 425(6960):851-856.

Vedin et al., "The oxysterol receptor LXR inhibits proliferation of human breast cancer cells," 2009, *Carcinogenesis* 30(4):575-579.

Vescini et al., "PTH 1-84: bone rebuilding as a target for the therapy of severe osteoporosis." 2012, *Clinical Cases in Mineral and Bone Metabolism* 9(1):31-36.

Von Hoff et al., "Inhibition of the Hedgehog pathway in advanced basal-cell carcinoma," 2009, *New England Journal of Medicine* 361:1164-1172.

Wang et al., "Structure of the human smoothened receptor 7TM bound to an antitumour agent," 2013, *Nature* 497(7449):338-343.

Chen, J.K. et al. (Oct. 22, 2009). "Small molecule modulation of Smoothened activity," *Proc Natl Acad Sci USA* 99(22):14071-14076.

Yauch, R.L. et al. (Sep. 18, 2008, e-published Aug. 27, 2008). "A paracrine requirement for hedgehog signalling in cancer," *Nature* 455(7211):406-410.

Correa, C. (Jan. 2007). "Guidelines for the Examination of Pharmaceutical Patents: Developing a Public Health Perspective," WHO-ICTSD, UNCTAD, 65 pages.

Guan, Y. et al. (Jul.-Aug. 2000). "Synthesis of compound libraries based on 3,4-diaminocyclopentanol scaffolds," *J Comb Chem* 2(4):297-300.

Khosla, S. et al. (Jul. 2012, e-published Apr. 20, 2012). "Benefits and risks of bisphosphonate therapy for osteoporosis," *J Clin Endocrinol Metab* 97(7):2272-2282.

Neale, J.R. et al. (Feb. 1, 2009, e-published Dec. 24, 2008). "Bone selective effect of an estradiol conjugate with a novel tetracycline-derived bone-targeting agent," *Bioorg Med Chem Lett* 9(3):680-683.

Petrova, N.S. et al. (Mar. 2012, e-published Nov. 10, 2011). "Carrier-free cellular uptake and the gene-silencing activity of the lipophilic siRNAs is strongly affected by the length of the linker between siRNA and lipophilic group," *Nucleic Acid Res* 40(5):2330-2344.

\* cited by examiner

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 1
agctgcaatc accaaccaca gca                                           23

<210> SEQ ID NO 2
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 2
aaaatgaatt caacaactcc gccccattga c                                  31

<210> SEQ ID NO 3
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 3
cccgcgcggc cgccgactac gacctaattc ctgc                               34

<210> SEQ ID NO 4
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 4 gaacaccca                                                            9
```

OXYSTEROL COMPOUNDS AND THE HEDGEHOG PATHWAY

This application claims the benefit of the filing dates of U.S. provisional applications 60/776,990, filed Feb. 27, 2006; 60/802,737, filed May 22, 2005; and 60/809,736, filed May 31, 2006; all of which are incorporated by reference herein in their entireties.

REFERENCE TO A "SEQUENCE LISTING," A TABLE, OR A COMPUTER PROGRAM LISTING APPENDIX SUBMITTED AS AN ASCII FILE

The Sequence Listing written in file 48539-530N01US_ST25, created Aug. 8, 2016, 1,331 bytes, machine format IBM-PC, MS Windows operating system, is hereby incorporated by reference.

Aspects of the invention were made with U.S. government support provided by NIH/NIA grant number IP60-AG10415 and NIH/NIAMS grant number R01-AR050426. The government has certain rights in the invention.

BACKGROUND INFORMATION

Oxysterols form a large family of oxygenated derivatives of cholesterol that are present in the circulation, and in human and animal tissues. Oxysterols that have been identified in human plasma to date include 7α-hydroxycholesterol, 24S-hydroxycholesterol, and 4α- and 4β-hydroxycholesterol, which are present at concentrations ranging from 5-500 ng/ml. These oxysterols have a variety of half-lives in circulation ranging from 0.5-60 hours, and their levels can be altered by aging, drug interventions, and disease processes. Oxysterols may be formed either by autoxidation, as a secondary byproduct of lipid peroxidation, or by the action of specific monooxygenases, most of which are members of the cytochrome P450 family of enzymes. Examples of these enzymes are cholesterol 7α-hydroxylase (CYP7A1) that forms 7α-hydroxycholesterol, cholesterol 25-hydroxylase that forms 25-hydroxycholesterol, cholesterol 24S-hydroxylase (CYP46) that forms 24S-hydroxycholesterol, and others. In addition, oxysterols may be derived from the diet. Cytochrome P450 enzymes are also involved in the further oxidation of oxysterols and their metabolism into active or inactive metabolites that leads to their eventual removal from the system. Since certain oxysterols have potent effects on cholesterol metabolism, their involvement in that process has been widely studied in recent years. In addition, the presence of oxysterols in atherosclerotic lesions has prompted studies of their potential role in the pathogenesis of this disorder. A role for specific oxysterols has been implicated in various physiologic processes including cellular differentiation, inflammation, apoptosis, and steroid production. Moreover, due to the abundance of cholesterol in living organisms, the prooxidant nature of our environment, and the multitude of enzymatic and non-enzymatic pathways for their production, it would not be surprising to find that oxysterols play additional, as yet unidentified, roles in biological systems.

Recently, several reports have noted the possible role of oxysterols in cellular differentiation. Specific oxysterols induce the differentiation of human keratinocytes in vitro, while monocyte differentiation can be induced by the oxysterol 7-ketocholesterol. Our previous reports have shown that specific oxysterols induce the differentiation of pluripotent mesenchymal cells into osteoblastic cells, while inhibiting their differentiation into adipocytes. Differentiation of keratinocytes by oxysterols is mediated by the nuclear hormone receptor, liver X receptor β (LXRβ). LXRα and LXRβ, initially identified as orphan nuclear receptors, act as receptors for oxysterols. However many of the effects of oxysterols are mediated by LXR-independent mechanisms. These include their effects on mesenchymal cells, since activation of LXR by specific LXR ligands inhibited, rather than stimulated, the osteogenic differentiation of mesenchymal cells. Furthermore, MSC derived from LXR null mice were able to respond to osteogenic oxysterols as well as their wild type counterparts. Additional oxysterol binding proteins have been reported that can regulate the activity of signaling molecules such as mitogen-activated protein kinase (MAPK).

Hedgehog molecules have been shown to play key roles in a variety of processes including tissue patterning, mitogenesis, morphogenesis, cellular differentiation and embryonic developments. In addition to its role in embryonic development, hedgehog signaling plays a crucial role in postnatal development and maintenance of tissue/organ integrity and function. Studies using genetically engineered mice have demonstrated that hedgehog signaling is important during skeletogenesis as well as in the development of osteoblasts in vitro and in vivo. In addition to playing a pro-osteogenic role, hedgehog signaling also inhibits adipogenesis when applied to pluripotent mesenchymal cells, C3H-10T ½.

Hedgehog signaling involves a very complex network of signaling molecules that includes plasma membrane proteins, kinases, phosphatases, and factors that facilitate the shuffling and distribution of hedgehog molecules. Production of hedgehog molecules from a subset of producing/signaling cells involves its synthesis, autoprocessing and lipid modification. Lipid modification of hedgehog, which appears to be essential for its functionality, involves the addition of a cholesterol molecule to the C-terminal domain of the auto-cleaved hedgehog molecule and palmitoylation at its N-terminal domain. Additional accessory factors help shuttle hedgehog molecules to the plasma membrane of the signaling cells, release them into the extracellular environment, and transport them to the responding cells.

In the absence of hedgehog molecules, Patched (Ptch), present on the plasma membrane of the responding cells, keeps hedgehog signaling in a silent mode by inhibiting the activity of another plasma membrane associated signal transducer molecule, Smoothened (Smo). In the presence of hedgehog, the inhibition of Smo by Ptch is alleviated and Smo transduces the signal for the regulation of transcription of hedgehog-regulated genes. This transcriptional regulation in part involves the Ci/Gli transcription factors that enter the nucleus from the cytoplasm after a very intricate interaction between the members of a complex of accessory molecules that regulate Gli and its conversion from a 75 kd transcriptional repressor to a 155 kd transcriptional activator. The details of this highly complex signaling network have been extensively reviewed. (Cohen (2003) *Am J Med Gen* 123A. 5-28; Mullor et al. (2002) *Trends Cell Bio* 12, 562-569).

or 200 ng/ml Sonic Hedgehog (Shh) were analyzed for induction of the Hh target genes Gli-1 (a) and Patched (Ptch) (b). Data from a representative experiment are reported as the mean of quadruplicate determination±s.d. ($p<0.005$ for C vs. SS and Shh at all time points for Gli-1 and Ptch). (c) Hh pathway activation as measured by Gli-dependent luciferase reporter (Gli-Luc) activity in M2 cells. Cells were pre-treated for 2 hours with 4 µM cyclopamine (Cyc) or dimethylsulfoxide (DMSO) vehicle, followed by 48 hours of treatment with control vehicle (C), 5 µM SS or 200 ng/ml Shh ($p<0.002$ for C vs. SS and Shh Gli-Luc, and for SS and Shh each with vs. without Cyc). (d) Non-osteoinductive oxysterols, 7-α-hydroxycholesterol (7-alpha-HC) and 7-keto-hydroxycholesterol (7-keto-HC), each used at 5 µM, as well as the Liver X Receptor (LXR) agonist TO-901317 (TO) were assessed in parallel with 5 µM of osteoinductive oxysterols SS, and 200 ng/ml Shh for induction of Gli-luc reporter activity.

FIG. 3 shows that the Hedgehog pathway inhibitor, cyclopamine, inhibits oxysterol-induced osteoblastic differentiation. (a) Alkaline phosphatase activity assay in M2 cells pre-treated with various doses of cyclopamine (Cyc) or DMSO vehicle for 2 hours followed by treatment for 3 days with the oxysterol combination, SS. Results from a representative experiment are reported as the mean of quadruplicate determinations±s.d. and normalized to protein concentrations. ($<0.001$ for C vs. SS and SS vs SS+Cyc at all concentrations). (b) EMSA analysis for Runx2 DNA Binding Activity in M2 cells treated for 4 days with control vehicle or 5 µM SS following pre-treatment with 4 µM Cyc or DMSO vehicle for 2 hours. The shifted band (arrow) was previously characterized as Runx2 by supershift analysis and competition studies. (c) Analysis of osteocalcin (OCN) mRNA expression by Northern Blotting. M2 cells were pre-treated with 4 µM Cyc for 2 hours followed by treatment with control vehicle (C) or 5 µM SS for 8 days. Blots were quantitated by phosphorimaging and OCN expression was normalized to 18S rRNA levels. (d) $^{45}$Ca incorporation assay was used to measure mineralization in M2 cells pre-treated with 4 µM Cyc or DMSO vehicle for 2 hours, and then treated with 5 µM SS for 14 days. Data from a representative experiment are reported as the mean of quadruplicate determinations±s.d. and normalized to protein concentrations. $p<0.001$ for C vs. SS and SS vs. SS+Cyc at 0.5 µM and above).

Figure 4:
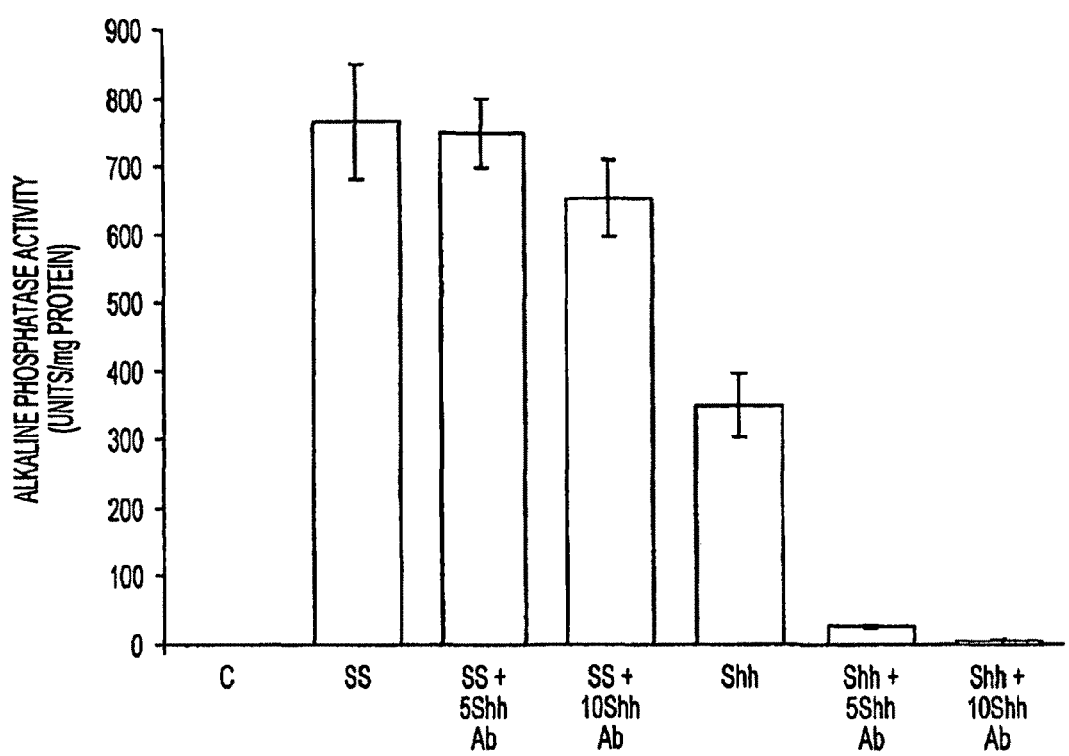

FIG. 4 shows the effect of Shh neutralizing antibody on oxysterol- and Shh-induced ALP activity. M2 cells were treated with control vehicle (C), 5 µM SS, or 200 ng/ml Shh in the absence or presence of 5 or 10 µg/ml of Shh neutralizing antibody (Ab). Cells were cultured for 3 days and the extracts were analyzed for alkaline phosphatase activity. Results from a representative experiment are reported as the mean of quadruplicate determinations±s.d. and normalized to protein concentrations ($p<0.005$ for C vs. SS and Shh; $p<0.001$ for Shh vs. Shh+Ab at both concentrations; $p=0.8$ for SS vs. SS+Ab at both concentrations).

FIG. 5 shows Hedgehog pathway activation in mouse embryonic fibroblasts. (a) C3H10T½ cells were treated with control vehicle or 5 uM SS with and without pre-treatment with cyclopamine (Cyc). Samples were analyzed for alkaline phosphatase activity after two days ($p<0.001$ for Control vs. SS, and for SS vs. SS+Cyc). (b) Oxysterol-induced Hh pathway activation in C3H10T½ cells as measured by Gli-luc reporter assay. Cells were treated with control vehicle or 5 µM SS with or without pre-treatment with 4 µM Cyc ($p<0.001$ for Control vs. SS, and for SS vs. SS+Cyc Gli-luc). (c) Gli-dependent luciferase reporter assay in Smo−/− MEFs. Cells were transfected with or without Smoothened (Smo) expression vector and assessed for responsiveness to control vehicle, 5 µM SS or conditioned medium from ShhN overexpressing cells (ShhN-CM) ($p<0.001$ for control vs. ShhN-CM and SS with Smo expression vector) (d) Alkaline phosphatase assay of Smo−/− Mouse Embryonic Fibroblasts (MEFs) treated with various concentrations of SS or with 50 ng/ml Bone Morphogenic Protein 7 (BMP-7) for two days ($p<0.001$ for control vs. BMP-7). (e) Gli dependent luciferase reporter assay in Ptch−/− MEFs. Cells were transfected with or without Ptch expression vector and analyzed for their response to control vehicle, 5 µM SS or conditioned medium from ShhN overexpressing cells (ShhN-CM) ($p<0.001$ for control vs. SS and Shh-CM with Ptch expression vector). (f) Cyc titration assay in Ptch−/− MEFs in the presence or absence of oxysterols. Similar concentrations of cyclopamine are required to inhibit Gli-dependent luciferase expression in Ptch−/− MEFs in the absence or presence of 5 µM SS, as demonstrated by the percentage of maximum Hh pathway activation after 48 hours of treatment. Data from a representative experiment are reported as mean±s.d. of triplicate samples. (g) 200 nM KAAD-cyclopamine blocks the binding of BODIPY-cyclopamine to Smo-expressing HEK293S cells, but 5 µM of 20S or 22S, alone or in combination, are unable to reduce BODIPY-cyclopamine binding. Nonspecific binding as defined by cellular BODIPY-cyclopamine levels in the absence of Smo expression is indicated by the dashed line.

FIG. 6 shows the effect of protein kinase C inhibition on oxysterol-induced expression of hedgehog target genes. (a, b) M2 cells were pretreated for 2 hours with control vehicle or rottlerin (Rot) at the concentrations indicated (µM). Next, oxysterol combination SS or control vehicle (C) were added and after 24 hours of treatments, RNA was isolated and analyzed by Q-RT-PCR for Gli-1 (a) and Ptch (b) expression. Data from a representative experiment are reported as the mean of triplicate determination±s.d. ($p<0.001$, for C vs. SS and for SS vs. SS+Rot at all Rot concentrations for both Gli-1 and Ptch expression, except for SS vs. SS+Rot1 Gli1 expression where $p<0.01$.) Rot alone at all concentrations tested had no significant effect on gene expression (data not shown). (c, d) M2 cells were pretreated overnight with 1 µM PMA or control vehicle followed by the addition of SS or control vehicle (C). After 24 hours of treatments, Gli-1 (c) and Ptch (d) mRNA expression was analyzed by Q-RT-PCR. Data from a representative experiment are reported as the mean of triplicate determinations±s.d. ($p<0.001$ for C vs. SS and for SS vs. PMA+SS for both Gli-1 and Ptch expression).

Figure 7:
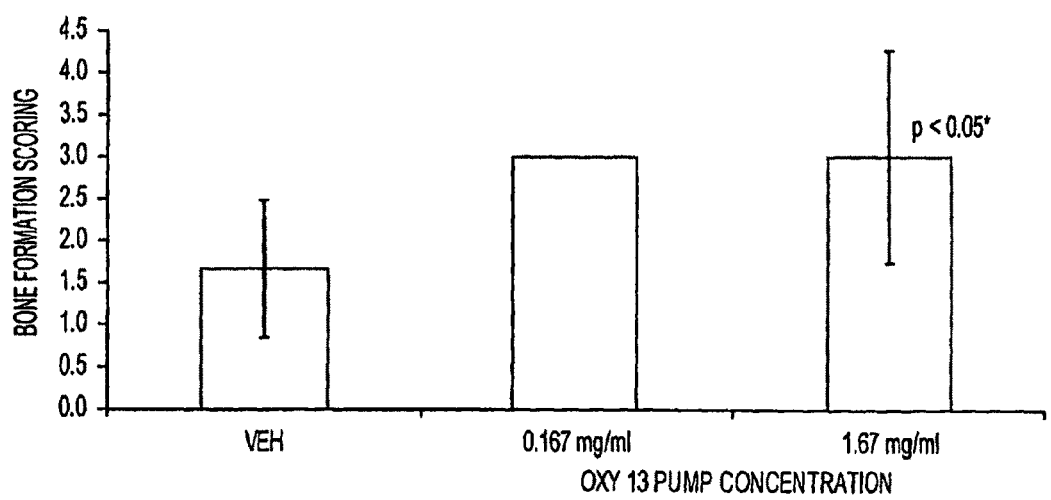

FIG. 7 shows graphically the bone formation scoring for rats treated with Oxy13 for two weeks (pump administration) in a rat periosteal femur model.

Figure 8:
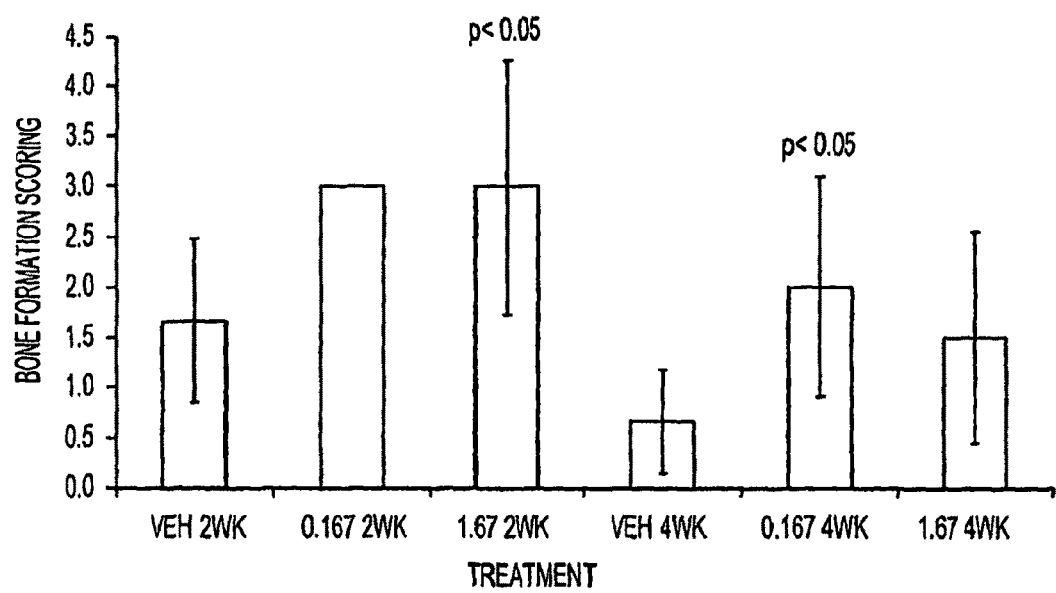

FIG. 8 shows graphically the bone formation scoring for rats treated with Oxy13 for four weeks (pump administration) in a rat periosteal femur model.

Figure 9A:
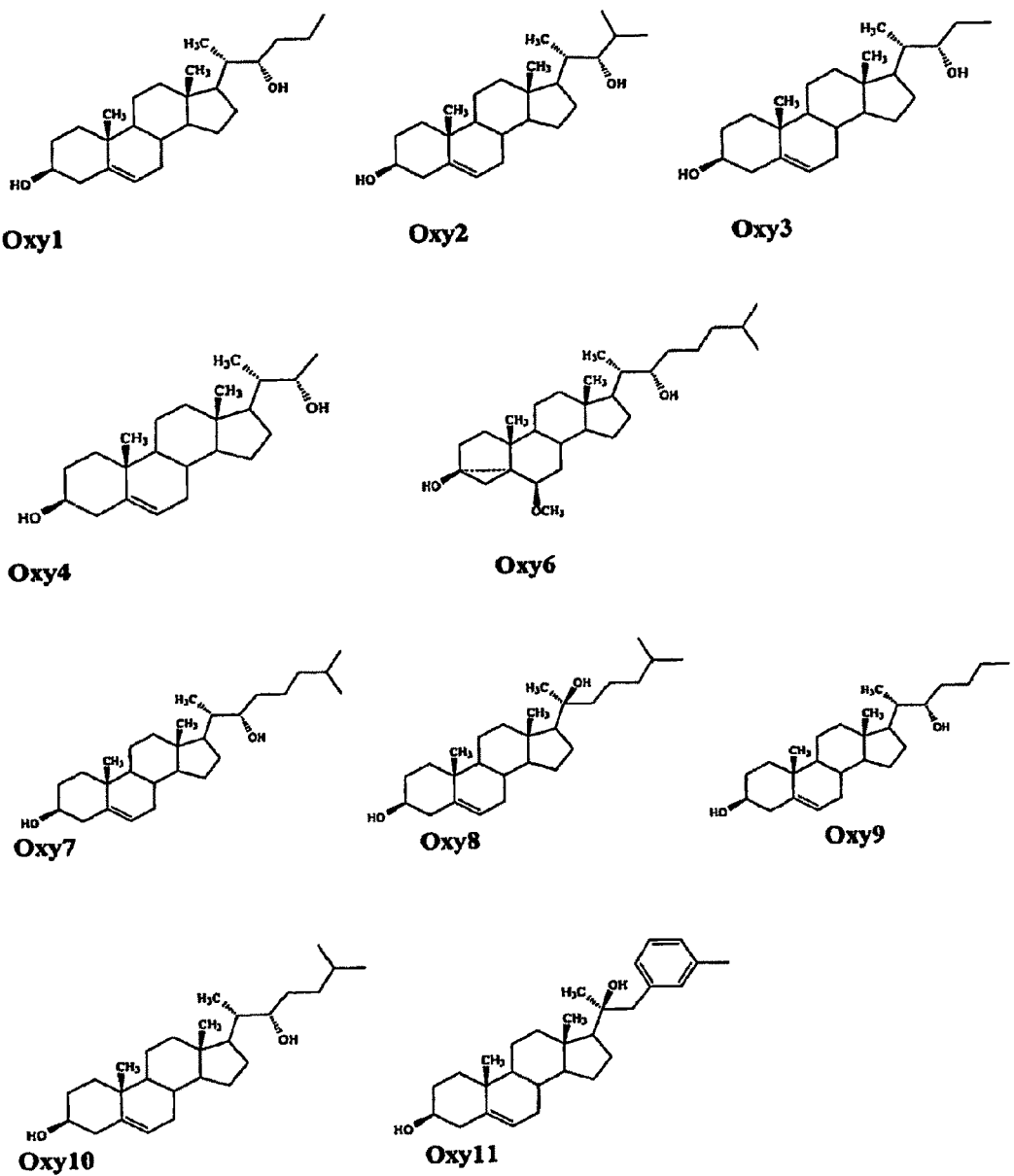
Figure 9B:
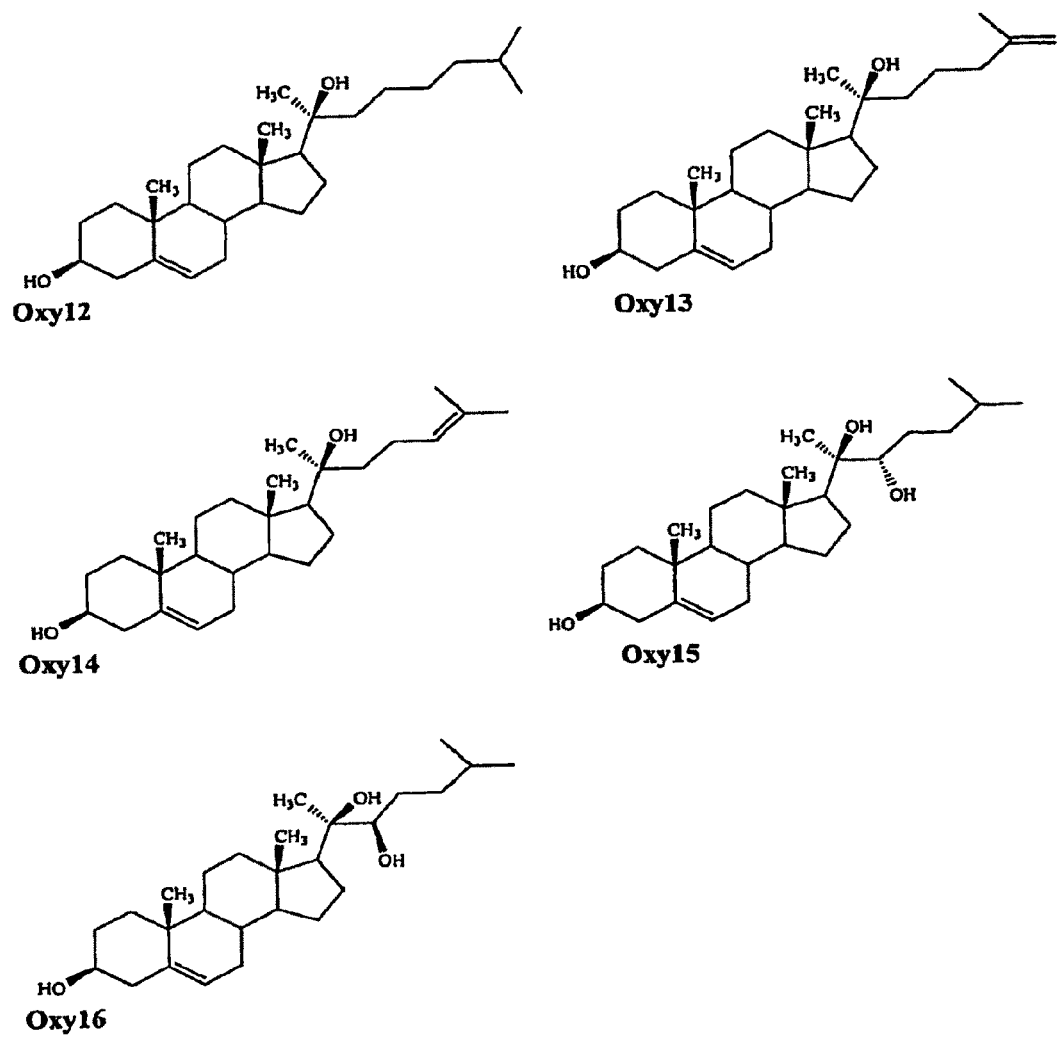

FIG. 9 presents structures of several oxysterols according to the invention.

Figure 10A:
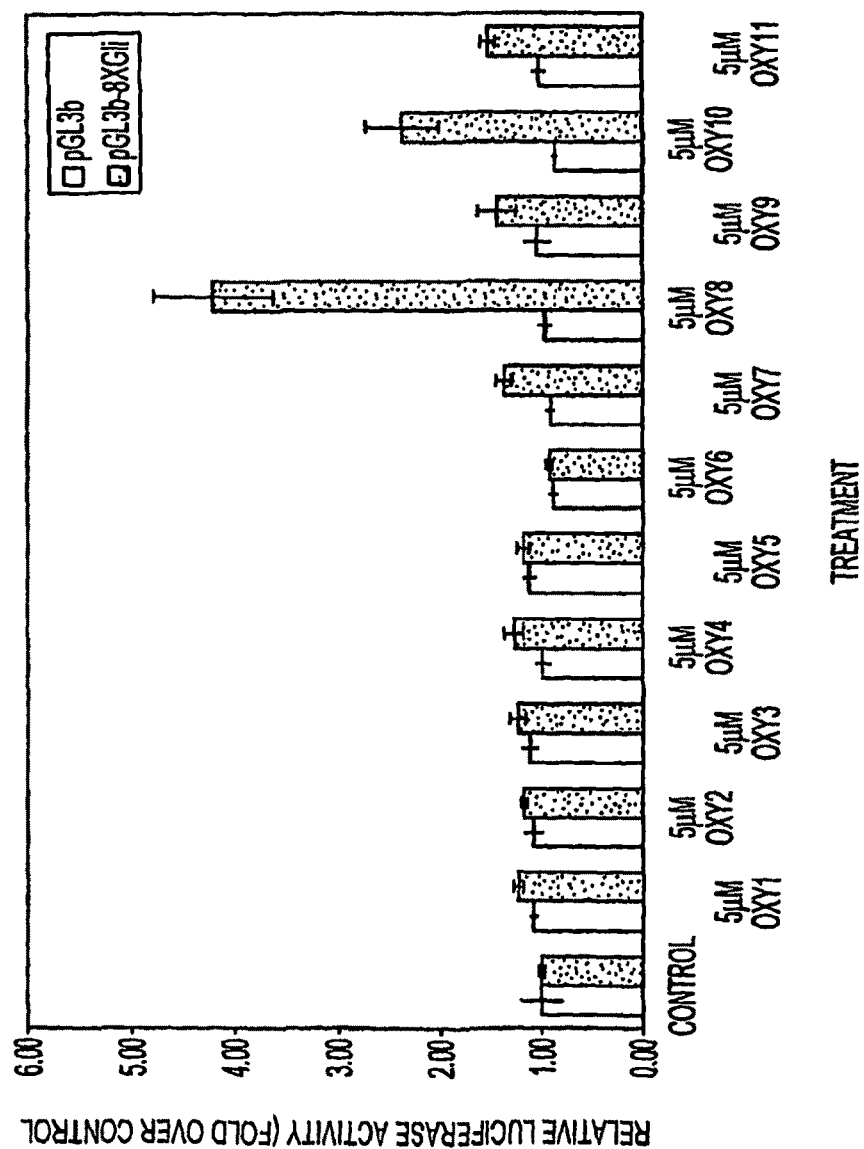
Figure 10B:
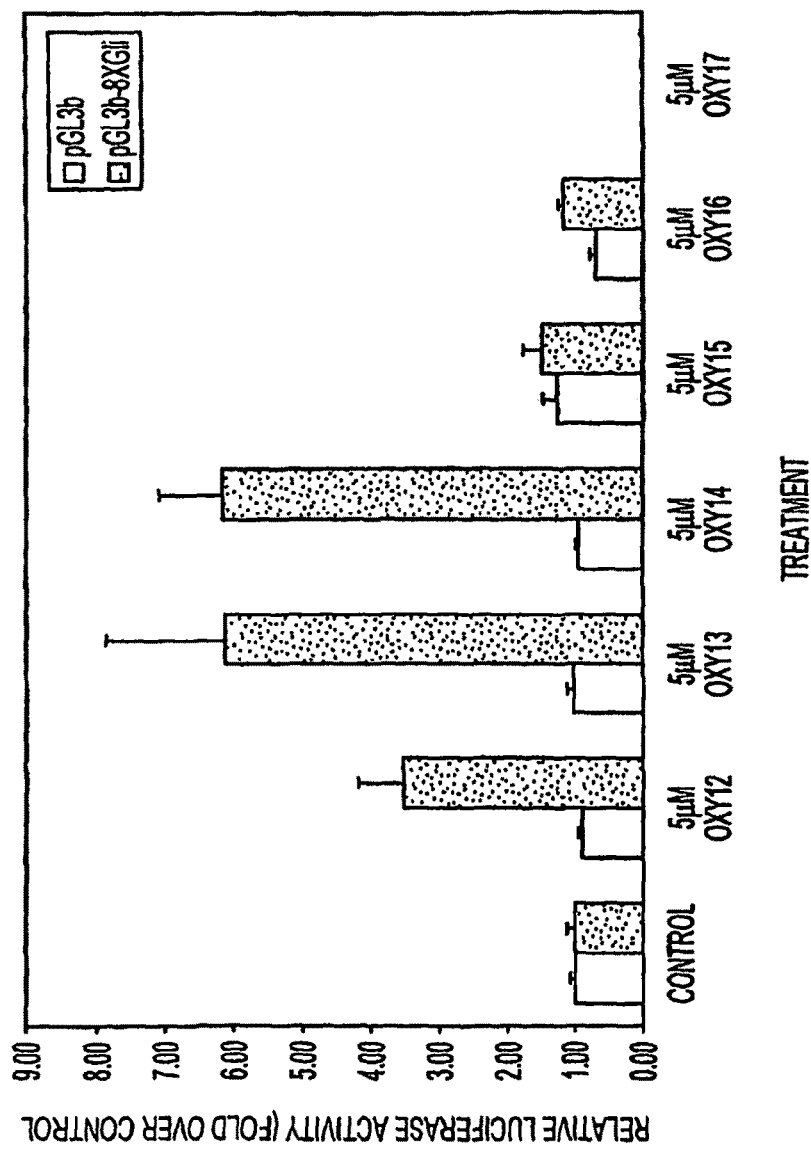

FIG. 10 shows the effect of OXY 1-OXY 11 on Gli reporter activity in M2-10B4 (M2) Marrow Stromal Cells.

DESCRIPTION OF THE INVENTION

The present invention relates, e.g., to novel synthetic oxysterols. The oxysterols can exhibit any of a variety of activities, including the stimulation of osteomorphogenesis or osteoproliferation, and/or the inhibition of adipocyte morphogenesis or adipocyte proliferation, and thus can be used to treat conditions mediated by, or exhibiting aberrant expression of, those physiological phenomena. The inventors report herein that certain oxysterols act by stimulating the hedgehog (Hh) signaling pathway. Thus oxysterols; including naturally occurring molecules as well as synthetic ones, can enhance this pathway, either in vitro or in vivo (in a subject) and can be used to treat conditions mediated by elements of the Hh pathway.

Advantages of oxysterols of the invention and methods for using them, e.g. for the treatment of suitable subjects, include that the compounds are inexpensive to manufacture, can be easily administered (e.g. locally or systemically), and exhibit great efficacy and potency. Bone morphogenic proteins (BMPs) can be used to enhance bone healing, but very large amounts of those proteins are required. Because oxysterols of the invention act synergistically with certain BMPs, lower doses of the proteins are required when they are co-administered with an oxysterol of the invention. This is another advantage of oxysterols of the invention. In some embodiments, administration of the compounds of the invention allows one to circumvent surgery, which can lead to scarring, e.g. in cosmetically sensitive areas.

One aspect of the invention is an oxysterol (e.g., an isolated oxysterol) represented by Formula 1.

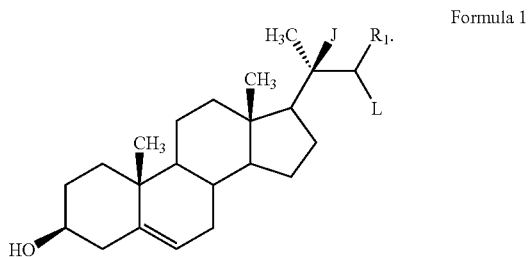

Formula 1

In Formula 1, J can be hydrogen (H) or hydroxyl (OH), L can be hydrogen (H) or hydroxyl (OH), and $R_1$ can be a linear or branched alkane of from 1 to 6 carbons, a linear or branched alkene of from 2 to 6 carbons, or phenyl optionally substituted with methyl. For example, at least one of J and L can be hydroxyl (OH) and/or at least one of J and L can be hydrogen (H). For example, $R_1$ can be other than 3-methylbutyl. For example, when J is OH, $R_1$ can be other than 3-methyl-2-butenyl, and when L is OH, $R_1$ can be other than n-propyl.

In one embodiment of the invention, J is hydroxyl (OH) and L is hydrogen (H). $R_1$ can be an alkane of from 5 to 6 carbons, for example, an alkane of from 5 to 6 carbons other than 3-methylbutyl. For example, $R_1$ can be 4-methylpentyl (Oxy 12). $R_1$ can be an alkene of from 5 to 6 carbons, for example, an alkene of from 5 to 6 carbons other than 3-methyl-2-butenyl. For example $R_1$ can be 3-methyl-3-butenyl (Oxy 13). $R_1$ can be phenyl optionally substituted with methyl. For example, $R_1$ can be 3-methylphenyl (Oxy 11).

In another embodiment, J is hydrogen (H) and L is hydroxyl (OH). $R_1$ can be an alkane of from 1 to 6 carbons. For example, $R_1$ can be methyl (Oxy 4), ethyl (Oxy 3), n-butyl (Oxy 9), or 4-methylpentyl (Oxy 7).

In another embodiment, J is hydroxyl (OH) and K is hydroxyl (OH). $R_1$ can be an alkane of from 1 to 6 carbons. For example, $R_1$ can be 3-methylbutyl (Oxy 15 and Oxy 16).

In another embodiment, a compound has Formula I and J is H or OH and L is H or OH. At least one of J and L is H and at least one of J and L is OH. R1 is selected from the group consisting of alkane of from 1 to 6 carbons, alkene of from 2 to 6 carbons, and phenyl optionally substituted with methyl. R1 is not 3-methylbutyl. When J is OH, R1 is not 3-methyl-2-butenyl. When L is OH, R1 is not n-propyl.

One embodiment is a pharmaceutical composition that comprises a compound having Formula I and a pharmaceutically acceptable carrier. J is H or OH, and L is H or OH. At least one of J and L is OH. R1 is selected from the group consisting of alkane of from 1 to 6 carbons, alkene of from 2 to 6 carbons, and phenyl optionally substituted with methyl. When one of J and L is H, R1 is not 3-methylbutyl. In another embodiment, the pharmaceutical composition further includes at least one additional oxysterol.

In one embodiment, the pharmaceutical composition includes at least two of Oxy 3, Oxy 4, Oxy 7, Oxy 9, Oxy 11, Oxy 12, Oxy 13, Oxy 14, and Oxy 15. The pharmaceutical composition may further comprise at least one of 20(S)-hydroxycholesterol, 22(S)-hydroxycholesterol, or 22(R)-hydroxycholesterol, or any other oxysterol. In one embodiment, the pharmaceutical composition includes Oxy 16.

Another aspect of the invention is a complex (in vitro or in vivo) comprising an oxysterol of the invention and any of variety of intracellular oxysterol binding molecules (e.g., proteins, receptors, etc.), examples of which will be evident to the skilled worker.

As used herein, the singular forms "a" "an" and "the" include plural referents unless the context clearly dictates otherwise. For example, "an" oxysterol" includes multiple oxysterols, e.g. 2, 3, 4, 5 or more oxysterols, which can be the same or different.

Another aspect of the invention is a combination or pharmaceutical composition comprising an oxysterol of the invention (optionally in combination of other agents as discussed above) and at least one additional agent, selected, e.g., from the group consisting of parathyroid hormone, sodium fluoride, insulin-like growth factor I (ILGF-I), insulin-like growth factor II (ILGF-II), transforming growth factor beta (TGF-β), a cytochrome P450 inhibitor, a phospholipase activator, arachadonic acid, a COX enzyme activator, an osteogenic prostanoid, an ERK activator, BMP 2, 4, 7 and 14.

Another aspect of the invention is a kit for performing any of the methods discussed herein, comprising one or more oxysterols of the invention, individually or in combination with one another, or in combination with naturally occurring oxysterols and/or with BMPs or other agents noted herein, optionally packaged in one or more containers. When the kit is for treating a subject, the oxysterol(s) may be in the form of a pharmaceutically acceptable composition.

Another aspect of the invention is a method for modulating a hedgehog (Hh) pathway mediated response in a cell or tissue, comprising contacting the cell or tissue with an effective amount of an oxysterol or a pharmaceutical composition of the invention. The cell or tissue may be in vitro or in a subject (in vivo). In the latter case, the subject can be one who would benefit, e.g., from the stimulation of osteomorphogenesis, osteoproliferation or hair growth; or the inhibition of adipocyte morphogenesis or adipocyte proliferation.

A "subject," as used herein, includes any animal that exhibits a symptom of a condition that can be treated with an oxysterol of the invention. Suitable subjects (patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by an oxysterol of the invention (e.g. stimulation of osteomorphogenesis or osteoproliferation, and/or the inhibition of adipocyte morphogenesis or adipocyte proliferation). Subjects exhibiting non-pathogenic conditions, such as alopecia, are also included. The ability of an oxysterol to "modulate" a response, as used herein, includes the ability to increase or to decrease the level of the response compared to the response elicited in the absence of the oxysterol. The aberrant activities may be regulated by any of a variety of mechanisms, including activation of a hedgehog activity, etc. The aberrant activities can result in a pathological condition.

An "effective amount," as used herein, includes an amount that can bring about a detectable effect. A "therapeutically effective amount," as used herein, includes an amount that can bring about a detectable therapeutic effect (e.g. the amelioration of a symptom).

Another aspect of the invention is a method for treating a subject suffering from a condition known to be mediated by oxysterols or by the hedgehog pathway, comprising administering to the subject an effective amount of an oxysterol or a pharmaceutical composition of the invention. Some such conditions are discussed elsewhere herein.

Another aspect of the invention is a method for inducing osteoblastic differentiation of a mammalian mesenchymal stem cell, comprising contacting the cell with an effective amount of an oxysterol or a pharmaceutical composition of the invention. This method can further comprise treating the mammalian mesenchymal cell with at least one secondary agent, selected from the group consisting of parathyroid hormone, sodium fluoride, insulin-like growth factor I (ILGF-I), insulin-like growth factor U (ILGF-II), transforming growth factor beta (TGF-β), a cytochrome P450 inhibitor, a phospholipase activator, arachadonic acid, a COX enzyme activator, an osteogenic prostanoid and an ERK activator.

Other aspects of the invention using an oxysterol or a pharmaceutical composition of the invention include methods for (1) stimulating a mammalian cell (e.g. a mesenchymal stem cell, an osteoprogenitor cell or a cell in a calvarial organ culture) to express a level of a biological marker of osteoblastic differentiation (e.g. an increase in at least one of alkaline phosphatase activity, calcium incorporation, mineralization or expression of osteocalcin mRNA) which is greater than the level of the biological marker in an untreated cell; (2) treating a subject (patient) to increase the differentiation of marrow stromal cells into osteoblasts; (3) treating a subject to induce bone formation (to increase bone mass); or (4) treating a patient exhibiting clinical symptoms of osteoporosis. Methods for treating a subject may comprise administering an oxysterol or a pharmaceutical composition of the invention at a therapeutically effective dose, in an effective dosage form, and at a selected interval to effectively carry out the elicit the desired response (e.g. to increase bone mass, to increase the number of osteoblasts present in bone tissue, to ameliorate the symptoms of the osteoporosis, respectively).

Another aspect of the invention is a method for treating a subject to induce bone formation comprising: harvesting mammalian mesenchymal stem cells; treating the mammalian mesenchymal cells with an oxysterol or a pharmaceutical composition of the invention, wherein the oxysterol induces the mesenchymal stem cells to express at least one cellular marker of osteoblastic differentiation; and administering the differentiated cells to the subject.

Another aspect of the invention is an implant for use in an animal (e.g. human) body, comprising a substrate having a surface, wherein at least the surface of the implant includes an oxysterol or a pharmaceutical composition of the invention, in an amount sufficient to induce bone formation in the surrounding bone tissue. The substrate may be formed into the shape of, e.g., a pin, screw, plate, or prosthetic joint.

Another aspect of the invention is a method for inhibiting adipocyte differentiation of a mammalian mesenchymal stem cell, comprising contacting the mesenchymal stem cell with an effective amount of an oxysterol or a pharmaceutical composition of the invention. The cell may be in vitro or in a subject (in vivo).

Another aspect of the invention is a method for treating a subject in need of wound healing, angiogenesis, an increase in osteomorphogenesis or osteoproliferation (e.g., a subject in need of bone healing or suffering from osteoporosis), weight reduction, hair growth, the enhancement of cartilage production, or suffering from a neurological disorder.

Another aspect of the invention is a method for identifying a modulator of a hedgehog pathway-mediated activity, comprising screening candidate oxysterols for the ability to modulate an activity in one of the hedgehog-related in vitro assays discussed herein (e.g., induction of expression of the Gli1 gene, for example by stimulation of a Gli1 promoter; activation of a reporter construct driven by a multimerized Gli-1 responsive element; induction of expression of Patched; inhibition of a putative oxysterol-induced effect by cyclopamine; etc.

Another aspect of the invention is in a method for modulating a hedgehog (Hh) pathway mediated response in a cell or tissue (in vitro or in a subject), the improvement comprising contacting the cell or tissue with an oxysterol of the invention. Another aspect of the invention is in a method for treating a subject for one of the indications as described herein (e.g., to increase the differentiation of marrow stromal cells into osteoblasts, or to induce bone formation, the improvement comprising contacting the cell or tissue with an oxysterol of the invention).

One aspect of the invention is an oxysterol (e.g. an isolated oxysterol) of the invention as represented by Formula I, above. Examples of oxysterols, designated as Oxy 1 through Oxy 4 and Oxy 6 through Oxy 16 are presented in FIG. 9. For example, the compounds designated as Oxy 7, Oxy 9, Oxy11, Oxy12, Oxy13, Oxy 14, and Oxy 15 can stimulate at least a measurable amount of a hedgehog-mediated pathway and/or osteomorphogenesis or osteoproliferation (or a marker thereof), and/or can inhibit at least a measurable amount of adipocyte morphogenesis or adipocyte proliferation (or a marker thereof). Oxy 3 and Oxy 4 can act as enhancers of activity in combination with other oxysterols. For example, the combination of Oxy 3 and 20(S)-hydroxycholesterol, as well as the combination of Oxy4 and 20(S)-hydroxycholestol were found to enhance the incorporation of $^{45}$Ca in an assay used to measure mineralization in M2 cells over the incorporation when only 20(S)-hydroxycholestol was applied. Oxy 7 was found to be minimally enhancing of activity.

Other oxysterols (e.g. Oxy 1, Oxy 2 and Oxy 16) have not been demonstrated to modulate one of the activities mentioned above. However, these molecules, which share structural features with the oxysterols discussed above, would be expected to act as competitive inhibitors of those compounds and, in some cases, to act as antagonists of one of the mentioned activities (e.g., of osteomorphogenesis or osteoproliferation, etc.).

In some aspects of the invention (e.g., methods in which oxysterols are used to stimulate members of the Hh pathway, naturally occurring oxysterols (e.g., 22(S)-hydroxycholesterol (sometimes referred to herein as "22S"); 22(R)-hydroxycholesterol (sometimes referred to herein as "22R"); 20(S)-hydroxycholesterol (also known as 20-alpha hydroxycholesterol, and sometimes referred to herein as "20S"); 5-cholesten-3beta, 20alpha-diol 3-acetate; 24-hydroxycholesterol; 24(S), 25-epoxycholesterol; pregnanolone, 26-hydroxycholesterol; 4beta-hydroxycholesterol; can also be used.

By "isolated" is meant removed from its original environment (e.g., the natural environment if it is naturally occurring), and/or separated from at least one other component with which it is naturally associated. For example, a naturally-occurring oxysterol present in its natural living host is not isolated, but the same oxysterol, separated from some or all of the coexisting materials in the natural system, is isolated. Such an oxysterol can be part of a composition (e.g. a pharmaceutical composition), and still be isolated in that such composition is not part of its natural environment. Also, an intermediate product in the synthesis of another oxysterol, wherein the intermediate product is not purified or separated from other components in the reaction pathway, is not isolated.

It was observed that the hydroxyl groups in 20(S)-hydroxylcholesterol and 22(S)-hydroxycholesterol are about 12-14 Å apart. Therefore, the putative receptor that mediates the effects of osteoinductive oxysterols may have a requirement for a diol in which the two hydroxyl groups are approximately 12-14 Å apart. In this light, we have synthesized and envision reaction schemes for the synthesis of synthetic oxysterols and derivatives thereof in which the functional group at the steroid 17 position is modified. With respect to modification of the functional group at the steroid 17 position, variants include, for example, the following: placement of a hydroxyl group at the steroid 20 position, the steroid 22 position, or both; inclusion of only single carbon-carbon bonds (alkane), double bonds (alkene), triple bonds (alkyne), or aromatic groups (e.g., phenyl, methylphenyl) in the functional group; and variation of stereochemistry. It is desirable to produce synthetic oxysterols that are derivatives of 20S-hydroxycholesterol and that are active even in the absence of 22S-hydroxycholesterol or 22R-hydroxycholesterol. For example, such synthetic oxysterols can be active in that they induce a measurable amount of a hedgehog-mediated pathway and/or osteomorphogenesis or osteoproliferation (or a marker thereof), and/or inhibit at least a measurable amount of adipocyte morphogenesis or adipocyte proliferation (or a marker thereof).

Combinations of oxysterols of the invention, with one another and/or with other oxysterols, including naturally occurring oxysterols; can also be used in methods of the invention. Among the naturally occurring oxysterols that can be used are: 22(S)-hydroxycholesterol; 22(R)-hydroxycholesterol; 20(S)-hydroxycholesterol (also known as 20-alpha hydroxycholesterol); 5-cholesten-3beta, 20alpha-diol 3-acetate; 24-hydroxycholesterol; 24(S), 25-epoxycholesterol; 26-hydroxycholesterol; and/or 4beta-hydroxycholesterol.

Methods for making the oxysterols of the invention are conventional. Example VIII, below, provides illustrative synthetic procedures, as well as bibliographic citations.

The oxysterols discussed herein can be used to modulate a variety of responses or activities in a cell or tissue, in vitro or in vivo (in a subject). By "modulate" is meant is to increase or decrease the degree of the response.

The Examples herein illustrate some of the many activities that are exhibited by oxysterols of the invention. The present inventors and colleagues previously demonstrated that naturally occurring oxysterols (e.g. 22(S)-hydroxycholesterol (sometimes referred to herein as "22S"); 22(R)-hydroxycholesterol (sometimes referred to herein as "22R"); 20(S)-hydroxycholesterol (also known as 20-alpha hydroxycholesterol, and sometimes referred to herein as "20S"); 5-cholesten-3beta, 20alpha-diol 3-acetate; 24-hydroxycholesterol; 24(S), 25-epoxycholesterol; pregnanolone, 26-hydroxycholesterol; and 4beta-hydroxycholesterol; individually or in combination, exhibit osteogenic and anti-adipogenic properties. See, e.g., the commonly owned and published PCT international applications WO2004/019884, WO2005/020928, WO2005/020928; and WO2006/12902, all of which are incorporated herein by reference in their entirety. See also Dwyer et at. (Jan. 2, 2007), J. Biol. Chem, Epub ahead of print; Parhami et al. (2002) J. Bone Miner. Res. 17, 1997-2003; Kha et al. (2004) J Bone Miner Res. 19, 830-840; Shouhed et al. (2005) J Cell Biochem. 95, 1276-1283; Richardson et al. (2006) (J Cell Biochem, in press); and Aghaloo et al. (2006) J Orthop Res, in press). In the present application, the inventors report that the novel oxysterols of the invention exhibit similar activities, as well as further activities. Such activities were demonstrated by a variety of markers of such activities.

Example II shows the ability of certain oxysterols to induce the formation of osteoblastic cells in cultures of marrow stromal cells, which are progenitors of osteoblastic cells that make bone. In order to assess osteogenic differentiation of cells, one or more markers of osteogenic differentiation were measured in untreated cells and cells treated with the test oxysterols. These markers include alkaline phosphatase (ALP) activity, osteocalcin mRNA expression and mineral formation in cultures of marrow stromal cells. Activation of one or more markers by a single or combination of oxysterols is indicative of their osteogenic property. Furthermore, the ability of these molecules to inhibit adipocyte formation was demonstrated in a conventional in vitro adipocyte differentiation assay using pluripotent bone marrow stromal cells.

Examples III-VI show other properties of oxysterols. Example VI shows that naturally occurring oxysterols can enhance hair growth in mice.

Example VII investigates a molecular mechanism by which oxysterols induce the osteogenic and inhibit the adipogenic differentiation of progenitor cells, and shows that oxysterols activate the Gli transcription factor that mediates signaling in response to hedgehog molecules. In addition to naturally occurring oxysterols, at least the following synthetic oxysterols of the invention were shown to affect the hedgehog pathway (as indicated by the stimulation of Gli reporter activity in M2-10B4 Marrow Stromal Cells): Oxy 9, 11, 12, 13, and 14. See FIG. 10.

Oxysterols can be used to treat a number of indications in subjects. For example, the hedgehog signaling pathway (sometimes referred to herein as "hedgehog" or "hedgehog pathway") has been reported to be implicated in a number of pathological conditions, and agonists or antagonists of components of the hedgehog signaling pathway have been suggested to serve as potential treatments for such conditions. Particular oxysterols of the invention can be used to treat such hedgehog-mediated conditions. Furthermore, certain oxysterols have been reported to elicit a variety of effects, including potent effects on cholesterol metabolism, to be present in atherosclerotic lesions, and to play a role in various physiologic processes, including, e.g., cellular differentiation, inflammation, apoptosis, adipogenesis and adipocyte differentiation, bone morphogenesis and differentiation (osteogenesis or osteogenic differentiation), neuroprotection, chondrocyte proliferation and differentiation, and steroid production. Particular oxysterols of the present invention can be used to modulate such activities, and to treat conditions in which such activities play a pathological role.

A variety of conditions can be treated by compounds of the invention. Some of these conditions have been reported to be mediated by aberrant expression of a hedgehog signaling pathway; others have been reported to be mediated by other mechanisms discussed elsewhere herein. In some conditions, these mechanisms overlap. Without being bound by any particular mechanism, it is suggested that among the conditions that can be treated by oxysterols of the invention are, e.g.: (1) conditions that benefit from an enhancement of bone morphogenesis and/or proliferation. These conditions include, e.g., bone healing (e.g., of bone fractures), osteoporosis, metabolic bone disease, or chronic kidney disease and related disorders associated with end stage renal disease. As noted elsewhere herein, compounds of the invention exhibit a synergistic effect with certain bone morphogenic proteins (BMPs, e.g. BMP 2, 4, 7 or 14). The administration of a compound of the invention, alone or in combination with an added BMP, can be used when it is desirable, e.g., to enhance an activity of a BMP, such as to promote bone growth, maintain kidney structure and function, promote skeletal mineralization, prevent vascular calcification, etc; (2) conditions that benefit from the inhibition of adipogenesis or adipogenic differentiation of cells, including, e.g., obesity; (3) cancers whose growth and/or metastasis can be inhibited, including, e.g., basal cell carcinoma (e.g., using a topical formulation) or other solid tumors, including medulloblastoma, small cell lung cancer, pancreatic cancer, stomach cancer, esophageal cancer, colorectal cancer, prostate cancer and breast cancer (e.g., using a systemic formulation); (4) neurological disorders, including, e.g., stroke, and conditions requiring neuroprotection or the need for repair of damaged nerves, including reduction of infarct size; (5) alopecia (loss of hair growth, such as in male pattern baldness), wherein it is desirable to initiate and/or maintain hair growth, e.g., by stimulating follicle growth, thickness, quality or quantity of hair; (6) cardiovascular disorders (e.g., using local delivery); and (7) disorders that would benefit from enhanced chondrocyte proliferation and/or differentiation (e.g. the enhancement of cartilage production), such as osteoarthritis, loss of cartilage associated with aging, etc.

Treatment with a compound of the invention can be used to enhance survival of neurons and other neuronal cells in both the central nervous system and the peripheral nervous system. The terms "a compound of the invention" or a "hedgehog agonist" are sometimes used herein to refer to a synthetic oxysterol of the invention. Without wishing to be bound by any particular mechanism, it is suggested that the ability of hedgehog protein to regulate neuronal differentiation during development of the nervous system and also presumably in the adult state indicates that certain of the hedgehog proteins can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis. Many neurological disorders are associated with degeneration of discrete populations of neuronal elements and may be treatable with a therapeutic regimen which includes an oxysterol molecule as a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of hedgehog stimulators (such as particular oxysterols of the invention) effects, in order to control, for example, differentiation and apoptotic events which give rise to loss of neurons (e.g. to enhance survival of existing neurons) as well as promote differentiation and repopulation by progenitor cells in the area affected. In some embodiments, the compound is stereotactically provided within or proximate the area of degeneration. In addition to degenerative-induced dementias, a pharmaceutical preparation of the invention can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus ceruleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barré syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of a hedgehog stimulator (e.g. comprising an oxysterol of the invention) can used to treat a restricted form of cerebellar cortical degeneration involving the anterior lobes (vermis and leg areas) such as is common in alcoholic patients.

In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a hedgehog agonist (such as an oxysterol of the invention) can be used alone, or in conjunction with other neurotrophic factors such as CNTF, BDNF or NGF to prevent and/or reverse motor neuron degeneration in ALS patients.

Compounds of the present invention can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrythmias which may arise from a degenerative condition of the nerves innervating the striated muscle of the heart.

Furthermore, the expression of hedgehog proteins in sensory and motor neurons of the head and trunk (including limb buds) suggests a role for hedgehog proteins in the development and maintenance of dendritic processes of axonal neurons. Potential roles for hedgehog proteins consequently include guidance for axonal projections and the ability to promote differentiation and/or maintenance of the innervating cells to their axonal processes. Accordingly, without wishing to be bound by any particular mechanism, it is suggested that compositions comprising agents of the invention may be employed to support, or alternatively antagonize the survival and reprojection of several types of ganglionic neurons sympathetic and sensory neurons as well as motor neurons. In particular, such therapeutic compositions may be useful in treatments designed to rescue, for example, various neurons from lesion-induced death as well as guiding reprojection of these neurons after such damage. Such diseases include, but are not limited to, CNS trauma, infarction, infection (such as viral infection with varicella-zoster), metabolic disease, nutritional deficiency, toxic agents (such as cisplatin treatment). Moreover, agents that antagonize hedgehog agents may be useful in the selective ablation of sensory neurons, for example, in the treatment of chronic pain syndromes.

As appropriate, agents of the invention can be used, alone or in the presence of a hedgehog polypeptide, in nerve prostheses for the repair of central and peripheral nerve damage. In particular, where a crushed or severed axon is intubulated by use of a prosthetic device, agents of the invention can be added to the prosthetic device to increase, in the presence of a hedgehog polypeptide, the rate of growth and regeneration of the dendritic processes. Accordingly, a severed axonal process can be directed toward the nerve ending from which it was severed by a prosthesis nerve guide which contains, e.g., a semi-solid formulation containing a hedgehog polypeptide and/or a compound of the invention, or which is derivatized along the inner walls with a hedgehog polypeptide and/or a compound of the invention.

In another embodiment, the subject method can be used in the treatment of neoplastic or hyperplastic transformations such as may occur in the central nervous system. For instance, certain oxysterols which induce differentiation of neuronal cells can be utilized to cause such transformed cells to become either post-mitotic or apoptotic. Treatment with an agent of the invention may facilitate disruption of autocrine loops, such as TGF-β or PDGF autostimulatory loops, which are believed to be involved in the neoplastic transformation of several neuronal tumors. Hedgehog agonists of the invention may, therefore, thus be of use in the treatment of, for example, malignant gliomas, medulloblastomas, neuroectodermal tumors, and ependymonas.

Yet another aspect of the present invention concerns the application of the observation that hedgehog proteins are morphogenic signals involved in other vertebrate organogenic pathways in addition to neuronal differentiation as described above, having apparent roles in other endodermal patterning, as well as both mesodermal and endodermal differentiation processes. Hedgehog proteins have been reported to play a role in proper limb growth and patterning by initiating expression of signaling molecules, including BMP-2 in the mesoderm and FGF-4 in the ectoderm. Thus, without wishing to be bound by any particular mechanism, it is contemplated that compositions comprising hedgehog-stimulatory molecules of the invention can also be utilized for both cell culture and therapeutic methods involving generation and maintenance of non-neuronal tissue.

In one embodiment, the present invention makes use of the observation that hedgehog proteins are apparently involved in controlling the development of stem cells responsible for formation of the digestive tract, liver, lungs, and other organs which derive from the primitive gut. Hedgehog proteins have been reported to serve as an inductive signal from the endoderm to the mesoderm, which is critical to gut morphogenesis. Therefore, for example, hedgehog agonists (such as the compounds or compositions of the invention) can be employed in the development and maintenance of an artificial liver which can have multiple metabolic functions of a normal liver. In an illustrative embodiment, the compounds can be used to induce differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog agonists of the invention can be utilized in conjunction with transplantation of such artificial livers, as well as embryonic liver structures, to promote intraperitoneal implantation, vascularization, and in vivo differentiation and maintenance of the engrafted liver tissue.

In yet another embodiment, agents of the invention can be employed therapeutically to regulate such organs after physical, chemical or pathological insult. For instance, therapeutic compositions comprising hedgehog agonists can be utilized in liver repair subsequent to a partial hepatectomy. Similarly, therapeutic compositions containing hedgehog agonists can be used to promote regeneration of lung tissue in the treatment of emphysema.

In still another embodiment of the invention, compositions comprising hedgehog agonists can be used in the in vitro generation of skeletal tissue, such as from skeletogenic stem cells, as well as the in vivo treatment of skeletal tissue deficiencies. The present invention particularly contemplates the use of hedgehog agonists which maintain a skeletogenic activity, such as an ability to induce chondrogenesis and/or osteogenesis. By "skeletal tissue deficiency" is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the invention, the subject method comprises treating the afflicted connective tissue with a therapeutically sufficient amount of a hedgehog agonist to generate a cartilage repair response in the connective tissue by stimulating the differentiation and/or proliferation of chondrocytes embedded in the tissue. Induction of chondrocytes by treatment with a hedgehog agonist can subsequently result in the synthesis of new cartilage matrix by the treated cells. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralisation into fibrotic tissue by maintaining a constant production of new cartilage.

In an illustrative embodiment, the subject method can be used to treat cartilage of a diarthroidal joint, such as a knee, an ankle, an elbow, a hip, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a hedgehog agonist into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates, isolated chondrocytes, and chondrocytes attached to natural or synthetic polymers. For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog agonist during the culturing process, in order to induce and/or maintain differentiated chondrocytes in the culture in order as to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a hedgehog agonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog agent of the present invention can be employed as part of a method for treating bone loss in a subject, e.g. to prevent and/or reverse osteoporosis and other osteopenic disorders, as well as to regulate bone growth and maturation. Periodontal implants are also contemplated. For example, preparations comprising hedgehog agonists can be employed, for example, to induce endochondral ossification, at least so far as to facilitate the formation of cartilaginous tissue precursors to form the "model" for ossification. Therapeutic compositions of hedgehog agonists can be supplemented, if required, with other osteoinductive factors, such as bone growth factors (e.g. TGF-β factors, such as the bone morphogenetic factors BMP-2, BMP4, BMP-7 or BMP 14 as well as activin), and may also include, or be administered in combination with, an inhibitor of bone resorption such as estrogen, bisphosphonate, sodium fluoride, calcitonin, or tamoxifen, or related compounds. However, it will be appreciated that hedgehog proteins are likely to be upstream of BMPs, so that treatment with a hedgehog polypeptide and/or a hedgehog agonist will have the advantage of initiating endogenous expression of BMPs along with other factors.

In yet another embodiment of the present invention, molecules of the invention that act as hedgehog antagonists can be used to inhibit spermatogenesis. Thus, in light of the observation that hedgehog proteins are involved in the differentiation and/or proliferation and maintenance of testicular germ cells, hedgehog antagonist can be utilized to block the action of a naturally-occurring hedgehog protein. In a preferred embodiment, the hedgehog antagonist inhibits the biological activity of a hedgehog protein with respect to spermatogenesis, by competitively binding hedgehog receptors in the testis. In similar fashion, hedgehog agonists and antagonists are potentially useful for modulating normal ovarian function.

The oxysterols discussed herein can be formulated into various compositions, e.g., pharmaceutical compositions, for use in therapeutic treatment methods. The pharmaceutical compositions can be assembled as a kit. Generally, a pharmaceutical composition of the invention comprises an effective amount of an oxysterol or combination of the invention. An "effective amount," as used herein, is an amount that is sufficient to effect at least a detectable therapeutic response in the individual over a reasonable time frame. For example, it can ameliorate, at least to a detectable degree, the symptoms of a hedgehog-mediated condition, etc.

The composition can comprise a carrier, such as a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition or kit of the invention can contain other pharmaceuticals, as noted elsewhere herein, in addition to the oxysterols of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

Formulations suitable for oral administration can consist of liquid solutions, such as an effective amount of the agent dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g. intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The oxysterols of the invention, alone or in combination with other therapeutic agents, can be made into aerosol formulations to be administered via inhalation. These aerosol formulations can be placed into pressurized acceptable propellants, such as dichlorodifluoromethane, propane, nitrogen and the like.

The oxysterols of the invention, alone or in combinations with other therapeutic agents, can be made into suitable formulations for transdermal application and absorption (Wallace et al., 1993, supra). Transdermal electroporation or iontophoresis also can be used to promote and/or control the systemic delivery of the agents and/or pharmaceutical compositions of the present invention through the skin (e.g., see Theiss et al. (1991), *Meth. Find. Exp. Clin. Pharmacol.* 13, 353-359).

Formulations which are suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

One skilled in the art will appreciate that a suitable or appropriate formulation can be selected, adapted or developed based upon the particular application at hand.

Dosages for an oxysterols of the invention can be in unit dosage form, such as a tablet or capsule. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds of the present invention by a direct or indirect analysis of appropriate patient samples (e.g., blood and/or tissues).

The dose of an oxysterol of the invention, or composition thereof, administered to an animal, particularly a human, in the context of the present invention should be sufficient to effect at least a therapeutic response in the individual over a reasonable time frame. The exact amount of the dose will vary from subject to subject, depending on the species, age, weight and general condition of the subject, the severity or mechanism of any disorder being treated, the particular agent or vehicle used, its mode of administration and the like. The dose used to achieve a desired concentration in vivo will be determined by the potency of the particular oxysterol employed, the pharmacodynamics associated with the agent in the host; the severity of the disease state of infected individuals, as well as, in the case of systemic administration, the body weight and age of the individual. The size of the dose also will be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about or from about 100 ng to about 600 mg, or from about 1 mg to about 500 mg, or from about 20 mg to about 400 mg, or from about 40 mg to about 200 mg of a compound of according to the present invention. A dose can be administered once per day, twice per day, four times per day, or more than four times per day as required to elicit a desired therapeutic effect. For example, a dose administration regimen can be selected to achieve a blood serum concentration of a compound of the present invention in the range of from about 0.01 to about 1000 nM, or from about 0.1 to about 750 nM, or from about 1 to about 500 nM, or from about 20 to about 500 nM, or from about 100 to about 500 nM, or from about 200 to about 400 nM. For example, a dose administration regime can be selected to achieve an average blood serum concentration with a half maximum dose of a compound of the present invention in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

A therapeutically effective dose of an oxysterol or other agent useful in this invention is one which has a positive clinical effect on a patient as measured by the ability of the agent to improve bone homeostasis, bone formation or bone repair, as described above, etc. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

By way of example, the invention may include elevating endogenous, circulating oxysterol levels over the patient's basal level. In a normal adult levels are about 10-400 ng/ml depending on age and type of oxysterol, as measured by mass spectrometry. Those skilled in the art of pharmacology would be able to select a dose and monitor the same to determine if an increase circulating levels over basal levels has occurred.

When given in combined therapy, the other agent can be given at the same time as the oxysterol, or the dosing can be staggered as desired. The two (or more) drugs also can be combined in a composition. Doses of each can be less when used in combination than when either is used alone.

The invention may include treatment with an additional agent which acts independently or synergistically with at least a first oxysterol to maintain bone homeostasis, enhance bone formation, enhance bone repair, etc. Additional agents may be agents which, e.g., stimulate the mechanistic pathway by which oxysterols enhance osteoblastic differentiation. Among such suitable agents are bone morphogenic proteins (e.g., BMP 2, 4, 7, and/or 14), which have been shown by the inventors to act synergistically with oxysterols.

Therefore, the invention may include the use of a combination of at least one oxysterol of the invention and at least one BMP to induce osteoblastic differentiation or bone formation. This combination of agents to maintain bone homeostasis, enhance bone formation and/or enhance bone repair may be desirable at least in that the dosage of each agent may be reduced as a result of the synergistic effects. In one example, BMP2 may be used for localized use in fracture healing studies. The dosages used vary depending on mode of delivery. For example, beads coated with 10-100 micrograms of BMP2 have been used in mouse bone fracture studies. In studies with monkeys, BMP7 has been used in dosages ranging from 500-2000 micrograms. In studies with dogs, BMP2 has been used between 200-2000 micrograms. In studies where BMP2 was delivered in a sponge implanted in the fracture site, the dosage used was 1.5 mg/ml. In a spinal fusion trial where fusion was achieved; a large dose of 10 mg of BMP2 was used. In a human study of tibial non-union fractures in humans, BMP7 was used at several mg dosages.

Additional classes of agents which may be useful in this invention alone or in combination with oxysterols include, but are not limited to cytochrome P450 inhibitors, such as SKF525A. Other classes of agents useful in the invention include phospholipase activators, or arachadonic acid. Other classes of agents useful in the invention include COX enzyme activators, or prostaglandins or osteogenic prostanoids. Other classes of agents useful in the invention include ERK activators.

The invention may include combination treatments with oxysterols and other therapeutics which affect bone formation, repair or homeostasis. For example, oxysterols in combination with bisphosphonates, hormone therapy treatments, such as estrogen receptor modulators, calcitonin, and vitamin D1 calcium supplementation, PTH (such as Forteo or teriparatide, Eli Lilly), sodium fluoride and growth factors that have a positive effect on bone, such as insulin-like growth factors I and II and transforming growth factor beta. Those skilled in the art would be able to determine the accepted dosages for each of the therapies using standard therapeutic dosage parameters.

The invention may include a method of systemic delivery or localized treatment with differentiated osteoblastic cells for maintaining bone homeostasis, enhancing bone formation and/or enhancing bone repair. This treatment may be administered alone or in combination with administration of other agent(s) to the patient, as described above. In one embodiment of this method, mammalian mesenchymal stem cells may be harvested, from the patient or a cell donor. The cells may then be treated with at least one agent to induce osteoblastic differentiation of the cells. The cells may then be readministered to the patient, either systemically or at a selected site at which bone homeostasis, bone formation or bone repair is desired. Additionally, the patient may by treated locally or systemically with at least one second agent which effects bone homeostasis, bone formation or bone repair.

In this aspect of the invention, marrow stromal cells (MSC) may be treated with an agent(s) to stimulate osteoblastic differentiation, as measured by any one of the increase in alkaline phosphatase activity, calcium incorporation, mineralization or osteocalcin mRNA expression, or other indicators of osteoblastic differentiation. In one embodiment of the invention MSC cells are harvested from a patient, treated with at least one oxysterol of the invention, and osteoblastic cells are administered to the patient.

The invention may include administering osteoblastically differentiated MSC systemically to the patient.

The invention may include placing osteoblastically differentiated MSC at selected locations in the body of a patient. In one embodiment of the invention, cells may be injected at a location at which bone homeostasis, formation and/or repair is desired.

In one application of the invention, the agents and methods may be applied to, but are not limited to the treatment or to slow the progression of bone related disorders, such as osteoporosis.

In applications of the invention, the agents and methods may be applied to, but are not limited to application of cells or agents to a surgical or fracture site, in periodontitis, periodontal regeneration, alveolar ridge augmentation for tooth implant reconstruction, treatment of non-union fractures, sites of knee/hip/joint repair or replacement surgery.

In one embodiment, the invention may include implants for use in the human body, comprising a substrate having a surface, wherein at least the surface of the implant includes at least one oxysterol of the invention in an amount sufficient to induce bone formation in the surrounding bone tissue, or the implant may include mammalian cells capable of osteoblastic differentiation, or osteoblastic mammalian cells, or a combination thereof for inducing bone formation or enhancing bone repair. For example, implants may include, but are not limited to pins, screws, plates or prosthetic joints which may be placed in the proximity of or in contact with a bone that are used to immobilize a fracture, enhance bone formation, or stabilize a prosthetic implant by stimulating formation or repair of a site of bone removal, fracture or other bone injury. The invention may also include the application of at least one agent or differentiated cells in the proximity of or in contact with a bone at a site of bone removal, fracture or other bone injury where bone formation or bone repair is desired.

Another embodiment of the invention is a kit useful for any of the methods disclosed herein, either in vitro or in vivo. Such a kit can comprise one or more of the oxysterols or pharmaceutical compositions discussed herein. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

In the foregoing and in the following examples, all temperatures are set forth in uncorrected degrees Celsius; and, unless otherwise indicated, all parts and percentages are by weight.

EXAMPLES

Example I

Materials and Methods

Many of the assays described below are conventional. Guidance for the performance of the assays can be found, e.g., in the commonly owned and published PCT international applications WO2004/019884, WO2005/020928, WO2005/020928; and WO2006/12902. See also Dwyer et al. (Jan. 2, 2007), *J. Biol. Chem*, Epub ahead of print; Parhami et al. (2002) *J. Bone Miner. Res.* 17; 1997-2003; Kha et al. (2004) *J Bone Miner Res.* 19, 830-840; Shouhed et al. (2005) *J Cell Biochem* 95, 1276-1283; Richardson et al. (2006) (*J Cell Biochem*, in press); and Aghaloo et al. (2006) *J Orthop Res*, in press).

Example II

Osteogenic and Anti-Adipogenic Activites of the Synthetic Oxysterols In Vitro

To test for osteogenic activity, synthetic oxysterols (e.g. analogues of 20S) are tested for their ability to act as inducers of osteoblastic differentiation in the absence of the stimulatory oxysterols, 22S/22R, and in comparison to when 20S is given in combination with these stimulatory oxysterols. We have previously reported that 20S acts to induce certain processes, such as bone morphogenesis, and that 22S and 22R can stimulate the activity of 20S (i.e., 22S and 22R are stimulatory oxysterols). Synthetic oxysterols that are derivatives of 20S (e.g., Oxy 13) mimic 20S and act as inducers, whereas synthetic derivatives of 22S (e.g., Oxy 3) act as stimulatory oxysterols.

The cells used are the pluripotent M2 cells (M2-10B4) that we previously characterized for their ability to become osteoblastiic and adipocyte cells. (See, e.g., Kha et al. (2004) *J Bone Miner Res* 19, 830-840). These cells are derived from bone marrow, are easy to maintain and last for many passages in vitro. The findings in M2 cells are confirmed in primary bone marrow stromal cells, which are isolated from C57BLK/6 mice and cultured by methods described in Kha et al. (2004), supra. Among the markers of osteogenic differentiation that were assayed were alkaline phosphatase activity, osteocalcin mRNA expression and mineral formation in cultures of marrow stromal cells.

We tested the effect of the synthetic oxysterols, oxy-1 through oxy-15, on alkaline phosphatase activity in M2-10B4 marrow stromal cells. Cells were treated with the oxysterols for 4 days after which they were collected and analyzed by colorimetric assay for alkaline phosphatase activity. Results from a representative experiment are shown as the fold induction in alkaline phosphatase activity compared to control untreated cells. Only the oxysterols that resulted in a measurable induction are shown.

| Oxysterol | Fold Induction over Control Untreated Cells |
| --- | --- |
| Oxy7 (5 µM) | 9 |
| Oxy7 (10 µM) | 23 |
| Oxy9 (5 µM) | 2 |
| Oxy9 (10 µM) | 4 |
| Oxy11 (2.5 µM) | 6 |
| Oxy12 (5 µM) | 22 |
| Oxy12 (10 µM) | 80 |
| Oxy13 (2.5 µM) | 200 |
| Oxy13 (5 µM) | 334 |
| Oxy14 (2.5 µM) | 42 |
| Oxy14 (5 µM) | 100 |
| Oxy15 (5 µM) | 55 |
| Oxy15 (10 µM) | 80 |

We tested the effect of oxysterols on mineralization in M2-10B4 marrow stromal cells. Cells were treated with the oxysterols for 14 days after which the amount of mineral formed in the cultures was quantified using a radioactive $^{45}$Ca incorporation assay. Results from a representative experiment are shown as the fold induction in cpm/mg protein compared to control untreated cells. Only the oxysterols that resulted in a measurable calcium incorporation are shown.

| Oxysterol | $^{45}$Ca Incorporation (fold induction over control untreated cells) |
| --- | --- |
| 20S (7.5 µM) | 4 |
| Oxy3 (5 µM) + 20S (7.5 µM) | 8 |
| Oxy4 (5 µM) + 20S (7.5 µM) | 7 |
| Oxy7 (5 µM) + 20S (7.5 µM) | 5 |
| Oxy12 (5 µM) | 2 |
| Oxy12 (10 µM) | 4 |
| Oxy12 (15 µM) | 7 |
| Oxy13 (5 µM) | 5 |
| Oxy13 (10 µM) | 34 |
| Oxy13 (15 µM) | 38 |
| Oxy14 (10 µM) | 4 |

Other conventional in vitro assays that serve as markers for osteoblastic differentiation are also tested with the oxy compounds of the invention. These assays include, e.g., detection of an increase (compared to a baseline value or control) in calcium incorporation or the expression of osteocalcin mRNA.

Figure 1:
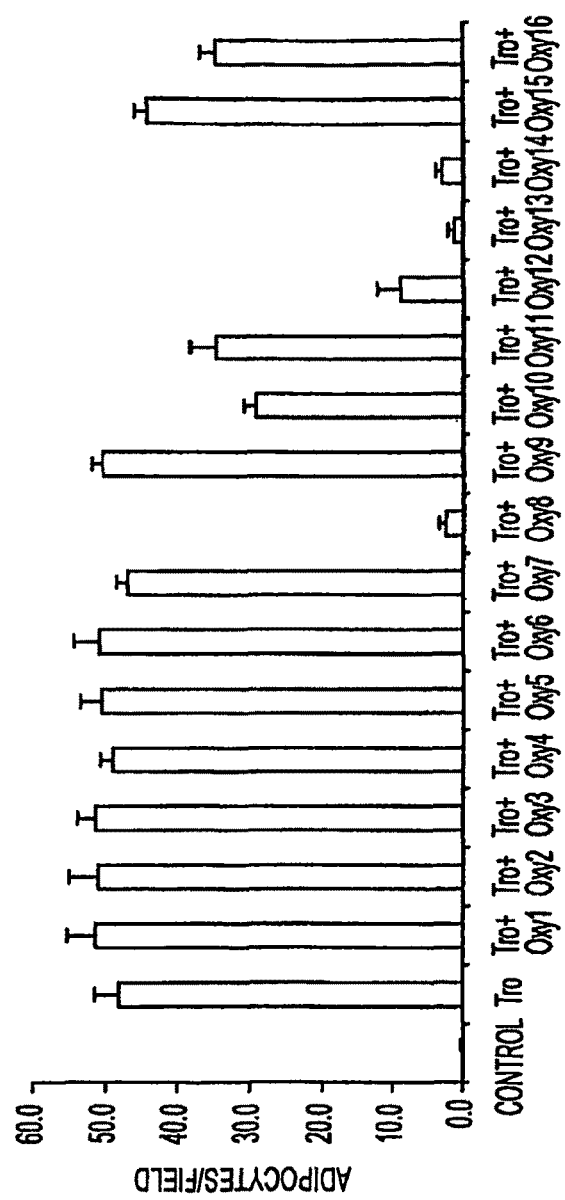
FIG. 1 shows the effect of different synthetic oxysterols on adipogenic differentiation.

We tested the effects of different synthetic oxysterols (oxy 1-16) on adipogenic differentiation. The results are shown in FIG. 1. M2-10B4 bone marrow stromal cells were treated with control vehicle or the PPARgamma activator, troglitazone (Tro, 10 µM), in the presence or absence of various oxysterols (5 µM) as indicated. After 10 days of treatment, cells were stained with oil-red-O to detect adipocytes, and the number of positively stained cells was determined using light microscopy. Data from a representative experiment are reported as the mean of triplicate determination (average of five fields per well, 3 wells per experimental condition)±SD.

Example III

Mechanisms of Action of Oxysterols for Stimulating Osteoblastic Differentiation

We previously demonstrated that certain osteogenic oxysterols induce Runx2 DNA binding activity; that they can act synergistically with BMPs, including BMP2, BMP 7 and BMP 14/GDF-5; and that they inhibit the adverse effects of oxidative stress on osteogenic differentiation of MSC. See, e.g., WO2004/019884, WO2005/020928, WO2005/020928; and WO2006/12902 for guidance as to how to carry out these and other assays.

The novel oxysterols of the invention are tested by the same methods. Those oxysterols that have been shown to be osteogenic are expected to function via the same mechanisms as the previously tested oxysterols.

Example IV

In Vivo Osteogenic Effects of Oxysterols

We previously demonstrated that certain naturally occurring osteogenic oxysterols enhance bone healing when implanted into rat calvarial critical-sized defects. See, e.g., the commonly owned and published PCT international applications WO2004/019884, WO2005/020928, WO2005/020928; and WO2006/12902 for guidance as to how to carry out these and other assays.

Synthetic oxysterols of the inventions are tested in the rat calvarial bone formation model, as well as in two additional in vivo models. The synthetic oxysterols are tested individually, or in combinations, in the absence of the stimulatory oxysterols 22S/22R, and in comparison to when 20S is administered in combination with these stimulatory oxysterols. The first of the additional models is the widely used and FDA-approved ovariectomy model in which the ovaries in a female mouse are removed, resulting in rapid loss of bone. The inhibition of the bone loss is evaluated following the systemic administration of test oxysterols (putative anabolic oxysterols); the assessment is performed by microCT analysis and histological studies. The second model is the widely used long bone critical defect model, in which a defect is surgically created in the femur or tibia of a rat, followed by implantation of test oxysterols (putative osteoinductive agents) and the radiographic and histological assessment of the rate and quality of bone formation in the healing bond in tested vs. treated animals. It is expected that those synthetic oxysterols that elicit osteogenic effects in vitro will also stimulate bone healing in these in vivo models.

M2 cells or primary bone marrow stromal cells are treated with the individual 20S analogues at doses of 0.5-15 µM based on our experience with the parent compound, 20S. We take a systematic approach in testing osteoblastic differentiation of MSC in response to oxysterol analogues by examining the expression of a spectrum of early and late markers of osteoblastic differentiation. Parallel cultures are set up and tested for early markers of osteogenic differentiation: alkaline phosphatase activity, Runx2 DNA binding activity, and collagen I mRNA expression, and late markers of osteogenic differentiation: bone sialoprotein and osteocalcin mRNA expression by quantitative RT-PCR. Induction of mineralization is also tested using a $^{45}$Ca incorporation assay and von Kossa staining, as described in Kha et al. (2004) (supra). Early markers are tested after 3 days of treatment with the oxysterols, late markers after 8 days, and mineralization after 14 days of treatment with the test oxysterols. These time points are based on our experience with the regulation of markers of osteogenic differentiation by osteoinductive agents in M2 cells.

Effects of Oxy13 in the Rat Femur Periosteum Model

The preceding demonstrations that naturally occurring oxysterols exhibit in vivo osteogenic effects, and that the certain synthetic oxysterols of the invention exhibit properties in vitro that are markers for in vivo bone growth, were confirmed using a rat femur periosteum model, which is described in Yoshia et al., PNAS, 99:4580 (2002).

Male SD rats were treated for two weeks with Oxy13 (or a control vehicle). The Oxy13 was delivered by an Alzet pump to the perioseum, in three doses or by daily injections. The treatment regimens were: two weeks treatment, n=6 per group, vehicle and three Oxy 13 doses continuous and two doses daily injection; and four weeks treatment, vehicle and two Oxy 13 doses, n=6/group. The bone in-growth endpoints that were evaluated were microradiography, histomorphometry and blinded, randomized visual scoring.

Other endpoints are evaluated, including plasma samples at time of sacrifice for biomarkers and immunohistochemistry. Other oxysterols of the invention are also tested.

Table 1 shows the scoring criteria in the Rat Periosteal Femur Model

TABLE 1

| Characteristic | Grading | Score |
|---|---|---|
| Amount of periosteal bone formation | Marked amount and contiguous on eriosteum | 4 |
| | Moderate amount and contiguous on eriosteum | 3 |
| | Small amount and contiguous on periosteum | 2 |
| | Small amount and small segments on periosteum | 1 |
| | None | 0 |
| | Maximum | 4 |

Table 2 shows the bone formation scoring from the experiment with the 2 weeks of pump administration:

TABLE 2

| Animal ID | Score | Average | St. dev | Treatment Group | Treatment Description |
|---|---|---|---|---|---|
| 5854 | 4 | 3.00 | 1.26 | 1 | Pump 2 wk 1.67 |
| 5844 | 4 | | $P < 0.05*$ | | mg/ml OXY13 |
| 5886 | 3 | | | | |
| 5836 | 4 | | | | |
| 5858 | 2 | | | | |
| 5888 | 1 | | | | |
| 5863 | 3 | 3.00 | 0.00 | 2 | Pump 2 wk 0.167 |
| 5839 | 3 | | | | mg/ml OXY13 |
| 5877 | 3 | | | | |
| 5873 | 3 | | | | |
| 5874 | 3 | | | | |
| 5870 | 3 | | | | |
| 5887 | 2 | 1.67 | 0.82 | 3 | Pump 2 |
| 5869 | 3 | | | | wk Vehicle |
| 5835 | 1 | | | | |
| 5878 | 1 | | | | |
| 5867 | 1 | | | | |
| 5885 | 2 | | | | |

*Non parametric analysis - Kruskal Wallis with Dunn's post test

FIG. 7 shows graphically the bone formation scoring for rats treated with Oxy13 for two weeks (pump administration) in a rat periosteal femur model.

Table 3 shows the bone formation scoring (radiograph scoring) from the experiment with the 4 weeks of pump administration:

TABLE 3

| Animal ID | Score | Average | Stdev | Treatment Group | Treatment Description |
|---|---|---|---|---|---|
| 5884 | 2 | 1.50 | 1.05 | 4 | 4 wk OXY13 |
| 5843 | 3 | | | | Pump 1.67 mg/ml |
| 5860 | 1 | | | | |
| 5883 | 0 | | | | |
| 5853 | 1 | | | | |
| 5861 | 2 | | | | |
| 5847 | 0 | 2.00 | 1.10 | 5 | Pump 4 wk 0.167 |
| 5848 | 2 | | $P < 0.05*$ | | mg/ml OXY13 |
| 5841 | 3 | | | | |
| 5856 | 2 | | | | |
| 5842 | 3 | | | | |
| 5840 | 2 | | | | |
| 5871 | 0 | 0.67 | 0.52 | 6 | Pump 4 |
| 5832 | 0 | | | | wk Vehicle |
| 5872 | 1 | | | | |
| 5851 | 1 | | | | |
| 5889 | 1 | | | | |
| 5862 | 1 | | | | |

*Non parametric analysis - Kruskal Wallis with Dunn's post test

FIG. 8 shows graphically the bone formation scoring for rats treated with Oxy13 for four weeks (pump administration) in a rat periosteal femur model.

Example V

In Vivo Anti-Adipogenic Effects of Oxysterols

We previously reported that both the inducer oxysterol, 20S, and the stimulatory oxysterols 22S and 22R, inhibit the adipogenic differentiation of M2 cells. Without wishing to be bound by any specific mechanism, this appears to suggest that the mechanism by which these oxysterols inhibit adipogenic differentiation might be distinct from that which induces osteogenic differentiation, and that therefore even some of the analogues that may be inactive in our osteoinductive tests may still inhibit adipogenesis. M2 cells are treated with PPARγ agonist, troglitazone (Tro) at 10 μM which induces adipogenesis in a variety of pluripotent cells including the M2 marrow stromal cells. The synthetic analogues are tested by treating M2 cells with Tro in the absence or presence of the individual oxysterols. After 8 days of treatment, at which time fully formed adipocytes are produced in M2 cultures treated with Tro, oil red O staining is performed to detect adipocytes that stain red due to the accumulation of neutral lipids. Adipocyte numbers are quantified by counting fields under a phase contrast microscope by conventional procedures. Those oxysterols that exhibit anti-adipogenic effects in vitro are also expected to inhibit adipogenesis in vivo.

Example VI

Effect of Oxysterols on Hair Growth in Mice

The study showed that one topical application of a combination of 20(S)-hydroxycholesterol+22(S)-hydroxycholesterol at 50 μg, 100 μg and 150 μg of each oxysterol (1:1) delivered in a vitamin E solution enhanced hair growth on a 2 cm×2 cm shaved area on the back of C57BL/6 mice during an 18 day observation period.

Synthetic oxysterols of the invention are tested in the same model. Oxysterols that stimulate the hedgehog pathway or a markers there of are also expected to stimulate hair growth in this model.

Example VII

Role of the Hedgehog Pathway in Mediating the Osteoinductive Effects of the Oxysterols 20S+22S Pluripotent mesenchymal cells form a population of precursors to a variety of cell types including osteoblasts and adipocytes. Aging tilts the balance in favor of adipocyte differentiation at the expense of osteoblast differentiation, resulting in reduced bone formation and osteopenic disorders, including osteoporosis, in humans and animals. In this Example, we report that specific, naturally-occurring oxysterols, previously shown to direct pluripotent mesenchymal cells toward an osteoblast lineage, exert their osteoinductive effects through activation of Hedgehog, signaling pathway. This was demonstrated by 1) oxysterol-induced expression of the Hh target genes Gli-1 and Patched, 2) oxysterol-induced activation of a luciferase reporter driven by a multimerized Gli-responsive element, 3) inhibition of oxysterol effects by the hedgehog pathway inhibitor, cyclopamine, and 4) unresponsiveness of Smoothened−/− mouse embryonic fibroblasts to oxysterols. Using Patched−/− cells that possess high baseline Gli activity, we found that oxysterols did not dramatically shift the IC50 concentration of cyclopamine needed to inhibit Gli activity in these cells. Furthermore, binding studies showed that oxysterols did not compete with fluorescently labeled cyclopamine, BODIPY-cyclopamine, for direct binding to Smoothened. These findings demonstrate that oxysterols stimulate hedgehog pathway activity by indirectly activating the seven-transmembrane pathway component Smoothened. Osteoinductive oxysterols are therefore novel activators of the hedgehog pathway in pluripotent mesenchymal cells.
Materials and Methods
  Cell Culture and Reagents—
  M2-10B4 cells, C3H10T½ cells, Smo−/− mouse embryonic fibroblasts (MEFs) and Ptch−/− MEFs were maintained by conventional procedures. Treatments were performed in differentiation medium containing 5% fetal bovine serum, 50 µg/ml ascorbate and 3 mM β-glycerophosphate. Oxysterols and Phorbol 12-Myristate 13-Acetate (PMA) were obtained from Sigma-Aldrich, Co. (St. Louis, Mo.), cyclopamine and KAAD-cyclopamine were from EMD Biosciences, Inc. (La Jolla, Calif.), recombinant mouse Shh amino terminal peptide and Shh neutralizing antibody were from R&D Systems, Inc. (Minneapolis, Minn.), rottlerin and H-89 were from Calbiochem (La Jolla, Calif.), and all antibodies for Western blotting were from Cell Signaling Technology (Danvers, Mass.). The plasmid pACMV-tetO and HEK293S-TetR cells were gifts from P. J. Reeves and H. G. Khorana (University of Essex, Colchester, UK). The polyclonal anti-Myc antibody was from Santa Cruz Biotechnology and the enhanced chemiluminescence detection kit was from Amersham Pharmacia. BODIPY-cyclopamine was from TRC (North York, Ontario, Canada), tetracycline was purchased from Sigma, and sodium butyrate was from J. T. Baker (Mallinckrodt Baker, Phillipsburg, N.J.). Blasticidin and Geneticin were from Invitrogen (Carlsbad, Calif.).

Microarray—
  All samples were processed, scanned and quality checked on Affymetrix HG-U133A arrays. For analysis of gene expression measures, all Affymetrix data was normalized using model-based expression and the pair matched-mismatched method from dChip (Li et al. (2003) in *The Analysis of Gene Expression Data: Materials and Software* (Parmgiani et al. eds), pp. 120-141, Springer, New York). Subsequent to this, probe sets that showed at least a 2 fold change in expression, a minimum difference in expression of 100, and a 2 sided t-test p-value of <0.01 between the two groups were selected out for further analysis. Comparisons were made for all experimental vs. all control, and also for experimental vs. control comparisons at 8 and 48 hour time points specifically. The lists generated in this way were then put through an EASE analysis (Hosack et al. (2003) *Genome Biol.* 4, R70) to test for enrichment of gene ontology terms. EASE analysis indicated an enrichment in terms for steroid metabolism in the 8 hour comparison, and for an enrichment of morphogenesis and developmental terms in the 48 hour comparison.
  Quantitative Real-Time PCR (Q-RT-PCR)—
  Q-RT-PCR was performed using reverse-transcribed RNA isolated from M2 cells using phenol/chloroform method. PCR reactions were performed using iQ SYBR Green Supermix and an iCycler RT-PCR Detection System (BIO-RAD Laboratories, Hercules, Calif.). Primer sequences for Gli-1, Gli-2, Gli-3, Shh and Ihh were kindly provided by Dr. Fanxin Long (Washington University, St. Louis, Mo.). Ptch and Smo primer sequences are available upon request. Q-RT-PCR data were normalized to cyclophilin expression and relative expression levels were calculated using the $2^{\Delta\Delta C_T}$ method (Livak et al. (2001) Methods 25, 402-408).
  Transient Transfection—
  Cells were plated into 24-well plates and transfected the next day with Gli-dependent firefly luciferase and Renilla luciferase vectors and where indicated, Smo or Ptch expression vectors. Total DNA per well did not exceed 500 ng and FuGENE 6 Transfection Reagent (Roche, Indianapolis, Ind.) was used at a ratio of 3:1 (reagent:DNA). Cells were treated for 48 hours prior to assessing luciferase activity using the Dual Luciferase Reporter Assay System (Promega, Madison, Wis.) according to manufacturer's instructions. Experiments were performed in triplicate and error bars indicate one standard deviation.
  Electromobility Shift Assay (EMSA)—
  The sequence of the OSE2 oligonucleotide was (5'-AGCTG CAATC ACCAACCACA GCA-3') (SEQ ID NO:1). Oligonucleotides were annealed to their complementary sequences by boiling and cooling. The probes were end-labeled with $\gamma^{32}$P-ATP using polynucleotide kinase and column purified. Nuclear extracts were prepared using the modified Dignam protocol (Osborn et al. (1989) *Proc. Natl. Acad. Sci. USA* 86. 2336-2340). Nuclear extracts (10 µg) were incubated in binding buffer (10 mM Tris pH 7.5, 100 mM NaCl, 1 mM DTT, 1 mM EDTA, 4% glycerol), 1 µg poly(dIdC) and 0.2 ng of labeled probe for 20 minutes at room temperature, and complexes were resolved on a cooled, 6% acrylamide 1×TBE gel. Subsequently, gels were dried and exposed to film.
  Alkaline Phosphatase Activity Assay, Northern Blotting and Mineralization Assay—
  Colorimetric alkaline phosphatase activity assay on whole cell extracts and Northern blotting for OCN and 18S rRNA were performed by conventional procedures. Gene expression was quantified using a Storm840 phosphorimager and ImageQuant software (Amersham, Piscataway, N.J.).

Construction of the Tetracycline-Regulated Smo Expression Plasmid, pACMV-tetO-Smo-Myc—

The Smo-Myc gene was amplified from the plasmid pGE-Smo-Myc (Taipale et al. (2002) Nature 418, 892-897) using the primers 5'-AAAAT GAATT CAACA ACTCC GCCCC ATTGA C-3'(SEQ ID NO:2) and 5'-CCCGC GCGGC CGCCG ACTAC GACCT AATTC CTGC-3' (SEQ ID NO:3). The resulting PCR product was digested with HindIII to isolate the Smo-Myc gene, end-repaired by using the DNA polymerase I Klenow fragment, and then digested with NotI. The Smo-Myc gene was purified by agarose gel electrophoresis and inserted into the plasmid pACMV-tetO, as previously described (Reeves et al. (2002) Proc. Natl. Acad. Sci. USA 99, 13413-13418 28), to give the vector pACMV-tetO-Smo-Myc.

Construction of Stable HEK293S Cell Lines for Tetracycline-Induced Smo Gene Expression—

HEK293S-TetR cells were maintained and stably transfected with pACMV-tetO-Smo-Myc as described (Reeves et al. (2002) (supra). Individual Geneticin-resistant colonies were expanded and screened for Smo-Myc expression by analyzing solubilized cell extracts by SDS-PAGE followed by immunodetection with anti-Myc polyclonal antibody. One cell line exhibiting tetracycline-inducible Smoothened expression was chosen and expanded for use in all subsequent experiments.

BODIPY-cyclopamine Binding Assay—

HEK293S stable cell lines containing the inducible Smoothened gene were grown to confluence in medium containing Geneticin (2 mg/ml) by using 6-well plates. The growth medium was then replaced with fresh medium containing tetracycline (1 µg/ml) and sodium butyrate (5 mM). After 2 d, fluorescence binding assays using BODIPY-cyclopamine were conducted as previously described (Chen et al. (2002) Genes Dev. 16, 2743-2748).

Western Blotting—

After treatments, cells were lysed in lysis buffer, protein concentrations determined using the Bio-Rad protein assay (Hercules, Calif.), and SDS-PAGE was performed, probing for native and phosphorylated proteins.

Statistical Analyses—

Computer-assisted statistical analyses were performed using the StatView 4.5 program. All p-values were calculated using ANOVA and Fisher's projected least significant difference (PLSD) significance test. A value of p<0.05 was considered significant.

Results

Hedgehog Pathway Activation by Osteogenic Oxysterols—

Figure 2A:
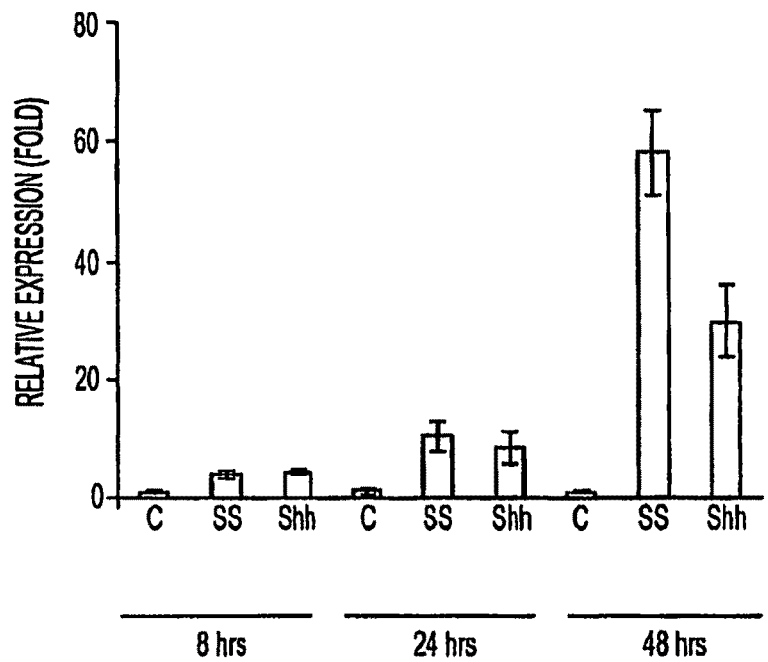
FIG. 2 shows that osteogenic oxysterols activate the Hedgehog (Hh) pathway. Quantitative Real-Time PCR (Q-RT-PCR) of mRNA from M2 cells treated with control vehicle (C), 5 µM of a combination of 20(S)-hydroxycholesterol and 22(S)-hydroxycholesterol in a ratio of 1:1 (SS)
Figure 2B:
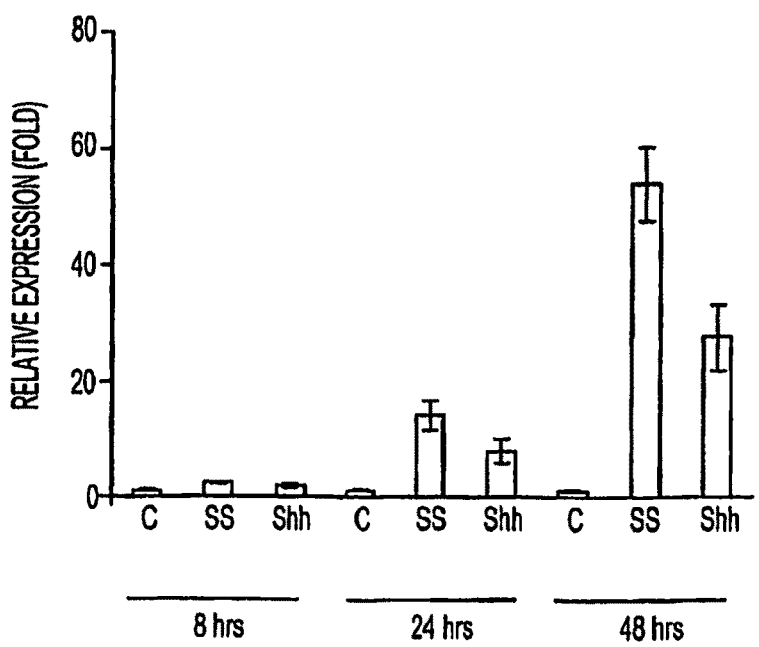

In order to elucidate the molecular mechanisms involved in the osteoinductive effects of oxysterols, we performed a microarray based gene expression analysis using Affymetrix mouse 430A gene chips comparing mRNA expression in the pluripotent mouse marrow stromal cell line M2-10B4 (M2) following treatment with control vehicle or an optimum dose of the oxysterol combination, 20(S)- and 22(S)-hydroxycholesterol (SS) (5 µM, 1:1) for 8 and 48 hours. Relative to vehicle-treated controls, oxysterol treatment induced expression of the Hh target genes Gli (GLI-Kruppel family member GLI, NM_010296) (3.3-fold induction at 8 hours, p=0.0008, and 14-fold induction at 48 hours, p=0.0002) and Ptch (patched homolog, NM_008957) (38-fold induction at 48 hours, p=0.0001, with no apparent induction at 8 hours) relative to vehicle treated controls. Q-RT-PCR analysis confirmed these findings and demonstrated a robust increase in Gli-1 expression at 8, 24 and 48 hours, and in Ptch expression at 24 and 48 hours (FIGS. 2a and 2b). No significant changes were found in Gli-2 or Gli-3 gene expression at these timepoints (data not shown). Cells showed similar responses with a recombinant form of the mouse Shh amino-terminal signaling domain (ShhN) (FIGS. 2a and 2b).

Figure 2C:
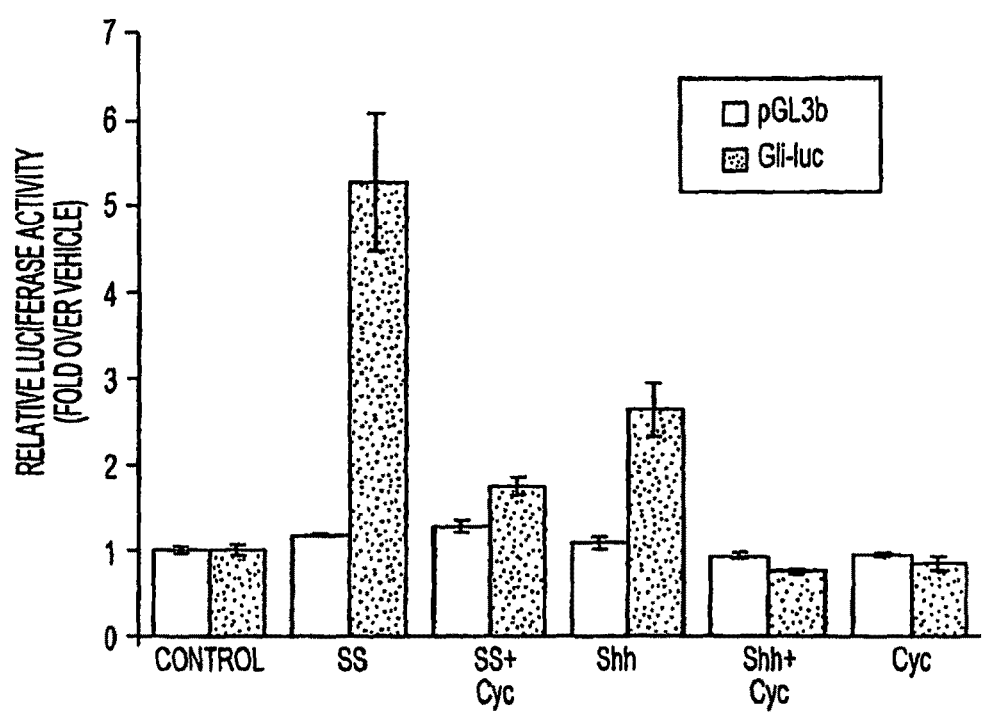

To further examine Hh pathway activation by oxysterols, a reporter assay using a luciferase reporter driven by a multimerized Gli-responsive element (5'-GAACACCCA-3') (SEQ ID NO:4) was used. M2 cells transfected with Gli-luc and treated with SS showed a 5-fold increase in luciferase activity over control vehicle-treated cells (FIG. 2c). Similar results were noted upon treatment of cells with ShhN (200 ng/ml), and induction by oxysterols or ShhN was inhibited by pre-treatment with the Hh pathway inhibitor, cyclopamine. Induction of Gli reporter activity was not observed for non-osteoinductive oxysterols, including 7-α-hydroxycholesterol and 7-ketocholesterol (FIG. 2d), thus further supporting a role for Hh pathway activity in oxysterol-induced osteogenesis.

Role of Liver X Receptor in Hh Pathway Activation—

Figure 2D:
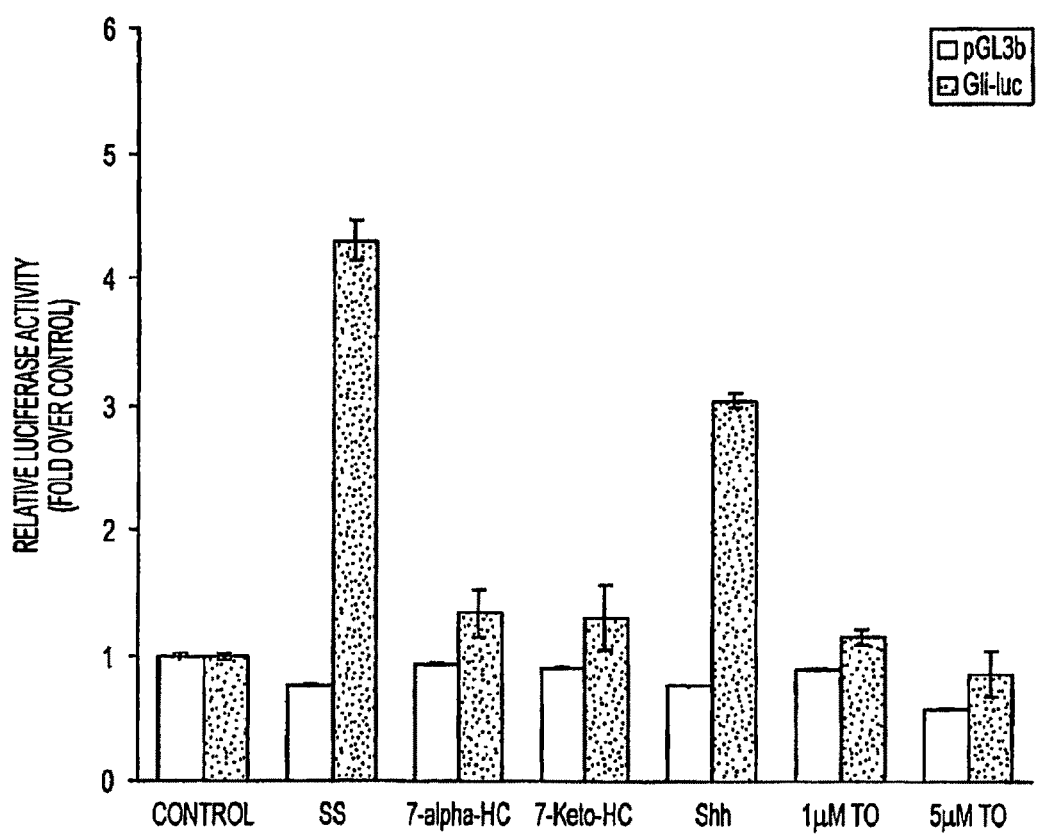

As specific oxysterols, including 20S and 22R, are known agonists of the nuclear hormone receptor liver X receptor (LXR), and since LXR is expressed in M2 cells, we examined whether activation of LXR could lead to increased Hh signaling. Gli-luc reporter assay showed no activation in cells treated with 1 or 5 µM of the synthetic LXR agonist, TO-901317 (TO) (FIG. 2d). This is consistent with our previous finding that activation of LXR in M2 cells by similar concentrations of TO does not induce, but actually inhibits osteoblastic differentiation. Such potentially adverse activation of LXR by osteoinductive oxysterols, such as 20S, emphasizes the importance of developing strategies that would limit its concentration if used therapeutically for osteopenic disorders. Combination oxysterol treatment using 20S with 22S, which is not an LXR agonist and appears to enhance the osteoinductive effects of 20S, is one such strategy.

Hh Pathway Activation Mediates Oxysterol-Induced Osteoblastic Differentiation—

Figure 3A:
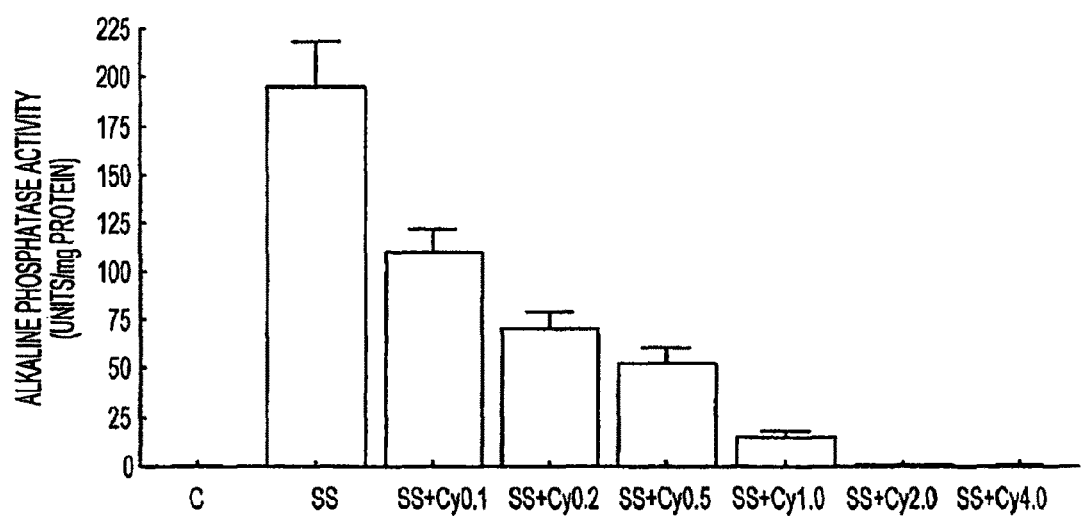
Figure 3B:
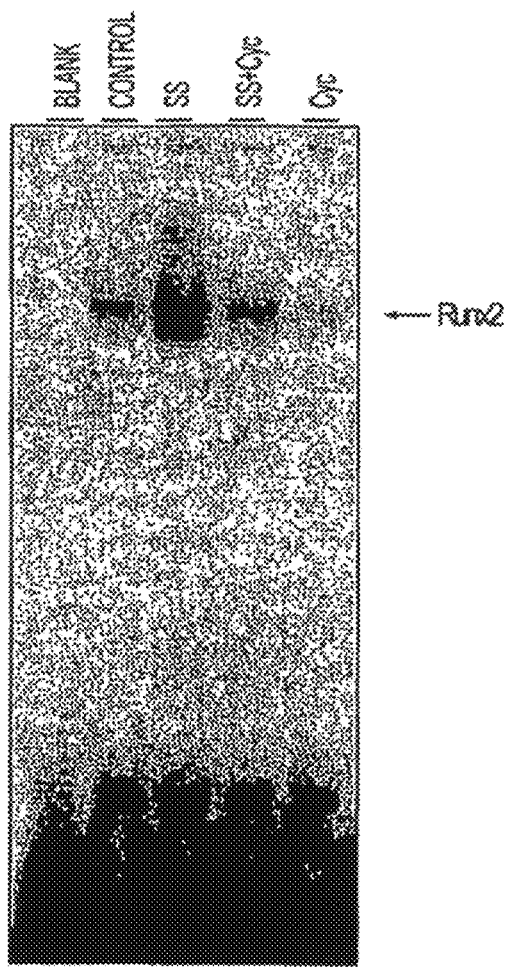
Figure 3C:
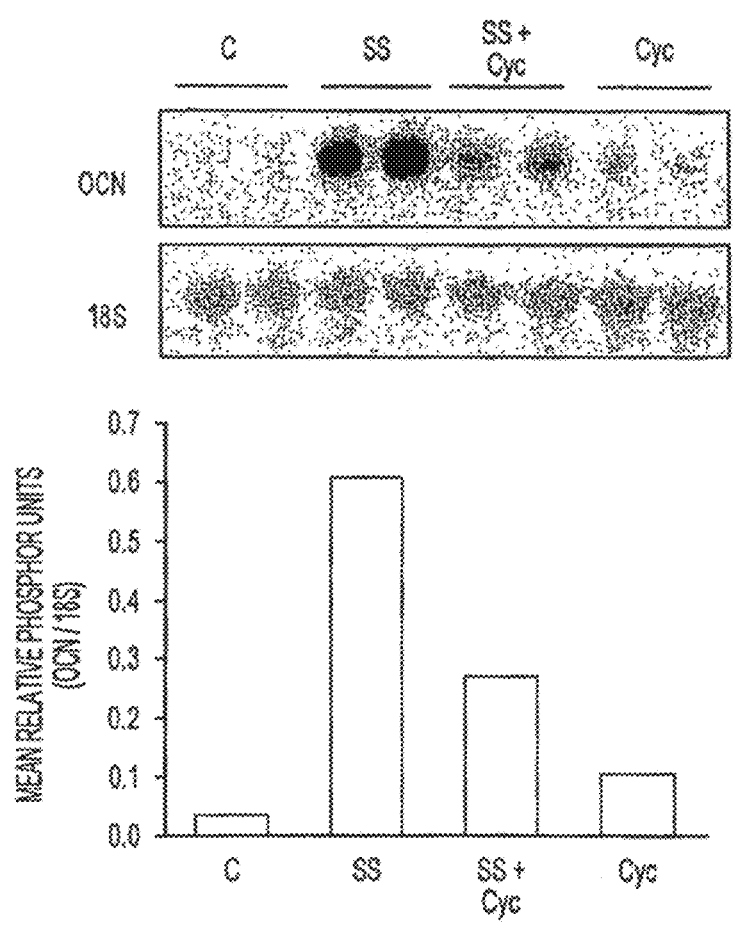
Figure 3D:
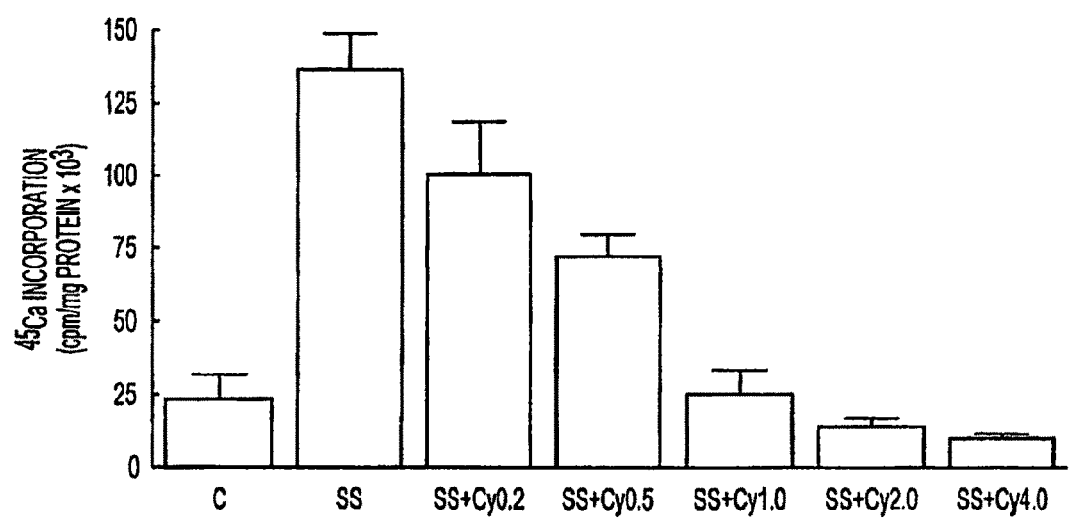

To determine the functional role of Hh signaling in oxysterol-induced osteoblastic differentiation, the effect of cyclopamine on oxysterol-induced markers of osteoblastic differentiation in M2 cells was evaluated. We found that the substantial induction in ALP activity produced by SS treatment was significantly inhibited by cyclopamine in a dose-dependent manner (FIG. 3a). Similarly, EMSA analysis demonstrated that cyclopamine completely inhibited the stimulation of Runx2 DNA binding activity in oxysterol-treated cells (FIG. 3b). Furthermore, oxysterol-induced expression of OCN, a Runx2 target gene, and increased mineralization in cultures of M2 cells, were inhibited by cyclopamine (FIG. 3c,d). Altogether, these findings demonstrate that the Hh signaling pathway is essential for the osteoinductive effects of oxysterols.

Mechanism of Oxysterol-Induced Hh Pathway Activation—

To elucidate the mechanism by which oxysterols cause Hh pathway activation, we first examined whether oxysterols induce the expression of endogenous Hh molecules by M2 cells. Q-RT-PCR analysis showed that oxysterol treatment (5 µM SS) of M2 cells for up to 48 hours produced no change in the low levels of Ihh mRNA present in vehicle-treated control cells, and that Shh mRNA in M2 cells was undetectable with or without oxysterol treatment (data not shown). Furthermore, a Shh neutralizing antibody did not inhibit oxysterol-induced ALP activity in M2 cells, whereas it completely inhibited ALP activity induced by exogenously added ShhN (Figure). These results suggest that oxysterols do not affect endogenous Rh expression levels and must therefore cause Hh pathway activation via a different mechanism, perhaps by modulating other members of the Hh signaling network such as Smo and/or Ptch.

Figure 5A:
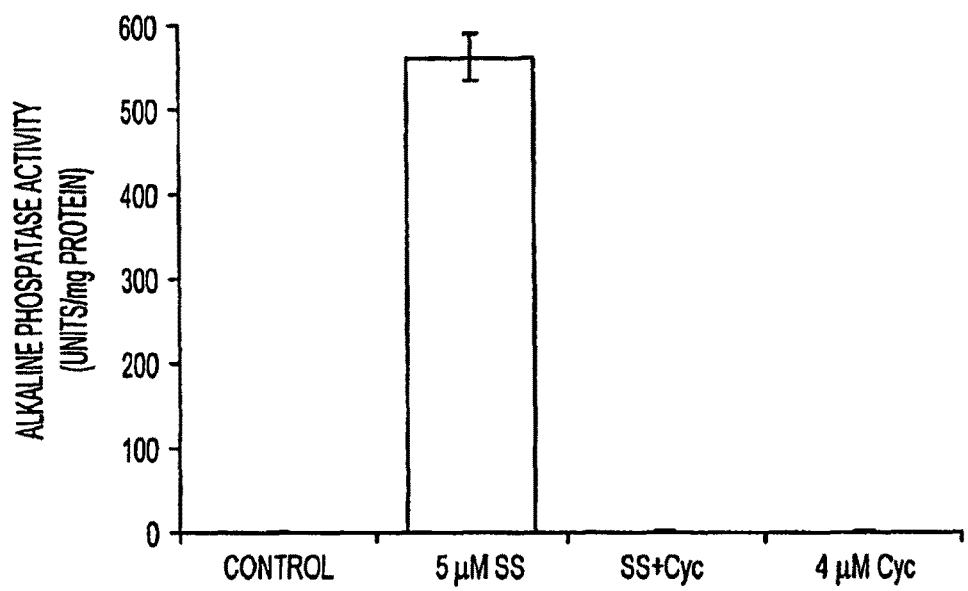
Figure 5B:
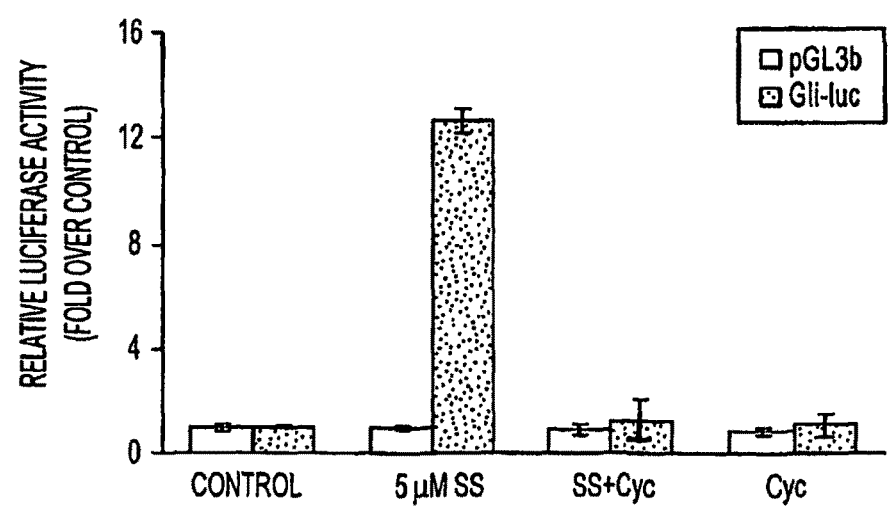
Figure 5C:
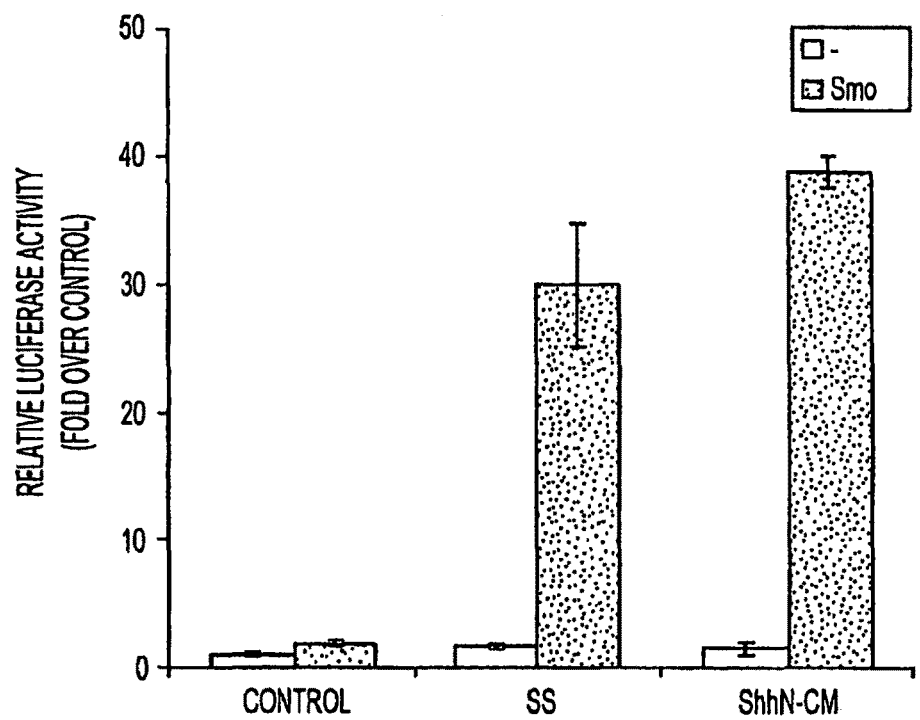
Figure 5D:
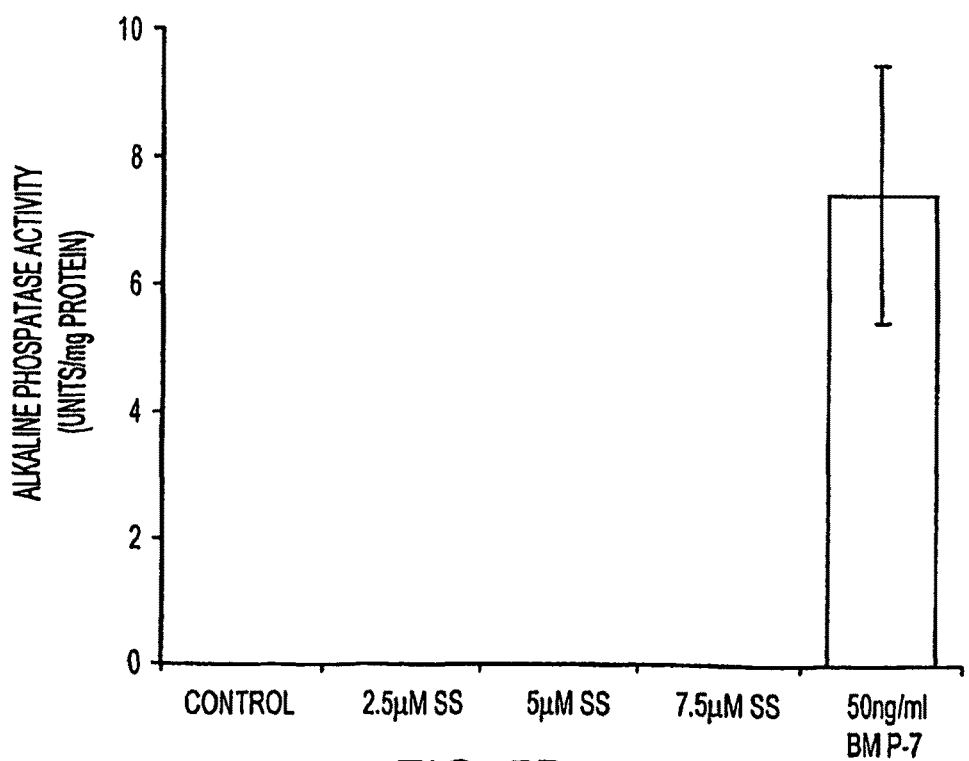
Figure 5E:
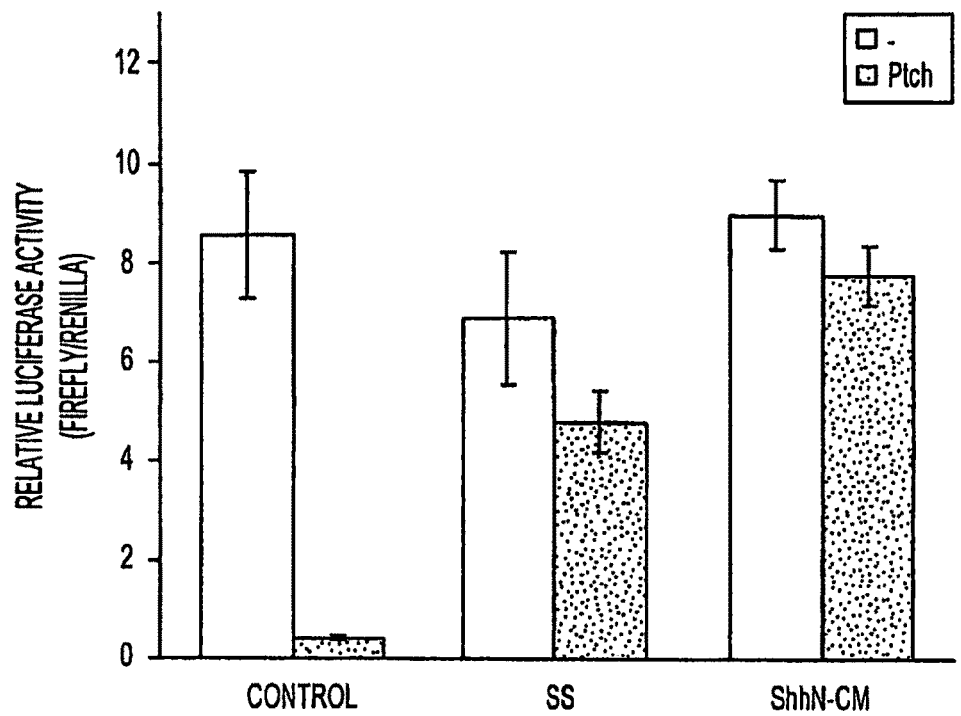

To examine this possibility, mouse embryonic fibroblasts from Smo−/− and Ptch−/− null mice were used. To demonstrate that MEFs from mutant mouse embryos are an appropriate model system to further characterize the mechanism of oxysterol-induced Hh pathway activity, we first tested the effects of osteogenic sterols on wild-type C3H10T½ MEFs. Similar to the pluripotent marrow stromal cells, we found that C3H10T½ cells undergo osteoblastic differentiation in response to oxysterols, as assessed by the induction of ALP activity (FIG. 5a) and Runx2 DNA binding activity. Treatment with oxysterols also induced Gli-luc activity in C3H10T½ cells and this activity was inhibited by cyclopamine pre-treatment (FIG. 5b). In contrast to wild type MEFs, Smo−/− MEFs had very low Gli-luc activity and were unresponsive to treatment with oxysterols or with conditioned medium containing ShhN (ShhN-CM) (FIG. 5c). Responsiveness to SS and ShhN-CM was restored by transfection of a Smo expression vector, with no change in baseline reporter activity (FIG. 5c). Smo−/− MEFs also failed to undergo osteoblastic differentiation in response to oxysterols (FIG. 5d), although treatment with bone morphogenetic protein 7 (BMB-7), did induce ALP activity in Smo−/− MEFs, thus bypassing the requirement for Hh pathway activity and confirming the inherent ability of these cells to differentiate along the osteoblastic lineage (FIG. 5d). Studies using Ptch−/− MEFs, in which baseline Hh pathway activity is high due to constitutive Smo activity, demonstrated that neither oxysterols nor ShhN-CM induced further pathway activation (FIG. 5e). Reintroduction of Ptch into Ptch−/− cells re-established Smo regulation, reduced baseline Hh pathway activity, and restored sensitivity to oxysterols and ShhN-CM in pathway activation (FIG. 5e). These results indicate that oxysterol induction of Hh pathway activity requires Smo, and that further activation by oxysterols does not occur when Smo is fully active due to loss of Ptch.

Figure 5F:
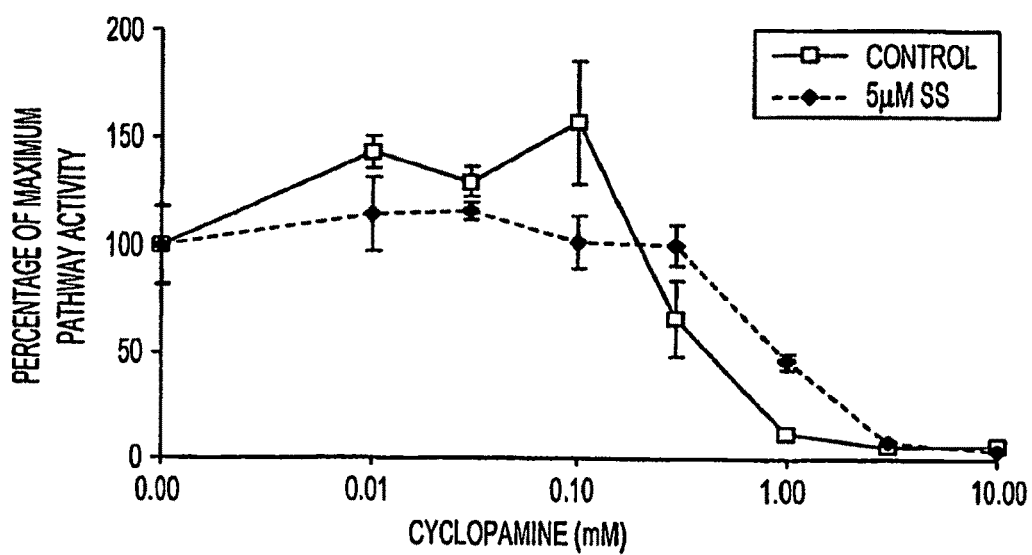
Figure 5G:
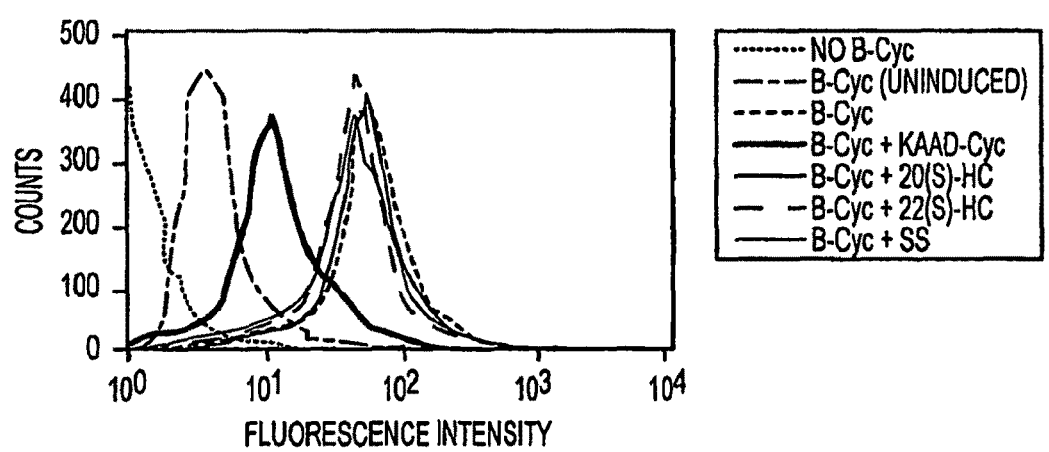

We next examined the possibility that oxysterols may stimulate Hh pathway activity by directly binding to and activating Smo, as previously demonstrated for pathway agonists Smo agonist (SAG) and purmorphamine. Gli-luc reporter activity in Ptch−/− MEFs can be suppressed in a dose-dependent manner by treatment with the Smo antagonist cyclopamine, which acts by directly binding to and inhibiting Smo (FIG. 5f). If oxysterols act by binding to and activating Smo, then a shift in the effective concentration of cyclopamine required for pathway inhibition would be expected. For example, the IC50 of cyclopamine action is shifted by several orders of magnitude upon treatment with Hh pathway-activating concentrations of the Smo agonists SAG and purmorphamine. We noted, however, that oxysterols did not cause dramatic shifts in the concentrations of cyclopamine required to inhibit Gli-luc activity in Ptch−/− MEFs (FIG. 5f), suggesting that oxysterol action is not directly antagonistic to that of cyclopamine. Furthermore, we tested whether oxysterols can compete for binding of a fluorescent derivative of cyclopamine, BODIPY-cyclopamine (B-cyc), to cells expressing Smo. Following induction of Smo expression in HEK293S cells stably transfected with an inducible Smo expression construct, cells were co-treated with oxysterols or the potent cyclopamine derivative KAAD-cyclopamine in the presence of B-cyc and subjected to fluorescence activated cell sorting (FACS) analysis. We found that binding of B-cyc to HEK293S cells overexpressing Smo was not affected by SS, whereas KAAD-cyclopamine dramatically reduced B-Cyc binding (FIG. 5g).

The Role of Protein Kinase C and Protein Kinase A in Oxysterol-Induced Hh Pathway Activation—

Figure 6A:
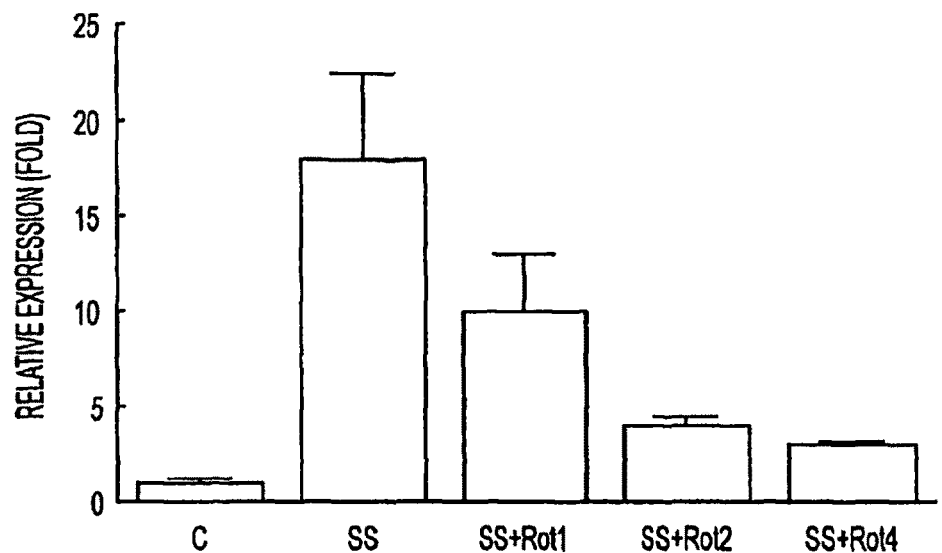
Figure 6B:
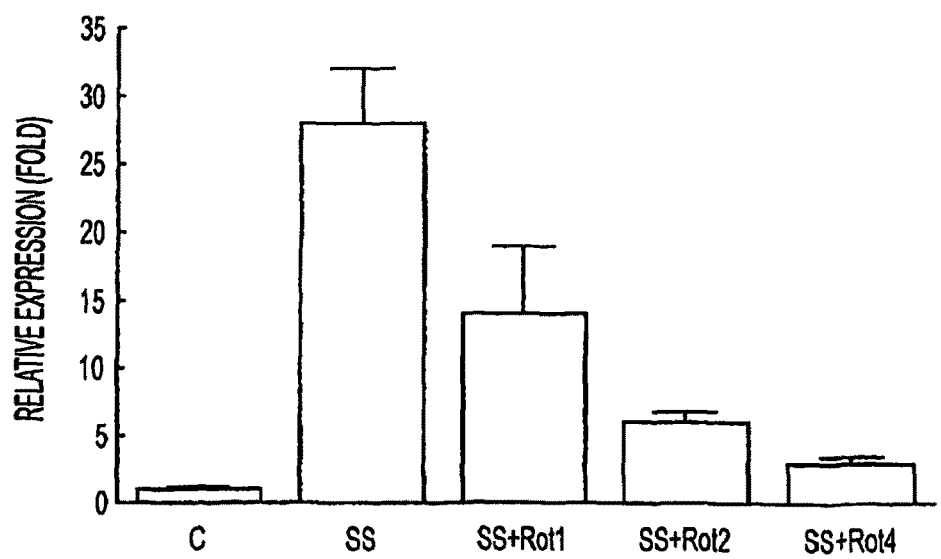
Figure 6C:
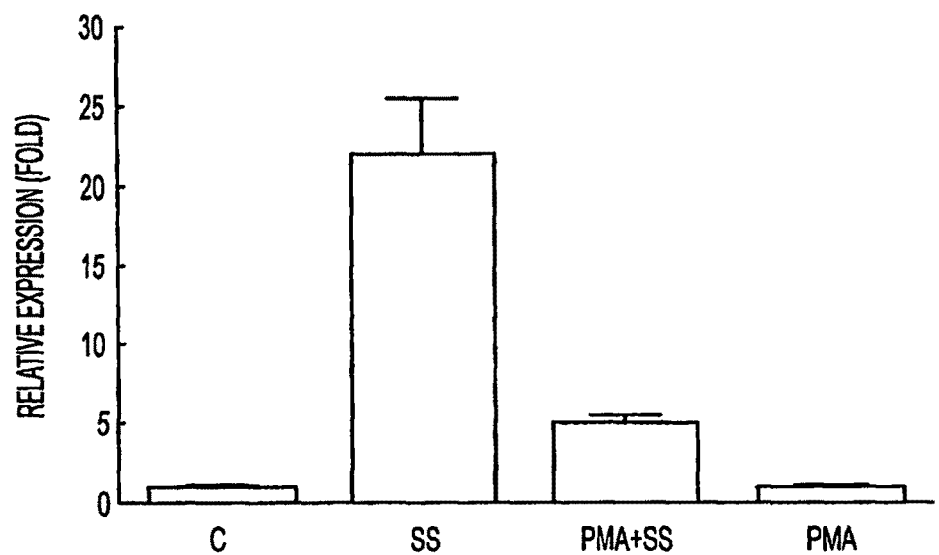
Figure 6D:
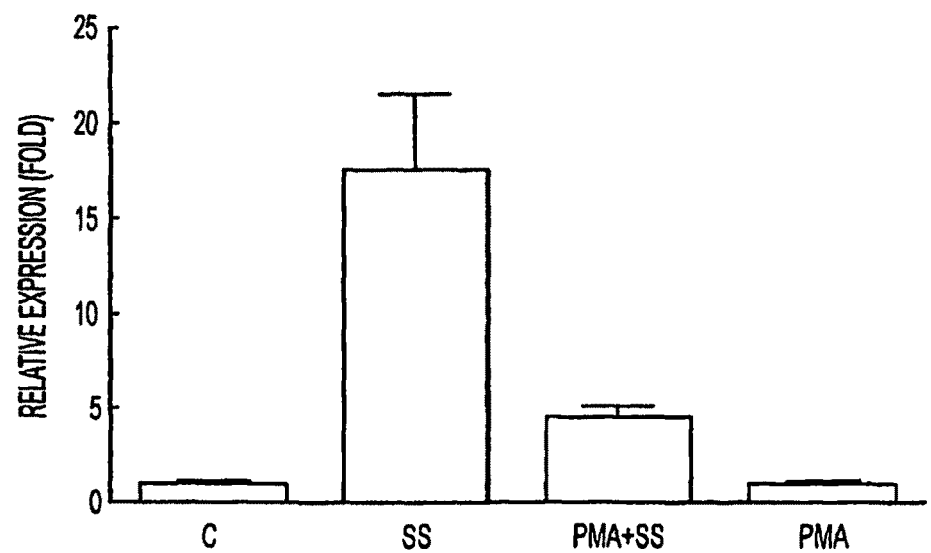

We previously reported that oxysterol-induced osteoblastic differentiation of cells is mediated via protein kinase C (PKC)- and protein kinase A (PKA)-dependent mechanisms. The role of these signaling pathways in regulating the different markers of osteoblastic differentiation appears to be both specific and overlapping. To begin elucidating the possible role of PKC and PKA in mediating oxysterol-induced Hh pathway activation, we examined the effect of PKC and PKA inhibitors on markers of Hh pathway activation. Pretreatment of M2 cells with the PKCδ selective inhibitor, rottlerin, previously found to inhibit osteoblastic differentiation induced by oxysterols, dose-dependently inhibited oxysterol-induced Gli-1 and Ptch mRNA expression (FIG. 6a,b). Similarly, oxysterol-induced Gli-1 and Ptch expression was inhibited in cells whose PKC stores were depleted following overnight pretreatment with 1 μM PMA (FIG. 6c,d). We next examined whether oxysterols induced PKC activation by assessing the levels of phosphorylated MARCKS (pMARCKS), a PKC substrate, by Western blotting. Whole cell lysates from M2 cells treated for 10 min, 30 min, 2 hours, 8 hours, 24 hours or 48 hours with 5 μM SS did not show any increase in pMARCKS levels compared to control untreated cells (data not shown), whereas a 30 min treatment with PMA clearly induced MARCKS phosphorylation.

To examine the possible role of PKA in oxysterol-induced Hh pathway activation, the effect of PKA inhibitor, H-89, previously found to inhibit the induction of some, but not all, markers of osteoblastic differentiation, on oxysterol-induced Gli-1 and Ptch mRNA expression was assessed by Q-RT-PCR. Results showed that pretreatment of M2 cells with H-89 (5-15 μM) did not inhibit oxysterol-induced Gli-1 or Ptch expression after 24 hours of treatment (data not shown). Furthermore, treatment of M2 cells for 24 hours with SS (5 μM) together with the PKA pathway activator, forskolin (10 μM), completely inhibited oxysterol-induced Gli-1 and Ptch expression (data not shown). Finally, Western blotting of whole cell lysates from oxysterol-treated cells showed no significant induction of phosphorylated PKA (pPKA) or phosphorylated CREB (pCREB) levels compared to control untreated cells at similar time points described above for the examination of pMARCKS levels (data not shown). In contrast, a 30 minute treatment with forskolin (10 μM) significantly induced pCREB levels.

Experiments such as those discussed above were conducted with the individual oxysterols of the invention to confirm that the osterinductive effects of those oxysterols are also mediated by hedgehog signaling. FIG. 10 shows that at least Oxy 8, 10, 11, 12, 13, and 14 stimulate the Gli1 reporter in M2-10B4 Marrow Stromal Cells.

Furthermore, the expression of Gli1 (a major mediator of hedgehog signaling events) is inhibited in M2 cells by using siRNA gene silencing methodology. Once we have confirmed that Gli1 expression is inhibited in our cells, we examine the effects of the synthetic oxysterols on those cells by assessing their ability to induce osteogenic cellular responses including Runx2 expression and DNA binding activity, osteocalcin mRNA expression, alkaline phosphatase activation and mineralization. It is expected that Example VIII Syntheses of Oxysterols Some sources pertaining to the synthesis of oxysterols are as follows: Drew, J. et al., *J. Org. Chem.*, 52 (1987) 4047-4052; Honda, T. et al., *J. Chem. Soc., Perkin Trans. 1*, (1996) 2291-2296; Gen, A. V. D. et al. *J. Am. Chem. Soc.*, 95 (1973) 2656-2663; Mazzocchi, P. H. et al. S. *J. Org. Chem.*, 48 (1983) 2981-2989; Byon C. et al., *J Org Chem*, 41 (1976) 3716-3722; Rao, A. S., *Comprehensive Organic Synthesis, Pergamon Press*, Eds. Trost B M, Fleming I., 7 (chapter 3.1) (1991) 376-380.

A. Method of Synthesis of Oxy11 and Oxy12

1. Route to Synthesis of Oxy11

Imidazole (ImH) can be added to a solution of pregnenolone (compound 3, see Scheme 1) in anhydrous dimethylformamide (DMF). Tert-butyldimethylsilyltrifluoromethanesulfonate can then be added to the solution. The reaction product can be purified to obtain compound 4, 1-((3S,8S,9S,10R,13S,14S,17S)-2,3,4,7,8,9,10,11,12,13,14,15,16,17-tetradecahydro-3-[(1,1-dimethylethyl)dimethylsilyloxy]-10,13-dimethyl-1H-cyclopenta[a]phenanthren-17-yl)ethanone, as shown in Scheme 2.

The Grignard reagent 3-methylbenzylmagnesium bromide can then be reacted with 4 in a mixture of diethyl ether and tetrahydrofuran (THF). The silyl ether can be removed by the addition of tetrabutylammonium fluoride to yield compound 5a (Oxy 11) as shown in Scheme 1.

2. Route to Synthesis of Oxy12

The Grignard reagent isoheptylmagnesium bromide can then be reacted with 4 in a mixture of diethyl ether and THF. The silyl ether can be removed by the addition of tetrabutylammonium fluoride to yield compound 5c (Oxy 12) as shown in Scheme 1.

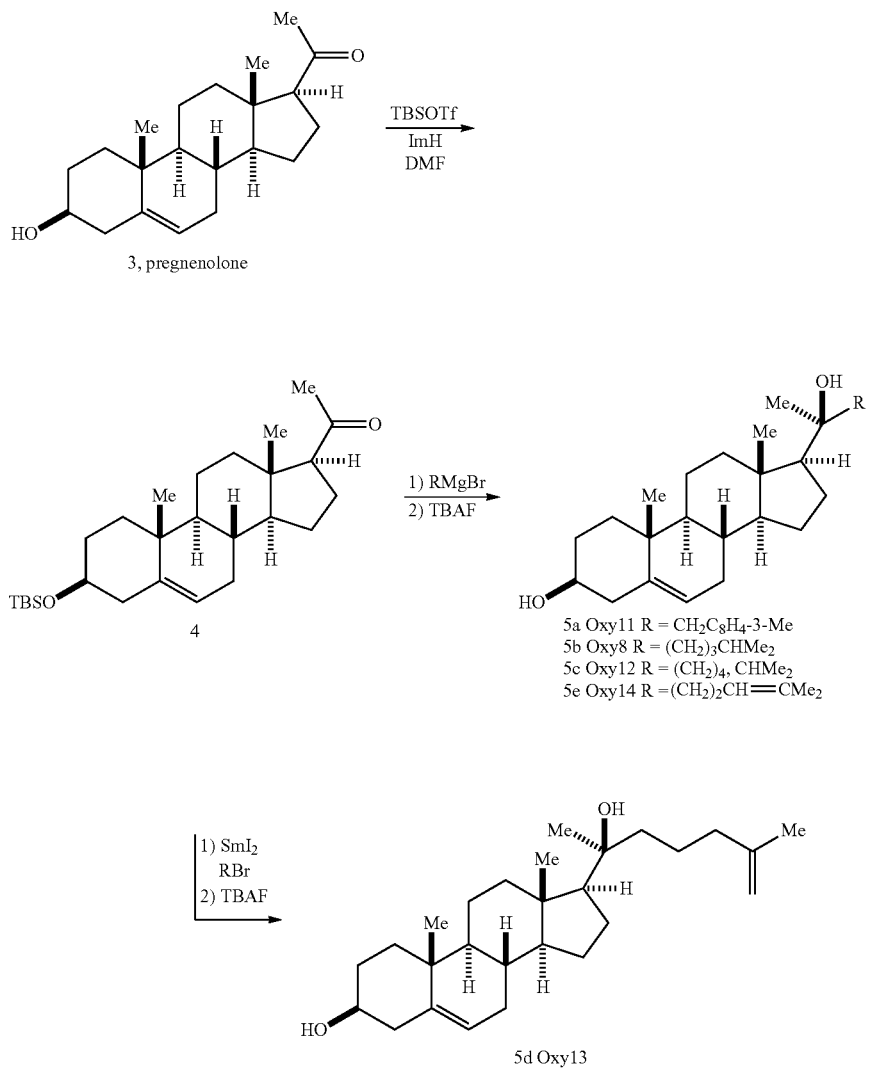

Scheme 1

B. Method of Synthesis of Oxy12 and Oxy13

1. Alternative Route to Synthesis of Oxy12

1-((3S,8S,9S,10R,13S,14S,17S)-2,3,4,7,8,9,10,11, 12,13,14,15,16,17-tetradecahydro-3-[(1,1-dimethyl-ethyl)dimethylsilyloxy]-10,13-dimethyl-1H-cyclo-penta[a]phenanthren-17-yl)ethanone, 1

To a stirred solution of pregnenolone (5.0 g, 15.8 mmol) in anhydrous dimethylformamide (DMF, 180 mL) was added imidazole (2.7 g. 39.7 mmol). The reaction was allowed to stir for 20 min followed by slow addition of tert-butyldimethylsilyl chloride (3.6 g., 23.9 mmol). After stirring for 12 h at ambient temperature, the reaction mixture was poured over ice. The precipitates were collected and dissolved in diethyl ether. The organic phases were washed with brine, dried over $Na_2SO_4$ and evaporated in vacuo to yield compound 1 (6.7 g, 15.6 mmol, 98%) as a white powder which was used without further purification. The spectroscopic data was identical to those reported in the literature (Drew et al. (1987) *J. Org. Chem.* 52, 4047-4052).

(3S,8S,9S,10R,13S,14S,17S)-2,3,4,7,8,9,10,11,12, 13,14,15,16,17-tetradecahydro-3-[(1,1-dimethyl-ethyl)dimethylsilyloxy]-17-((S)-2-hydroxy-7-meth-yloctan-2-yl)-10,13-dimethyl-1H-cyclopenta[a] phenanthrene, 2

To a stirred suspension of samarium metal (758 mg, 5.0 mmol) and 3 Å molecular sieves (0.5 g) in anhydrous tetrahydrofuran (THF, 9.5 mL) was slowly added a solution of 1,2-diiodoethane (1.3 g, 4.6 mmol) in THF (9.5 mL) at ambient temperature. After the reaction stirred for 30 min, hexamethylphosphoramide (HPMA, 3.0 mL, 17.2 mmol) was added to the reaction mixture and continued stirring for an additional 20 min. Then, a solution of ketone 1 (500.0 mg, 1.16 mmol) in THF (6.0 mL) was added followed by a solution of 1-bromo-5-methylhexane (208.0 mg, 1.16 mmol) in THF (2.0 mL). The reaction was allowed to stir for an additional hour until the starting material was completely consumed. After this, the reaction mixture was slowly treated with saturated $NaHCO_3$, filtered through Celite and rinsed three times with an excess amount of diethyl ether. The filtrate was treated with water and extracted with diethyl ether. The ether extracts were washed with brine, dried over $Na_2SO_4$ and evaporated in vacuo to give a residue which was purified via silica gel chromatography. Elution with hexane-diethyl ether (4:1, v/v) afforded compound 2 (350.0 mg, 0.6 mmol, 57%) as a white powder (Honda et al. (1996) *J. Chem. Soc., Perkin Trans.* 1, 2291-2296).

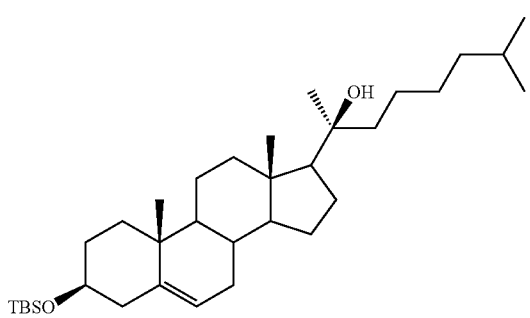 [SMILES: CC(C)CCCC[C@](C)(O)C1CCC2C3CC=C4C[C@@H](O[Si](C)(C)C(C)(C)C)CC[C@]4(C)C3CC[C@@]21C]

$^1$H NMR (500 MHz, $CDCl_3$) δ 0.05 (s, 6H), 0.86 (s, 3H), 0.86 (d, J=6.6 Hz, 6H), 0.89 (s, 9H), 1.00 (s, 3H), 1.02-1.17 (m, 8H), 1.26 (s, 3H), 1.29-1.81 (m, 18H), 1.95-1.99 (m, 1H), 2.07-2.10 (m, 1H), 2.14-2.18 (m, 1H), 2.24-2.26 (m, 1H), 3.46-3.50 (m, 1H), 5.31 (app t, J=5.2 Hz, 1H). $^{13}$C NMR (125 MHz, $CDCl_3$) δ −4.7, 13.5, 18.1, 19.3, 20.8, 22.2, 22.4, 22.5, 23.7, 24.4, 25.8, 26.3, 27.8, 27.9, 31.2, 31.7, 32.0, 36.5, 37.3, 38.9, 40.0, 42.5, 42.7, 43.9, 50.0, 56.8, 57.4, 72.4, 75.0, 120.9, 141.4.

(3S,8S,9S,10R,13S,14S,17S)-2,3,4,7,8,9,10,11,12, 13,14,15,16,17-tetradecahydro-17-((S)-2-hydroxy-7-methyloctan-2-yl)-10,13-dimethyl-1H-cyclopenta[a] phenanthren-3-ol, Oxy12

To a solution of compound 2 (300.0 mg, 0.57 mmol) in anhydrous THF was added a 1.0 M solution of tetrabutylammonium fluoride in THF (2.5 mL, 2.5 mmol) and the solution was allowed to stir at ambient temperature. After 12 h, the reaction was treated with water and extracted three times with diethyl ether. The organic phases were collected, dried over $Na_2SO_4$ and concentrated in vacuo to give an oil. Flash column chromatography of this oil (silica gel, 1:3 hexane/diethyl ether) yielded the compound Oxy12 (210.0 mg, 0.50 mmol, 88%) as a white powder.

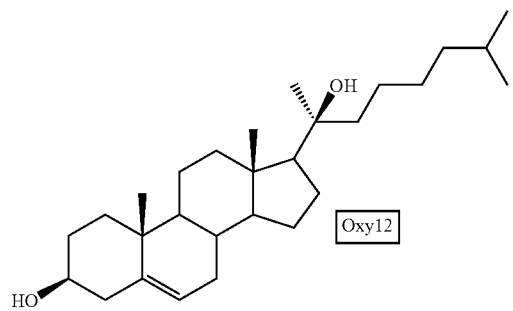 [SMILES: CC(C)CCCC[C@](C)(O)C1CCC2C3CC=C4C[C@@H](O)CC[C@]4(C)C3CC[C@@]21C]

$^1$H NMR (500 MHz, $CDCl_3$) δ 0.86 (s, 3H), 0.86 (d, J=6.6 Hz, 6H), 1.01 (s, 3H), 1.02-1.25 (m, 11H), 1.26 (s, 3H), 1.42-1.76 (m, 14H), 1.82-1.85 (m, 2H), 1.95-1.99 (m, 1H), 2.07-2.11 (m, 1H), 2.23-2.30 (m, 2H), 3.49-3.55 (m, 1H), 5.35 (app t, J=5.2 Hz, 1H). $^{13}$C NMR (125 MHz, $CDCl_3$) δ 13.5, 19.3, 20.8, 22.2, 22.5, 23.7, 24.4, 26.3, 27.8, 27.9, 31.2, 31.5, 31.7, 36.4, 37.1, 38.9, 39.0, 40.0, 42.2, 42.5, 44.0, 56.8, 57.5, 71.7, 75.1, 121.5, 140.7.

2. Route to Synthesis of Oxy13

Ethyl 4-methylpent-4-enoate, 7

A solution of 2-methyl-2-propen-1-ol (12.9 g, 0.18 mol), triethyl orthoacetate (230.0 mL, 1.3 mol) and propionic acid (0.9 mL, 0.12 mol) was heated to 170° C. (external). The reaction apparatus was equipped with a Vigreaux Claisen adapter with a collection flask to remove the ethanol produced. The reaction mixture was left under reflux overnight. The excess amount of triethyl orthoacetate was gently distilled off at 130 mm Hg until the temperature in the reaction flask began to increase. After the reaction was cool, the remaining liquid was treated with 300 mL of 10% monobasic potassium phosphate and the left reaction was stirred for 90 min at ambient temperature. The reaction mixture was extracted with diethyl ether (3×100 mL). The combined organic phase was dried over $Na_2SO_4$ and concentrated in vacuo to give a yellow oil. Flash column chromatography of this oil (silica gel, 4:1 hexane/diethyl ether) afforded compound 7 as a colorless oil (17.0 g, 0.12 mmol, 67%) (Gen et al. (1973) *J. Am. Chem. Soc.* 95, 2656-2663).

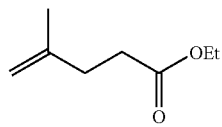

$^1$H NMR (500 MHz, CDCl$_3$) δ 1.25. (t, J=7.2 Hz, 3H), 1.74 (s, 3H), 2.33 (t, J=7.9 Hz, 2H), 2.45 (t, J=8.0 Hz, 2H), 4.13 (q, J=7.1 Hz, 2H), 4.68 (s, 1H), 4.74 (s, 1H).

4-Methylpent-4-en-1-ol, 8

To a flame-dried flask that was purged under argon for 20 min was added LiAlH$_4$ followed by 150 mL of anhydrous THF. The reaction mixture was cooled to 0° C. and a solution of compound 7 in THF (20 mL) was added slowly. The resulting solution was allowed to warm to room temperature and was stirred for 3 h until the starting material was completely consumed as indicated by TLC. The reaction was quenched by slow addition of the mixture to 300 mL of ice cold 1M NaOH. The mixture was then allowed to stir for another hour and was filtered through Celite. A large amount of diethyl ether was used for rinsing. The filtrate was treated with water and extracted twice with diethyl ether. The combined organic phase was dried over Na$_2$SO$_4$ and evaporated in vacuo to give a residue which was purified via distillation at 20 mm Hg (bp 65-68° C.) to afford compound 8 as a yellow oil (9.5 g, 0.095 mol, 79%) (Mazzocchi et al. (1983) *J. Org. Chem.* 4, 2981-2989).

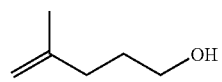

$^1$H NMR (500 MHz, CDCl$_3$) δ 1.47 (br, 1H), 1.69-1.74 (m, 5H), 2.1 (t, J=7.5 Hz, 2H), 3.66 (t, J=6.5 Hz, 2H), 4.71 (d, J=0.8 Hz, 1H), 4.73 (d, J=0.8 Hz, 1H), 4.73 (d, J=0.4 Hz, 1H); $^{13}$C NMR (125 MHz, CDCl$_3$), δ 22.22, 30.41, 33.98, 62.64, 110.08, 145.40.

5-Bromo-2-methyl-1-pentene, 9

To a solution of compound 8 (8.8 g, 0.088 mol) in pyridine (150 mL) cooled to 0° C. was added p-toluenesulfonyl chloride (35.0 g, 0.18 mol) in small portions. After the reaction mixture stirred for 20 minutes, it was allowed the reaction mixture to warm to room temperature over 3 h. The solution was acidified with 1 M HCl and extracted three times with diethyl ether. The ether extracts were washed with 1 M HCL, saturated NaHCO$_3$ and brine. The combined organic layers were dried over Na$_2$SO$_4$ and evaporated in vacuo to yield the crude tosylate which was used without further purification.

The tosylate (23.8 g, 0.094 mol) was dissolved in acetone (150 mL) and LiBr (17.0 g, 0.20 mol) was added slowly at ambient temperature. The reaction was left under reflux at 75° C. for 3 h. The solution was poured into ice water and extracted with diethyl ether (3×200 mL). The combined the organic layers were dried over Na$_2$SO$_4$ and concentrated in vacuo to afford a yellow oil. Flash column chromatography of this oil (silica gel, 9:1 hexane/diethyl ether) gave compound 9 (7.0 g, 0.043 mol, 49%) as a colorless oil.

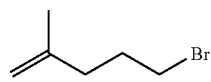

$^1$H NMR (500 MHz, CDCl$_3$) δ 1.73 (s, 3H), 1.97-2.02 (m, 2H), 2.16 (t, J=7.2 Hz, 2H), 3.41 (t, J=6.7 Hz, 2H), 4.72 (d, J=1.0 Hz, 1H), 4.76 (d, J=0.5 Hz, 1H); $^{13}$C NMR (125 MHz, CDCl$_3$) δ 22.18, 30.47, 33.17, 35.92, 110.88, 143.82.

(3S,8S,9S,10R,13S,14S,17S)-2,3,4,7,8,9,10,11,12, 13,14,15,16,17-tetradecahydro-3[(1,1-dimethylethyl) dimethylsilyloxy]-17-((S)-2-hydroxy-6-methylhept-6-en-2-yl)-10,13-dimethyl-1H-cyclopenta[a] phenanthrene, 10

The coupling reaction of the protected pregnenolone 1 (500.0 mg, 1.16 mmol) with 5-bromo-2-methyl-1-pentene 9 (199.0 mg, 1.22 mmol) in the presence of samarium diiodide was performed under similar condition as described for the preparation of 2 to afford the 20S-hydroxy steroid 10 (419.0 mg, 0.82 mmol, 71%) as a white powder.

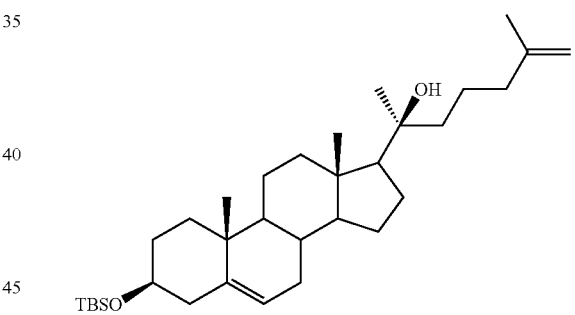

$^1$H NMR (500 MHz, CDCl$_3$) δ 0.05 (s, 6H), 0.86 (s, 3H), 0.89 (s, 9H), 1.00 (s, 3H), 1.13-1.22 (m, 5H), 1.28 (s, 3H), 1.32-1.55 (m, 11H), 1.71 (s, 3H), 1.72-1.79 (m, 5H), 1.97-2.10 (m, 6H), 3.47-3.48 (m, 1H), 4.67 (s, 1H), 4.70 (s, 1H), 5.31 (app t, J=5.3 Hz, 1H). $^{13}$C NMR (125 MHz, CDCl$_3$) δ −4.7, 13.5, 18.1, 19.3, 20.8, 22.1, 22.2, 22.3, 23.7, 25.8, 26.3, 31.2, 31.7, 32.0, 36.5, 37.3, 38.2, 40.0, 42.6, 42.7, 43.4, 50.0, 56.8, 57.7, 72.5, 75.0, 109.8, 120.9, 141.5, 145.7.

(3S,8S,9S,10R,13S,14S,17S)-2,3,4,7,8,9,10,11,12, 13,14,15,16,17-tetradecahydro-17-((S)-2-hydroxy-6-methylhept-6-en-2-yl)-10,13-dimethyl-1H-cyclopenta[a]phenanthren-3-ol, Oxy13

The deprotection of the silyl ether 10 was carried out under similar conditions as those used for the preparation of the compound Oxy12 to afford compound Oxy13 (300.0 mg, 0.75 mmol, 91%) as a white powder.

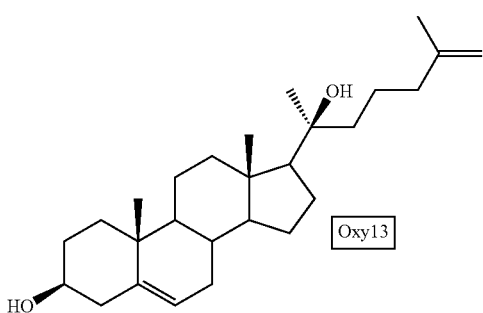 [SMILES: C=C(C)CCC[C@](C)(O)C1CCC2C3CC=C4C[C@@H](O)CC[C@]4(C)C3CC[C@@]21C]

¹H NMR (500 MHz, CDCl₃) δ 0.86 (s, 3H), 1.00 (s, 3H), 1.12-1.20 (m, 5H), 1.28 (s, 3H), 1.32-1.65 (m, 14H), 1.73 (s, 3H), 1.83-2.0 (m, 5H), 2.07-2.09 (m, 1H), 2.23-2.28 (m, 2H), 2.48 (br, 1H), 3.52-3.54 (m, 1H), 4.67 (s, 1H), 4.70 (s, 1H), 5.35 (app t, J=2.0 Hz, 1H). ¹³C NMR (125 MHz, CDCl₃) δ 13.5, 19.3, 20.8, 22.1, 22.2, 22.3, 23.7, 26.3, 31.2, 31.5, 31.7, 36.4, 37.1, 38.2, 40.0, 42.2, 42.6, 43.4, 49.9, 56.8, 57.7, 71.6, 75.0, 109.8, 121.5, 140.7, 145.7.

C. Method of Synthesis of Oxy15 and Oxy16

The pregnenolone silyl ether (compound 4, see Schemes 1 and 2) can be reacted with 4-methylpentynyllithium in tetrahydrofuran (THF) and the resulting alcohol was then reduced using Lindlar's catalyst to give a mixture of cis and trans alkenes which were separated. The cis isomer was epoxidized using t-butyl hydroperoxide and vanadyl acetoacetate to give a mixture of the two epoxides (the first shown in Scheme 2 being major). Hydride reduction of the hydroxy epoxides individually gave the diols. Final removal of the silyl ether of the two diols gave the triols, Oxy15 and Oxy16.

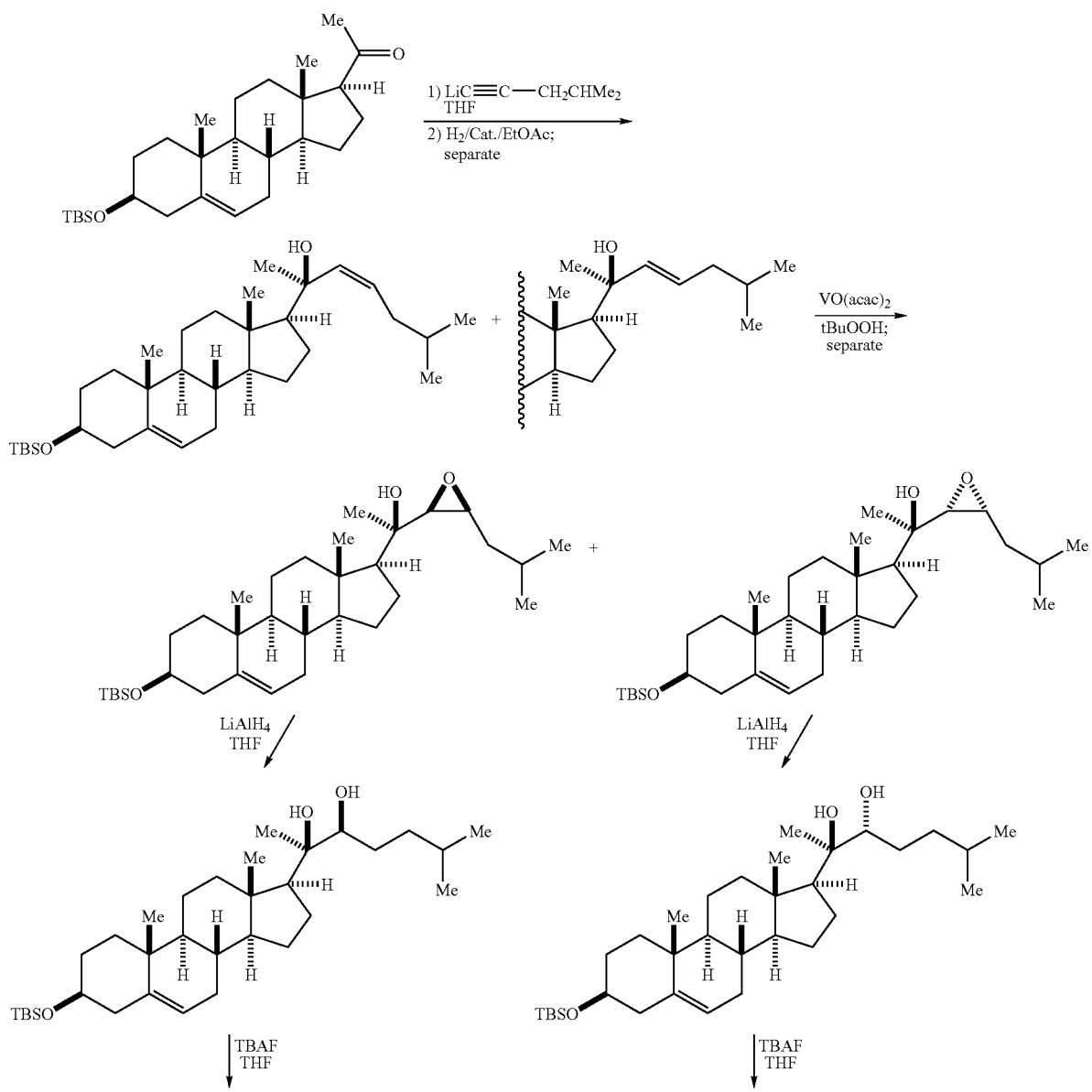

Scheme 2

41

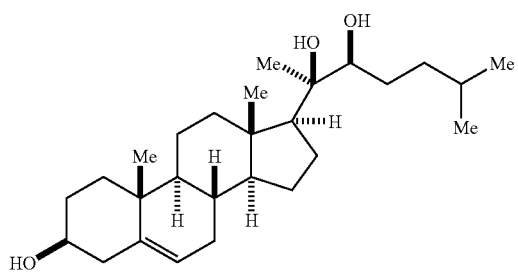

42

-continued

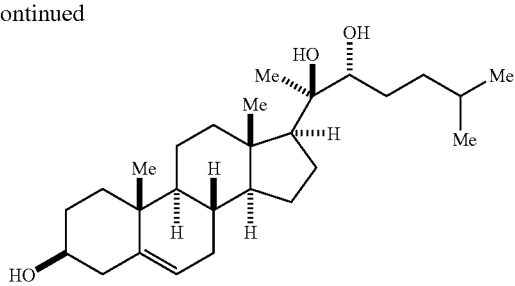

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above and in the figures, including U.S. provisional applications 60/776,990, filed Feb. 27, 2006; 60/802,737, filed May 22, 2005; and 60/809,736, filed May 31, 2006; all of which are hereby incorporated by reference in their entirety.

We claim:
1. A compound of the structure:

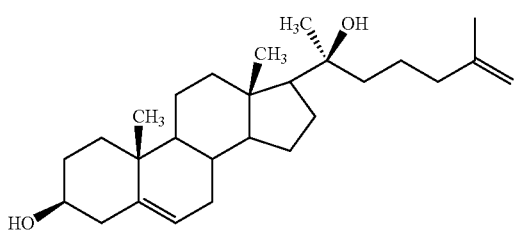

2. A pharmaceutical composition, comprising a compound of the structure:

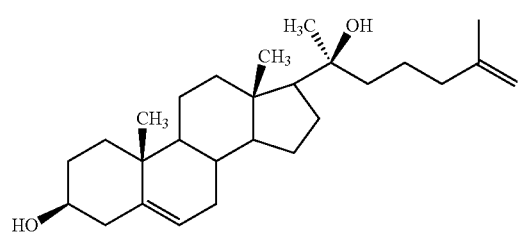

and a pharmaceutically acceptable carrier.

3. A pharmaceutical composition comprising:
(i) a compound of the structure:

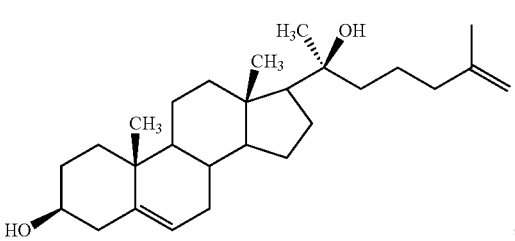

(II)

(ii) at least one of 20(S)-hydroxycholesterol, 22(S)-hydroxycholesterol, or 22(R)-hydroxycholesterol; and
a pharmaceutically acceptable carrier.

4. A method for stimulating a hedgehog (Hh) pathway in a cell or tissue in vitro, comprising contacting the cell or tissue with an effective amount of a compound of the structure:

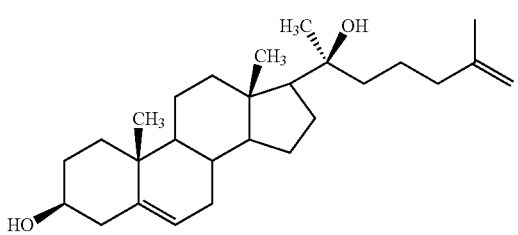 [SMILES: C=C(C)CCC[C@](C)(O)C1CCC2C3CC=C4C[C@@H](O)CC[C@]4(C)C3CC[C@@]21C]

5. A method for treating a subject with a bone fracture, osteoporosis, osteoporitis, obesity, or osteoarthritis, comprising administering to the subject an effective amount of a pharmaceutical composition comprising a compound of the structure:

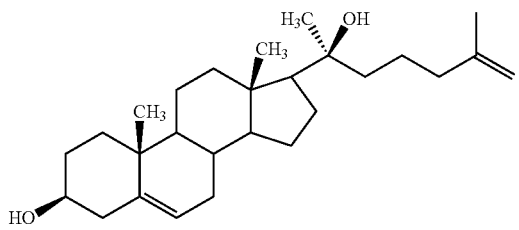 [SMILES: C=C(C)CCC[C@](C)(O)C1CCC2C3CC=C4C[C@@H](O)CC[C@]4(C)C3CC[C@@]21C]

6. A method for indicating osteoblastic differentiation of a mammalian mesenchymal stem cell, comprising contacting the cell with an effective amount of a pharmaceutical composition comprising a compound of the structure:

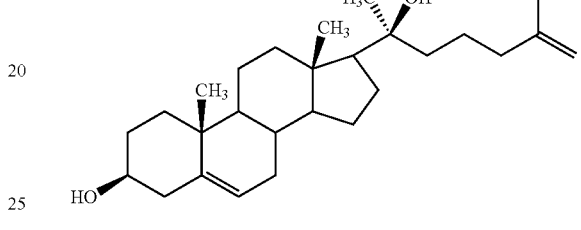

7. The method of claim 6, further comprising treating the mammalian mesenchymal cell with at least one secondary agent, selected from the group consisting of parathyroid hormone, sodium fluoride, insulin-like growth factor I (ILGF-I), insulin-like growth factor II (ILGF-II), transforming growth factor beta (TGF-β), cytochrome P450 inhibitors, phospholipase activators, arachadonic acid, COX enzyme activators, osteogenic prostanoids, and ERK activators.

8. A method for stimulating a mammalian cell to express a level of a biological marker of osteoblastic differentiation which is greater than the level of the biological marker in an untreated cell, comprising exposing the mammalian cell to an effective amount of a pharmaceutical composition comprising a compound of the structure:

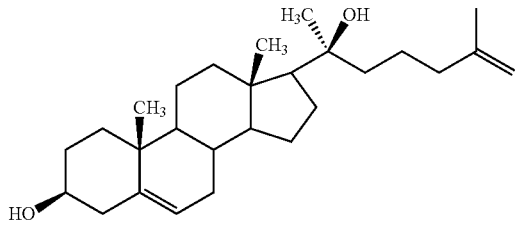 [SMILES: C=C(C)CCC[C@](C)(O)C1CCC2C3CC=C4C[C@@H](O)CC[C@]4(C)C3CC[C@@]21C]

wherein the biological marker is alkaline phosphatase activity, calcium incorporation, mineralization and/or expression of osteocalcin mRNA.

9. The method of claim 8, wherein the mammalian cell is selected from the group consisting of a mesenchymal stem cell, an osteoprogenitor cell and a cell in a calvarial organ culture.

10. The method of claim 6, wherein the mammalian mesenchymal stem cell is a marrow stromal cell in a subject, and further comprising administering the pharmaceutical composition at a therapeutically effective dose in an effective dosage form at a selected interval to increase the number of osteoblasts present in bone tissue for treating the subject to increase the differentiation of marrow stromal cells into osteoblasts.

11. A method for treating a patient to induce bone formation comprising administering a pharmaceutical composition comprising a compound of the structure:

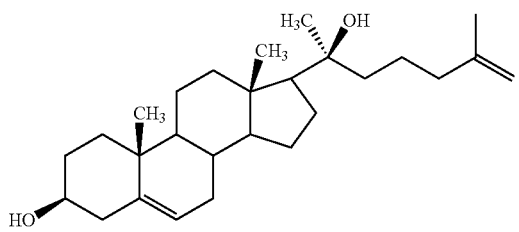 [SMILES: C=C(C)CCC[C@](C)(O)C1CCC2C3CC=C4C[C@@H](O)CC[C@]4(C)C3CC[C@@]21C]

at a therapeutically effective dose in an effective dosage form at a selected interval to increase bone mass.

12. A method for treating osteoporosis in a patient, comprising administering a pharmaceutical composition comprising a compound of the structure:

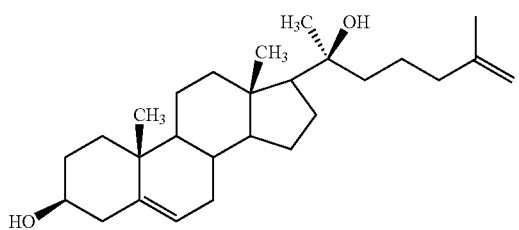 [SMILES: C=C(C)CCC[C@](C)(O)C1CCC2C3CC=C4C[C@@H](O)CC[C@]4(C)C3CC[C@@]21C]

at a therapeutically effective dose.

13. A method for treating a subject to induce bone formation comprising:

harvesting mammalian mesenchymal stem cells;

treating the mammalian mesenchymal cells with a compound of the structure:

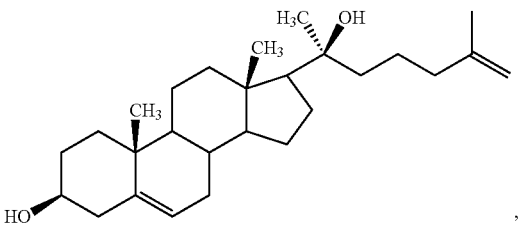 [SMILES: C=C(C)CCC[C@](C)(O)C1CCC2C3CC=C4C[C@@H](O)CC[C@]4(C)C3CC[C@@]21C]

wherein the compound induces the mesenchymal stem cells to express at least one cellular marker of osteoblastic differentiation; and administering the differentiated cells to the subject.

14. An implant for use in the human body comprising a substrate having a surface, wherein at least the surface of the implant includes a pharmaceutical composition comprising a compound of the structure:

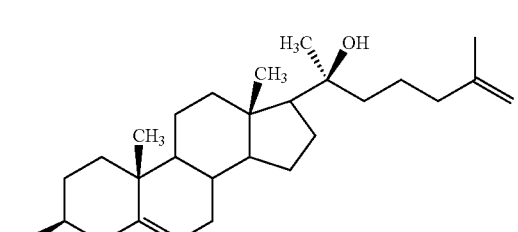

in an amount sufficient to induce bone formation in the surrounding bone tissue.

15. The implant of claim 14, wherein the substrate is formed into the shape of a pin, screw, plate, or prosthetic joint.

16. A method for inhibiting a measurable amount of adipocyte differentiation of a mammalian mesenchymal stem cell, comprising contacting the mesenchymal stem cell with an effective amount of a pharmaceutical composition comprising a compound of the structure:

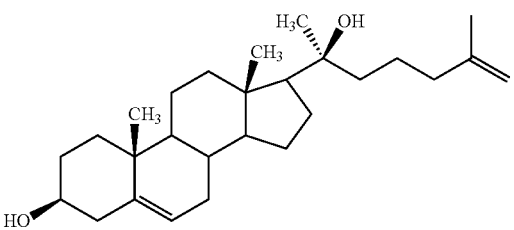 [SMILES: C=C(C)CCC[C@](C)(O)C1CCC2C3CC=C4C[C@@H](O)CC[C@]4(C)C3CC[C@@]21C]

17. A method for treating a subject in need of an increase in osteomorphogenesis, osteoproliferation, weight reduction, or the enhancement of cartilage production, comprising administering to the subject an effective amount of a pharmaceutical composition comprising a compound of the structure:

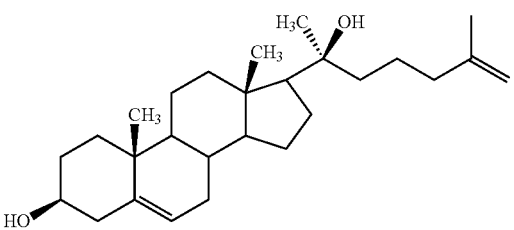 [SMILES: C=C(C)CCC[C@](C)(O)C1CCC2C3CC=C4C[C@@H](O)CC[C@]4(C)C3CC[C@@]21C]

* * * * *